(12) United States Patent
Kamath et al.

(10) Patent No.: US 9,036,888 B2
(45) Date of Patent: May 19, 2015

(54) SYSTEMS AND METHODS FOR PERFORMING QUALITY REVIEW SCORING OF BIOMARKERS AND IMAGE ANALYSIS METHODS FOR BIOLOGICAL TISSUE

(75) Inventors: Vidya Pundalik Kamath, Clifton Park, NY (US); Alberto Santamaria-Pang, Guilderland, NY (US); Brion Daryl Sarachan, Schenectady, NY (US); Jens Rittscher, Ballston Lake, NY (US)

(73) Assignee: General Electric Company, Niskayuna, NY (US)

( * ) Notice: Subject to any disclaimer, the term of this patent is extended or adjusted under 35 U.S.C. 154(b) by 402 days.

(21) Appl. No.: 13/460,081

(22) Filed: Apr. 30, 2012

(65) Prior Publication Data
US 2013/0287283 A1    Oct. 31, 2013

(51) Int. Cl.
| | | |
|---|---|---|
| G06K 9/00 | (2006.01) | |
| G09G 5/02 | (2006.01) | |
| G06K 9/62 | (2006.01) | |
| G01N 15/14 | (2006.01) | |

(52) U.S. Cl.
CPC .............. *G09G 5/026* (2013.01); *G06K 9/6263* (2013.01); *G06K 9/0014* (2013.01); *G06K 9/6253* (2013.01); *G01N 15/1475* (2013.01); *G09G 2340/12* (2013.01); *G09G 2370/022* (2013.01); *G09G 2380/08* (2013.01)

(58) Field of Classification Search
None
See application file for complete search history.

(56) References Cited

U.S. PATENT DOCUMENTS

| | | | |
|---|---|---|---|
| 5,235,522 A | 8/1993 | Bacus | |
| 5,799,101 A * | 8/1998 | Lee et al. | 382/133 |
| 6,111,259 A | 8/2000 | Arai | |
| 7,899,624 B2 | 3/2011 | Cualing et al. | |
| 8,200,527 B1 * | 6/2012 | Thompson et al. | 705/7.39 |
| 8,204,779 B1 * | 6/2012 | Hughes et al. | 705/7.39 |
| 8,204,809 B1 * | 6/2012 | Wise | 705/35 |
| 8,432,390 B2 * | 4/2013 | Givon | 345/419 |
| 8,781,815 B1 * | 7/2014 | Gidney | 704/9 |
| 2005/0207633 A1 | 9/2005 | Arini et al. | |
| 2005/0278247 A1 * | 12/2005 | Benedict et al. | 705/38 |
| 2007/0122025 A1 * | 5/2007 | Christian et al. | 382/141 |
| 2007/0143345 A1 * | 6/2007 | Jones et al. | 707/104.1 |
| 2008/0032328 A1 | 2/2008 | Cline et al. | |
| 2008/0033657 A1 | 2/2008 | Cline et al. | |
| 2008/0065471 A1 * | 3/2008 | Reynolds et al. | 705/10 |
| 2008/0137937 A1 | 6/2008 | Athelogou et al. | |

(Continued)

OTHER PUBLICATIONS

Susan Holmes, an interactive Java Statistical image segmentation system: Gemldent, Published J Stat Softw. Jun. 1, 2009; 30(10).*

(Continued)

*Primary Examiner* — Chan Park
*Assistant Examiner* — Iman K Kholdebarin
(74) *Attorney, Agent, or Firm* — Fletcher Yoder, P.C.

(57) ABSTRACT

Exemplary embodiments include methods, systems, and devices for enabling users to provide quality scores for indicating the quality of image analysis methods performed on images of biological tissue. An exemplary user interface displays results of an image analysis method performed on an image of biological tissue in an overlaid manner on an image of biological tissue. The exemplary user interface enable a user to provide, directly on the user interface, one or more quality scores to indicate the user's assessment of the quality of the image analysis performed on the image. Exemplary embodiments store the quality scores provided by the user in association with the image analysis method and the image of biological tissue.

28 Claims, 42 Drawing Sheets

(56) References Cited

U.S. PATENT DOCUMENTS

| | | | | |
|---|---|---|---|---|
| 2008/0152122 | A1* | 6/2008 | Idan et al. | 379/265.07 |
| 2008/0166014 | A1* | 7/2008 | Marcus et al. | 382/103 |
| 2008/0181417 | A1* | 7/2008 | Pereg et al. | 381/17 |
| 2008/0195387 | A1* | 8/2008 | Zigel et al. | 704/236 |
| 2009/0298703 | A1 | 12/2009 | Gough et al. | |
| 2010/0177950 | A1* | 7/2010 | Donovan et al. | 382/133 |
| 2010/0183225 | A1* | 7/2010 | Vantaram et al. | 382/173 |
| 2010/0184093 | A1* | 7/2010 | Donovan et al. | 435/7.21 |
| 2010/0192084 | A1 | 7/2010 | Ingermanson et al. | |
| 2011/0034411 | A1* | 2/2011 | Xu et al. | 514/57 |
| 2011/0065113 | A1* | 3/2011 | Chinnaiyan et al. | 435/6 |
| 2011/0091081 | A1 | 4/2011 | Sarachan et al. | |
| 2011/0091091 | A1* | 4/2011 | Sarachan et al. | 382/133 |
| 2011/0091384 | A1 | 4/2011 | Alani et al. | |
| 2011/0106656 | A1* | 5/2011 | Schieffelin | 705/26.9 |
| 2011/0150334 | A1* | 6/2011 | Du et al. | 382/173 |
| 2011/0164677 | A1* | 7/2011 | Lu et al. | 375/240.02 |
| 2011/0311111 | A1* | 12/2011 | Allburn | 382/115 |
| 2011/0317898 | A1* | 12/2011 | Shi et al. | 382/131 |
| 2012/0269441 | A1* | 10/2012 | Marchesotti et al. | 382/195 |
| 2012/0316917 | A1* | 12/2012 | Tellis et al. | 705/7.29 |
| 2012/0330990 | A1* | 12/2012 | Chen et al. | 707/761 |
| 2013/0080134 | A1* | 3/2013 | Donovan et al. | 703/11 |
| 2013/0151398 | A1* | 6/2013 | Mateti et al. | 705/38 |
| 2013/0230230 | A1* | 9/2013 | Ajemba et al. | 382/133 |
| 2013/0279801 | A1* | 10/2013 | Scheuermann et al. | 382/164 |
| 2013/0286038 | A1* | 10/2013 | Kamath et al. | 345/592 |
| 2013/0286043 | A1* | 10/2013 | Kamath et al. | 345/619 |
| 2013/0287283 | A1* | 10/2013 | Kamath et al. | 382/133 |
| 2013/0290006 | A1* | 10/2013 | Kamath et al. | 705/2 |
| 2013/0290225 | A1* | 10/2013 | Kamath et al. | 706/12 |
| 2013/0301910 | A1* | 11/2013 | Mel et al. | 382/159 |
| 2014/0089020 | A1* | 3/2014 | Murphy | 705/5 |
| 2014/0235458 | A1* | 8/2014 | Houldsworth et al. | 506/2 |

OTHER PUBLICATIONS

Susan Holmes, An Interactive Java Statistical Image Segmentation System: GemIdent, J Stat Softw. Jun. 1, 2009; 30(10): i10.*

"Game Changer in Pathology Software," University of Michigan.

"I-Path Launches TMA Toolbox for Online Biomarker Discovery", I-Path (Jul. 29, 2010).

"IHC-MARK Quantitation Software", OncoMark Limited, Product Catalogue.

"Image Analysis Service", OracleBio, Product Catalogue.

Al-Kofahi et al., "Cell-Based Quantification of Molecular Biomarkers in Histopathology Specimens," Histopathology vol. 59(1):40-54 (2011).

Cualing et al., "Virtual Flow Cytometry of Immunostained Lymphocytes on Microscopic Tissue Slides: iHCFlowTM Tissue Cytometry," Cytometry Part B (Clinical Cytometry) 72B:63-76 (2007).

iBrowser Data Integration Software, <http://www.compucyte.com/ibrowser.htm>.

iCyte Automated Imaging Cytometer, <http://www.compucyte.com/icyte.htm>.

iCyte or iCys Cytometric Analysis Software, http://www.compucyte.com/softwareicyte.htm.

iNovator Application Development Toolkit, <http://www.compucyte.com/inovator.htm>.

Laser Scanning Cytometry in an Inverted Format, www.compucyte.com.

Peterson et al., "Applications of Laser Scanning Cytometry in Immunohistochemistry and Routine Histopathology," Toxicologic Pathology, 36:117-132 (2008).

Schubert et al., "Analyzing proteome topology and function by automated multidimensional fluorescence microscopy," Nat Biotechnol vol. 24(10):1270-1278 (2006).

Tissue Gnostics HistoQuest Cell Analysis Software, <http://www.tissuegnostics.com/EN/software/histoquest.php>.

Tissue Gnostics TissueQuest Cell Analysis Software, <http://www.tissuegnostics.com/EN/software/tissuequest.php>.

VirtuosoTM Ventana test systems, Product Catalogue.

Search Report and Written Opinion from corresponding PCT Application No. PCT/EP2013/058786 dated Oct. 7, 2013.

Search Report and Written Opinion from corresponding PCT Application No. PCT/EP2013/058785 dated Oct. 15, 2013.

Marcelpoil, "Quantification of Molecular Pathology: Colorimetric Immunohistochemistry" In: "Molecular Pathology in Drug Discovery and Development", John Wiley & Sons, Inc., pp. 259-294, Jan. 1, 2009.

Matula et al., "Single-cell-based image analysis of high-throughput cell array screens for quantification of viral infection", Cytometry Part A, vol. 75A, No. 4, pp. 309-318, Apr. 1, 2009.

Holmes et al., "An Interactive Java Statistical Image Segmentation System: GemIdent", Journal of Statistical Software, pp. 1-20, Jun. 1, 2009.

International Search Report and Written Opinion issued in connection with corresponding PCT Application No. PCT/EP2013/058784 dated Oct. 21, 2013.

Gallagher, "Digital Image Processing and Analysis with ImageJ" In: "Current Protocols Essential Laboratory Techniques", Jan. 1, 2008.

Jones et al., "CellProfiler Analyst: data exploration and analysis software for complex image-based screens", BMC Bioinformatics, vol. No. 9, Issue No. 1, pp. 482, Nov. 15, 2008.

* cited by examiner class Cell

Attributes 3402

Identifier
SampleIdentifier
TissueIdentifier
Type
Size
Boundaries
Location
ExpressionLevel
...

3400

Methods 3404 getIdentifier; setIdentifier
getSampleIdentifier; setSampleIdentifier
getTissueIdentifier; setTissueIdentifier
getType; setType
getSize; setSize
getBoundaries; setBoundaries
getLocation; setLocation
getExpressionLevel; setExpressionLevel
renderCell
renderCellExpressionLevel
...

FIG. 34

SYSTEMS AND METHODS FOR PERFORMING QUALITY REVIEW SCORING OF BIOMARKERS AND IMAGE ANALYSIS METHODS FOR BIOLOGICAL TISSUE

BACKGROUND

Examination of tissue specimens that have been treated to reveal the expression of biomarkers is a known tool for biological research and clinical studies. One such treatment involves the use of antibodies or antibody surrogates, such as antibody fragments, that are specific for the biomarkers, commonly proteins, of interest. Such antibodies or antibody surrogates can be directly or indirectly labeled with a moiety capable, under appropriate conditions, of generating a signal. For example, a fluorescent moiety can be attached to the antibody to interrogate the treated tissue for fluorescence. The signal obtained is commonly indicative of both the presence and the amount of biomarker present.

The techniques of tissue treatment and examination have been refined so that the level of expression of a given biomarker in a particular cell or even a compartment of the given cell such as the nucleus, cytoplasm or membrane can be quantitatively determined. The boundaries of these compartments or the cell as a whole are located using known histological stains. Commonly the treated tissue is examined with digital imaging and the level of different signals emanating from different biomarkers can consequently be readily quantified.

A technique has further been developed which allows testing a given tissue specimen for the expression of numerous biomarkers. Generally, this technique involves staining the specimen with a fluorophore labeled probe to generate a signal for one or more probe bound biomarkers, chemically bleaching these signals, and re-staining the specimen to generate signals for some further biomarkers. The chemical bleaching step is convenient because there are only a limited number of signals that can be readily differentiated from each other so only a limited number of biomarkers can be examined in a particular step. With bleaching, a tissue sample may be re-probed and re-evaluated for multiple steps. This cycling method may be used on formalin fixed paraffin embedded tissue (FFPE) samples and cells. Digital images of the specimen are collected after each staining step. The successive images of such a specimen can conveniently be kept in registry using morphological features such as DAPI stained cell nuclei, the signal of which is not modified by the chemical bleaching method.

Another approach has been to examine frozen tissue specimens by staining them iteratively and photo bleaching the labels from the previous staining step before applying the next set of stains. The strength of the fluorescent signal associated with each biomarker evaluated is then extracted from the appropriate image.

One conventional technique for analyzing a biological sample is flow cytometry. In flow cytometry, a biological particle, suspended in a stream of fluid, flows by a detection system configured to detect one or more characteristics of the particle (for example, bio-marker expressions level). Flow cytometry can advantageously facilitate identification of different populations of particles in a biological sample based on phenotype. Thus, flow cytometry is routinely used to aid in the diagnosing of health conditions such as cancer. Another, common application is to use flow cytometry to analyze and physically sort particles based on detected characteristics, for example, so as to isolate a population of interest.

Despite its advantages, flow cytometry has many limitations when it comes to analyzing a biological sample. One such limitation is that flow cytometry requires the destruction of an original biological sample in order to break the biological sample into individual biological particles for analysis. Another related limitation is that, due to its destructive nature, flow cytometers are unable to detect or analyze inter-particle morphological characteristics, such as physical proximity, as were reflected in the original biological sample. Embodiments of the present disclosure advantageously provide many of the advantages of conventional flow cytometry without such limitations.

SUMMARY

Embodiments disclosed herein include methods, systems, and devices for enabling users to provide quality review scores for indicating the quality of image analysis methods performed on images of biological tissue. Exemplary embodiments enable a user to select, directly on a user interface, a field-of-view of biological tissue for display on the user interface. The ability to select particular studies/experiments, slides, spots and biomarkers using the tools provided on the user interface makes it unnecessary for a user to remember the locations of the files related to the studies/experiments, slides, spots and biomarkers, and allows the user to select data sources in an intuitive, time-efficient and user-friendly manner. In addition, the exemplary user interface enables a user to assess and provide quality review scores of image analysis methods performed on a plurality of fields-of view of biological tissue in a single session of using the user interface.

An exemplary user interface displays results of an image analysis method performed on an image of biological tissue in an overlaid manner on an image of biological tissue. The exemplary user interface enable a user to provide, directly on the user interface, one or more quality review scores to indicate the user's assessment of the quality of the image analysis performed on the image. Exemplary embodiments may store the quality review scores provided by the user in association with the image analysis method and the image of biological tissue.

Image segmentation analysis is one analysis method that may be performed on an image of biological tissue obtained after treating the biological tissue using a biomarker. The results of the image segmentation analysis may delineate biological units of interest (e.g., cells) in the image of biological tissue. The exemplary user interface may display the results of the image segmentation analysis in an overlaid manner over the image of the biological tissue. The exemplary user interface enable a user to provide an image segmentation quality score to indicate the quality and suitability of the image segmentation analysis method, and a biomarker quality score to indicate the quality and suitability of the biomarker used to treat the biological tissue in obtaining the image of the biological tissue.

In accordance with one exemplary embodiment, a computer-implemented method is provided for performing quality review of analysis of biological tissue. The method may include rendering a graphical user interface on a visual display device. The method may include rendering, on the graphical user interface, a field-of-view selection component allowing a user to select a field-of-view from a data set comprising tissue profile data including multiplexed biomarker images capturing expression of a plurality of biomarkers in a plurality of fields of view of biological tissue. The field-of-view selection component may allow the user to configure a color and/or a transparency of a representation on the graphical user interface of biological tissue corresponding to a selected field-of-view.

The method may include, in response to user input selecting a field-of-view corresponding to a biological tissue at the field-of-view selection component, rendering, on the graphical user interface, a first image of the selected field-of-view corresponding to the biological tissue. The method may include rendering, on the graphical user interface, a morphological analysis selection component allowing a user to select a morphological analysis of multiplexed biomarker image data corresponding to the selected field-of-view. The morphological analysis selection component may allow the user to configure a color and/or a transparency of a representation of a result of a selected morphological analysis.

The method may include, in response to user input selecting a first morphological analysis at the morphological analysis selection component, overlaying, on the first image of the biological tissue, a representation of a first result of the selected first morphological analysis. The first result of the first morphological analysis may indicate one or more morphological features of interest in the first image, wherein the first image of the biological tissue and the representation of the first result are displayed in a visually distinguishable manner.

The method may include, rendering, on the graphical user interface, a quality review selection component allowing the user to select a quality review score based on a comparison between the first image and the representation of the first result of the first morphological analysis rendered on the graphical user interface. In an exemplary embodiment, the method may include receiving a quality review score from the user, at the quality review selection component on the user interface, indicating one or more quality aspects of the first result of the first morphological analysis. In an exemplary embodiment, the method may include sending instructions to store, on a storage device, the quality review score in association with the multiplexed biomarker image data corresponding to the selected field-of-view of the biological tissue and the selected first morphological analysis. In an exemplary embodiment, the method may include storing, on a storage device, the quality review score in association with the multiplexed biomarker image data corresponding to the selected field-of-view of the biological tissue and the selected first morphological analysis.

In accordance with another exemplary embodiment, one or more non-transitory computer-readable media having encoded thereon one or more computer-executable instructions for performing a computer-implemented method are provided. The method is used for performing quality review of analysis of biological tissue. The method may include rendering a graphical user interface on a visual display device. The method may include rendering, on the graphical user interface, a field-of-view selection component allowing a user to select a field-of-view from a data set comprising tissue profile data including multiplexed biomarker images capturing expression of a plurality of biomarkers in a plurality of fields of view of biological tissue. The field-of-view selection component may allow the user to configure a color and/or a transparency of a representation on the graphical user interface of biological tissue corresponding to a selected field-of-view The method may include, in response to user input selecting a field-of-view corresponding to a biological tissue at the field-of-view selection component, rendering, on the graphical user interface, a first image of the selected field-of-view corresponding to the biological tissue. The method may include rendering, on the graphical user interface, a morphological analysis selection component allowing a user to select a morphological analysis of multiplexed biomarker image data corresponding to the selected field-of-view. The morphological analysis selection component may allow the user to configure a color and/or a transparency of a representation of a result of a selected morphological analysis.

The method may include, in response to user input selecting a first morphological analysis at the morphological analysis selection component, overlaying, on the first image of the biological tissue, a representation of a first result of the selected first morphological analysis. The first result of the first morphological analysis may indicate one or more morphological features of interest in the first image, wherein the first image of the biological tissue and the representation of the first result are displayed in a visually distinguishable manner.

The method may include, rendering, on the graphical user interface, a quality review selection component allowing the user to select a quality review score based on a comparison between the first image and the representation of the first result of the first morphological analysis rendered on the graphical user interface. In an exemplary embodiment, the method may include receiving a quality review score from the user, at the quality review selection component on the user interface, indicating one or more quality aspects of the first result of the first morphological analysis. In an exemplary embodiment, the method may include sending instructions to store, on a storage device, the quality review score in association with the multiplexed biomarker image data corresponding to the selected field-of-view of the biological tissue and the selected first morphological analysis. In an exemplary embodiment, the method may include storing, on a storage device, the quality review score in association with the multiplexed biomarker image data corresponding to the selected field-of-view of the biological tissue and the selected first morphological analysis.

In accordance with another exemplary embodiment, a computer system is provided for performing quality review of analysis of biological tissue. The system includes a visual display device, and a data storage device for storing a data set comprising tissue profile data including multiplexed biomarker images capturing expression of a plurality of biomarkers in a plurality of fields of view of biological tissue. The system also includes a computer processor coupled to the visual display device and the data storage device. The computer processor is programmed to render a graphical user interface on the visual display device, and to render, on the graphical user interface, a field of view selection component allowing a user to select a field of view from the data set stored on the data storage device, the field of view selection component allowing the user to configure a color and/or a transparency of a representation on the graphical user interface of biological tissue corresponding to a selected field of view.

The computer processor is also programmed to, in response to user input selecting a field of view corresponding to a biological tissue at the field of view selection component, render, on the graphical user interface, a first image of the selected field of view corresponding to the biological tissue. The computer processor is also programmed to render, on the graphical user interface, a morphological analysis selection component allowing a user to select a morphological analysis of multiplexed biomarker image data corresponding to the selected field of view, the morphological analysis selection component allowing the user to configure a color and/or a transparency of a representation of a result of a selected morphological analysis.

The computer processor is also programmed to, in response to user input selecting a first morphological analysis at the morphological analysis selection component, overlay, on the first image of the biological tissue, a representation of a first result of the selected first morphological analysis, the first result of the first morphological analysis indicating one or more morphological features of interest in the first image, wherein the first image of the biological tissue and the representation of the first result are displayed in a visually distinguishable manner. The computer processor is also programmed to render, on the graphical user interface, a quality review selection component allowing the user to select a quality review score based on a comparison between the first image and the representation of the first result of the first morphological analysis rendered on the graphical user interface. The computer processor may be programmed to execute any of the foregoing methods.

BRIEF DESCRIPTION OF THE DRAWINGS

The foregoing and other objects, aspects, features, and advantages of exemplary embodiments will become more apparent and may be better understood by referring to the following description taken in conjunction with the accompanying drawings, in which:

FIG. 34 is a block diagram showing an exemplary object-oriented class defined to represent cells.

DETAILED DESCRIPTION

Figure 1:
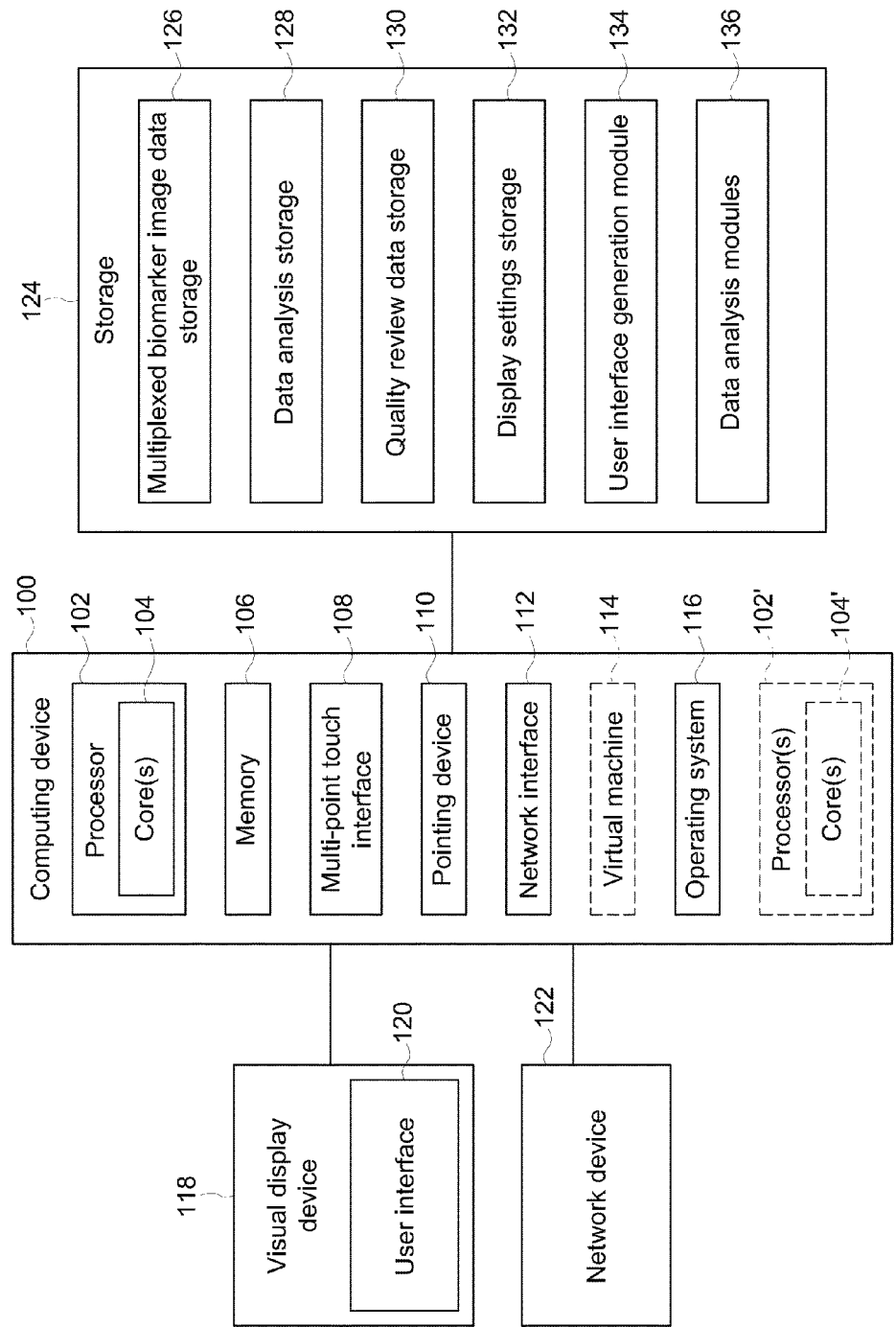
FIG. 1 is a block diagram of an exemplary computing device.

Embodiments disclosed herein include methods, systems, and devices for selectively displaying features of biological tissue, analyzing the tissue, and/or presenting analysis of tissue based on multiplexed biomarker image data. Exemplary embodiments enable structured, yet flexible and user-friendly, displays of selective features and/or analysis that allow pathologists to arrive at more objective and repeatable diagnoses and disease or condition models.

Embodiments taught herein leverage multiplexed biomarker images that are generated through known techniques, such as a staining-bleaching-restaining technique. The images illustrate the expression of biomarkers by individual cells within a larger tissue sample of cells. The individual cells are part of a larger tissue sample. The tissue sample may be a group of cells from a cell culture or a sample of an organ, a tumor, or a lesion. The tissue sample may also be part of a group of specimens of similar tissue from different subjects, known as a cohort. These groups of tissue samples may represent one or more disease or condition models, different stages within a disease or condition model, or one or more responses to treatment of a disease or condition.

Images of each stained field-of-view are generated through known techniques, such as with a digital camera coupled with an appropriate microscope and appropriate quality control routines. Automated image registration and analysis may also be used to quantify the biomarker concentration levels for individual delineated cells, or even sub-cellular compartments, such as nucleus, cytoplasm, and membrane. The data values resulting from the multiplexing and image analysis of cells may be stored alone or in conjunction with results of further analysis. A database may preserve the identity of the measurement of strength of the biomarker expression including the tissue and the location within the tissue from which it was drawn. The location may indicate the particular cell and/or tissue from which a particular measurement was drawn and may also include the compartment, nucleus, cytoplasm or membrane, associated with the measurement. The information may be stored in a database, which may be maintained in a storage device or in a network device.

Exemplary embodiments are described below with reference to the drawings. One of ordinary skill in the art will recognize that exemplary embodiments are not limited to the illustrative embodiments, and that components of exemplary systems, devices and methods are not limited to the illustrative embodiments described below.

Exemplary Computer Architecture

Systems and methods disclosed herein may include one or more programmable processing units having associated therewith executable instructions held on one or more computer readable medium, RAM, ROM, hard drive, and/or hardware. In exemplary embodiments, the hardware, firmware and/or executable code may be provided, for example, as upgrade module(s) for use in conjunction with existing infrastructure (for example, existing devices/processing units). Hardware may, for example, include components and/or logic circuitry for executing the embodiments taught herein as a computing process.

Displays and/or other feedback means may also be included, for example, for rendering a graphical user interface, according to the present disclosure. The display and/or other feedback means may be stand-alone equipment or may be included as one or more components/modules of the processing unit(s). In exemplary embodiments, the display and/or other feedback means may be used to simultaneously describe both morphological and statistical representations of a field-of-view of a biological tissue sample.

The actual software code or control hardware which may be used to implement some of the present embodiments is not intended to limit the scope of such embodiments. For example, certain aspects of the embodiments described herein may be implemented in code using any suitable programming language type such as, for example, assembly code, C, C# or C++ using, for example, conventional or object-oriented programming techniques. Such code is stored or held on any type of suitable non-transitory computer-readable medium or media such as, for example, a magnetic or optical storage medium.

As used herein, a "processor," "processing unit," "computer" or "computer system" may be, for example, a wireless or wire line variety of a microcomputer, minicomputer, server, mainframe, laptop, personal data assistant (PDA), wireless e-mail device (for example, "BlackBerry," "Android" or "Apple," trade-designated devices), cellular phone, pager, processor, fax machine, scanner, or any other programmable device configured to transmit and receive data over a network. Computer systems disclosed herein may include memory for storing certain software applications used in obtaining, processing and communicating data. It can be appreciated that such memory may be internal or external to the disclosed embodiments. The memory may also include non-transitory storage medium for storing software, including a hard disk, an optical disk, floppy disk, ROM (read only memory), RAM (random access memory), PROM (programmable ROM), EEPROM (electrically erasable PROM), flash memory storage devices, or the like.

FIG. 1 depicts a block diagram representing an exemplary computing device 100 that may be used to implement the systems and methods disclosed herein. The computing device 100 may be any computer system, such as a workstation, desktop computer, server, laptop, handheld computer, tablet computer (e.g., the iPad™ tablet computer), mobile computing or communication device (e.g., the iPhone™ mobile communication device, the Android™ mobile communication device, and the like), or other form of computing or telecommunications device that is capable of communication and that has sufficient processor power and memory capacity to perform the operations described herein. In exemplary embodiments, a distributed computational system may be provided comprising a plurality of such computing devices.

The computing device 100 includes one or more non-transitory computer-readable media having encoded thereon one or more computer-executable instructions or software for implementing the exemplary methods described herein. The non-transitory computer-readable media may include, but are not limited to, one or more types of hardware memory and other tangible media (for example, one or more magnetic storage disks, one or more optical disks, one or more USB flash drives), and the like. For example, memory 106 included in the computing device 100 may store computer-readable and computer-executable instructions or software for implementing a graphical user interface as described herein. The computing device 100 also includes processor 102 and associated core 104, and in some embodiments, one or more additional processor(s) 102' and associated core(s) 104' (for example, in the case of computer systems having multiple processors/cores), for executing computer-readable and computer-executable instructions or software stored in the memory 106 and other programs for controlling system hardware. Processor 102 and processor(s) 102' may each be a single core processor or a multiple core (104 and 104') processor.

Virtualization may be employed in the computing device 100 so that infrastructure and resources in the computing device may be shared dynamically. A virtual machine 114 may be provided to handle a process running on multiple processors so that the process appears to be using only one computing resource rather than multiple computing resources. Multiple virtual machines may also be used with one processor.

Memory 106 may include a computer system memory or random access memory, such as DRAM, SRAM, EDO RAM, and the like. Memory 106 may include other types of memory as well, or combinations thereof.

A user may interact with the computing device 100 through a visual display device 118, such as a screen or monitor, which may display one or more graphical user interfaces 120 provided in accordance with exemplary embodiments described herein. The visual display device 118 may also display other aspects, elements and/or information or data associated with exemplary embodiments. The computing device 100 may include other I/O devices for receiving input from a user, for example, a keyboard or any suitable multi-point touch interface 108, a pointing device 110 (e.g., a mouse, a user's finger interfacing directly with a display device, etc.). The keyboard 108 and the pointing device 110 may be coupled to the visual display device 118. The computing device 100 may include other suitable conventional I/O peripherals. The I/O devices may facilitate implementation of the one or more graphical user interfaces 120, for example, implement one or more selection components of a graphical user interface (e.g., field-of-view selection components, biomarker selection components, biomarker expression level criteria selection components, morphological feature selection components, etc.) for exemplary embodiments described herein.

The computing device 100 may include one or more storage devices 124, such as a durable disk storage (which may include any suitable optical or magnetic durable storage device, e.g., RAM, ROM, Flash, USB drive, or other semi-conductor-based storage medium), a hard-drive, CD-ROM, or other computer readable media, for storing data and computer-readable instructions and/or software that implement exemplary embodiments as taught herein. In exemplary embodiments, the one or more storage devices 124 may provide storage for data that may be generated by the systems and methods of the present disclosure. For example, a storage device 124 may provide storage for multiplexed biomarker image data 126, storage for data analysis 128 (e.g., storage for results of parameters for any of the image or statistical analyses described herein such as image segmentation results and clinical outcome correlations.), storage for quality review data 130 (e.g., quality indicators and validation information relating to any of the results of the image or statistical analyses described herein such as biomarker quality and image segmentation quality) and/or storage for display settings 132 (e.g., user preferences relating to colors, transparencies, etc.). The one or more storage devices 124 may further provide storage for computer readable instructions relating to one or more methods as described herein, including, for example, storage for computer readable instructions relating to the generation of a user interface 134 and storage for computer readable instructions relating to data analysis 136. The one or more storage devices 124 may be provided on the computing device 100 and/or provided separately or remotely from the computing device 100.

The computing device 100 may include a network interface 112 configured to interface via one or more network devices 122 with one or more networks, for example, Local Area Network (LAN), Wide Area Network (WAN) or the Internet through a variety of connections including, but not limited to, standard telephone lines, LAN or WAN links (for example, 802.11, T1, T3, 56 kb, X.25), broadband connections (for example, ISDN, Frame Relay, ATM), wireless connections, controller area network (CAN), or some combination of any or all of the above. The network interface 112 may include a built-in network adapter, network interface card, PCMCIA network card, card bus network adapter, wireless network adapter, USB network adapter, modem or any other device suitable for interfacing the computing device 100 to any type of network capable of communication and performing the operations described herein. The network device 122 may include one or more suitable devices for receiving and transmitting communications over the network including, but not limited to, one or more receivers, one or more transmitters, one or more transceivers, one or more antennae, and the like.

The computing device 100 may run any operating system 116, such as any of the versions of the Microsoft® Windows® operating systems, the different releases of the Unix and Linux operating systems, any version of the MacOS® for Macintosh computers, any embedded operating system, any real-time operating system, any open source operating system, any proprietary operating system, any operating systems for mobile computing devices, or any other operating system capable of running on the computing device and performing the operations described herein. In exemplary embodiments, the operating system 116 may be run in native mode or emulated mode. In an exemplary embodiment, the operating system 116 may be run on one or more cloud machine instances.

Figure 2:
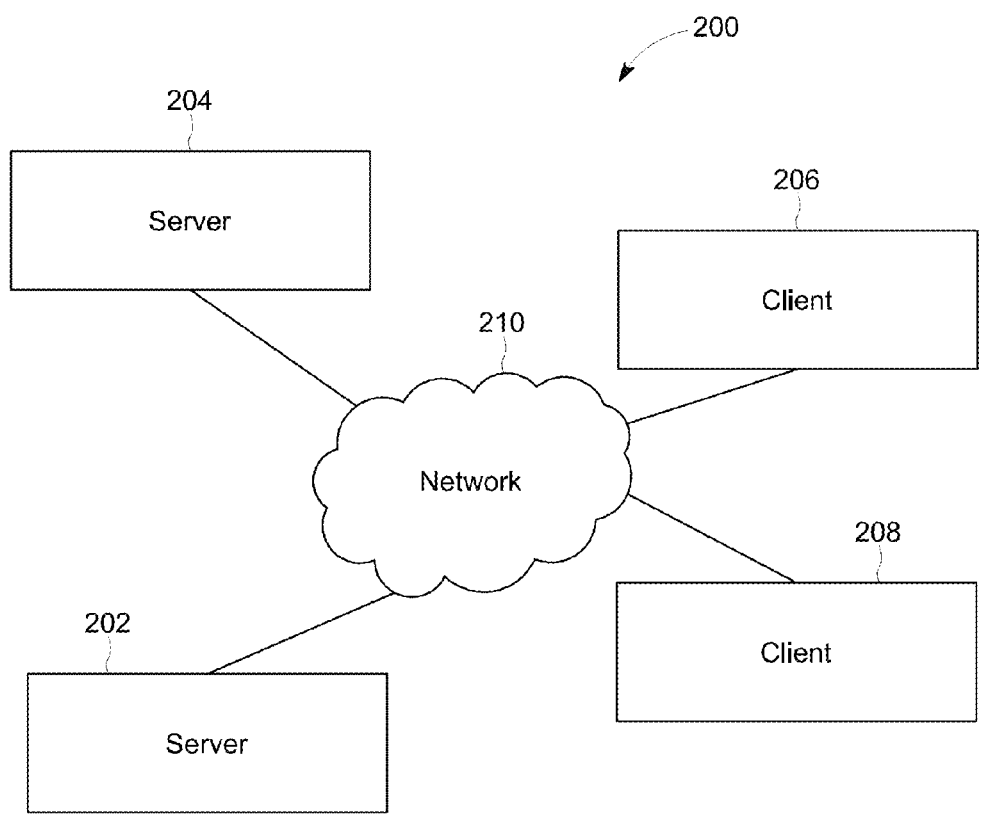
FIG. 2 is a block diagram of an exemplary network environment.

FIG. 2 depicts an exemplary network environment 200 suitable for implementation of embodiments disclosed herein in a way that enables and promotes collaboration. The network environment 200 may include one or more servers 202 and 204 coupled to one or more clients 206 and 208 via a communication network 210. Notably, each of the one or more servers 202 and 204 and one or more clients 206 and 208 may be implemented as a computing device 100 as described with respect to FIG. 1. Thus, each of the one or more servers 202 and 204 and the one or more clients 206 and 208 may include a network interface 112 and a network device 122 to enable the servers 202 and 204 to communicate with the clients 206 and 208 via the communication network 210. The communication network 210 may include, but is not limited to, the Internet, an intranet, a LAN (Local Area Network), a WAN (Wide Area Network), a MAN (Metropolitan Area Network), a wireless network, an optical network, and the like. The communication facilities provided by the communication network 210 are capable of supporting collaborative analysis and research efforts as disclosed herein.

In exemplary embodiments, collaborative entities may utilize the one or more clients 206, 208 to remotely access the one or more servers 202, 204. The servers 202 and 204 may advantageously provide a cloud environment for storing, accessing, sharing and analyzing (for example, validating) data related to the systems and methods of the present disclosure. The one or more servers 206, 208 may also advantageously be associated with one or more applications characterized, for example, by computer-readable instructions for implementing one or more modules relating to the generation of a user interface and/or data analysis, as described herein. The one or more applications may be advantageously be accessed and run remotely on the one or more clients 206 and 208. In exemplary embodiments, distribution of the one or more applications may be subject to a particular condition, such as a license agreement.

Exemplary Selection and Display of Multiplexed Images of Biological Tissue

Exemplary embodiments may provide one or more graphical user interfaces that allow a user to selectively view and manipulate image and/or text data relating to one or more fields-of-view of biological tissue. Exemplary biological tissue images may include images of morphological features of the tissue, expression levels of biomarkers in the tissue, expression and non-expression of DNA sequences in the tissue, and the like. Exemplary graphical user interfaces allow users to review complex image and analysis data corresponding to multiple patients, multiple tissue fields-of-view and/or multiple biomarker data in a structured yet flexible and user-friendly manner. Exemplary embodiments also provide time-efficient and streamlined methods of retrieving data for display and analysis.

Exemplary embodiments enable a user to select, directly on a user interface, a field-of-view of biological tissue for display on the user interface. The ability to select particular studies/experiments, slides, spots and biomarkers using the tools provided on the user interface makes it unnecessary for a user to remember the locations of the files related to the studies/experiments, slides, spots and biomarkers, and allows the user to select data sources in an intuitive, time-efficient and user-friendly manner.

Exemplary embodiments also enable a user to select, directly on the user interface, one or more biomarkers whose expression levels are to be displayed on the user interface, and one or more corresponding colors for the biomarkers. In response, the user interface displays expression levels of the selected biomarkers in an overlaid manner for the selected field-of-view of biological tissue, so that the expression levels of each biomarker are displayed as intensity levels of a corresponding selected color. Any number of biomarkers may be selected for concurrent display of their expression levels in an overlaid manner on the image of a selected field-of-view. Selectable numbers of biomarkers include, but are not limited to, 1, 2, 3, 4, 5, 6, 7, 8, 9, 10, 11, 12, 13, 14, 15, 16, 17, 18, 19, and 20. Display of the expression levels of a plurality of biomarkers in the same field-of-view display allows the user to obtain a full picture of the structural and functional aspects of the biological tissue and allows the user to assess co-localizations of the different biomarkers in the biological tissue.

Similarly, exemplary embodiments may also enable a user to select one or more DNA sequences whose expression and non-expression are to be displayed on the user interface, and one or more corresponding colors for the DNA sequences. In response, the user interface displays expression and non-expression of the selected DNA sequences in an overlaid manner for the selected field-of-view of biological tissue, so that the expression and non-expression of each DNA sequence are displayed in one or more corresponding selected colors. In an exemplary image of a field-of-view, expression of one or more DNA sequences and expression levels of one or more biomarkers may be displayed in an overlaid manner. Any number of DNA sequences may be selected for concurrent display of their expression or non-expression in an overlaid manner on the image of a selected field-of-view. Selectable numbers of DNA sequences include, but are not limited to, 1, 2, 3, 4, 5, 6, 7, 8, 9, 10, 11, 12, 13, 14, 15, 16, 17, 18, 19, and 20.

Figure 3:
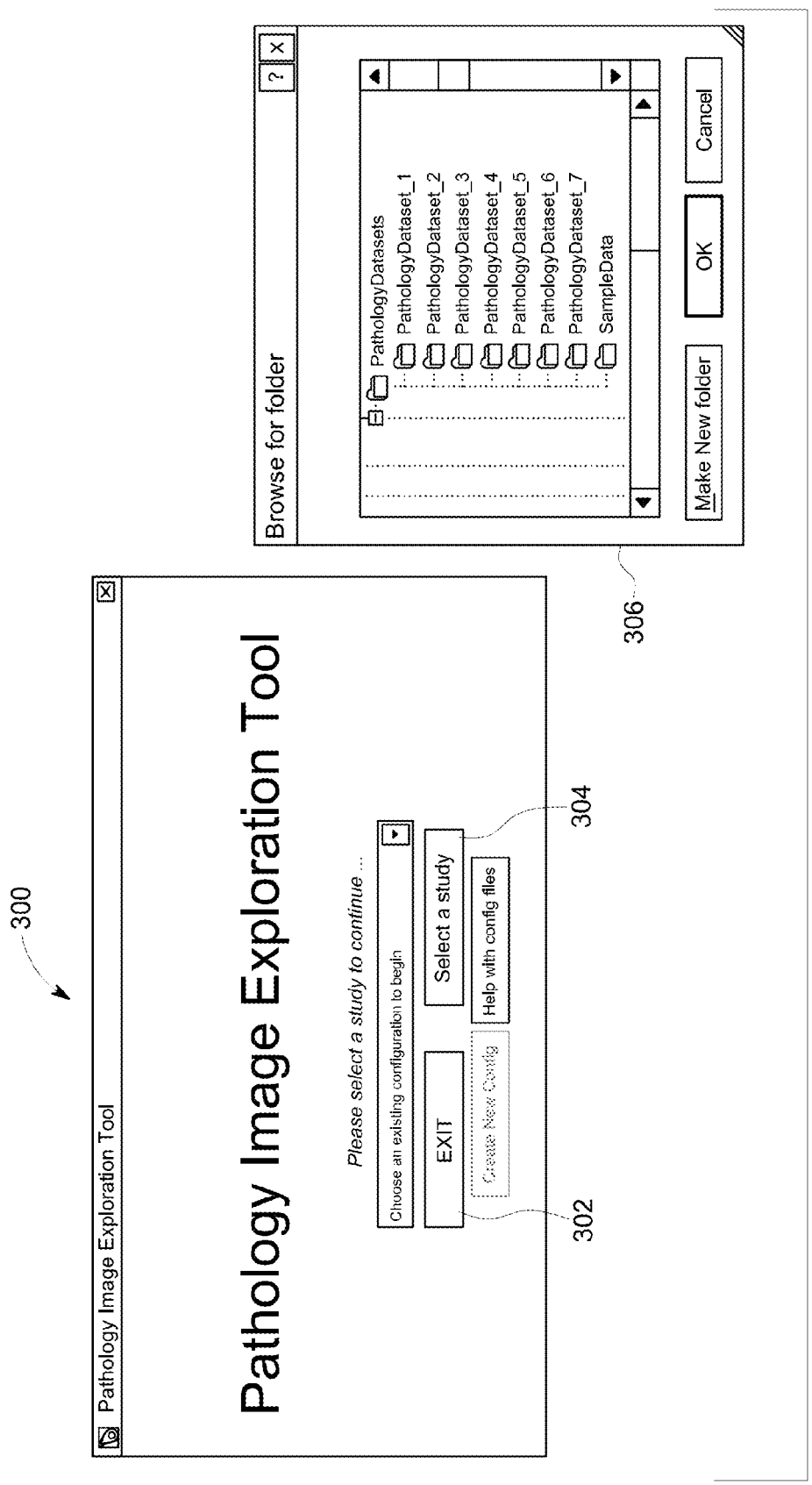
FIG. 3 illustrates an exemplary user interface that may be used to select sources of data corresponding to biological tissue.

FIGS. 3-13 illustrate an exemplary graphical user interface, although other suitable user interfaces may be used. As illustrated in FIG. 3, an exemplary user interface 300 may display an exit component 302 to allow a user to exit and close the user interface at the start of a session. In an exemplary embodiment, the exit component 302 may continue to be displayed on the user interface as the session continues. The user interface 300 may concurrently display a data source selection component 304 to enable a user to directly select one or more sources of image and/or text data for display on the user interface. The data source selection component 304 may allow a user to select a particular study or experiment. In an exemplary embodiment, a file structure browser 306 may be displayed to allow the user to view a file structure in which data files are organized. The file structure browser 306 may allow the user to select one or more topmost level directories that include all of the image and/or text data corresponding to a study. In an exemplary embodiment, a default data source may be automatically selected if the user fails to make a selection.

Figure 4:
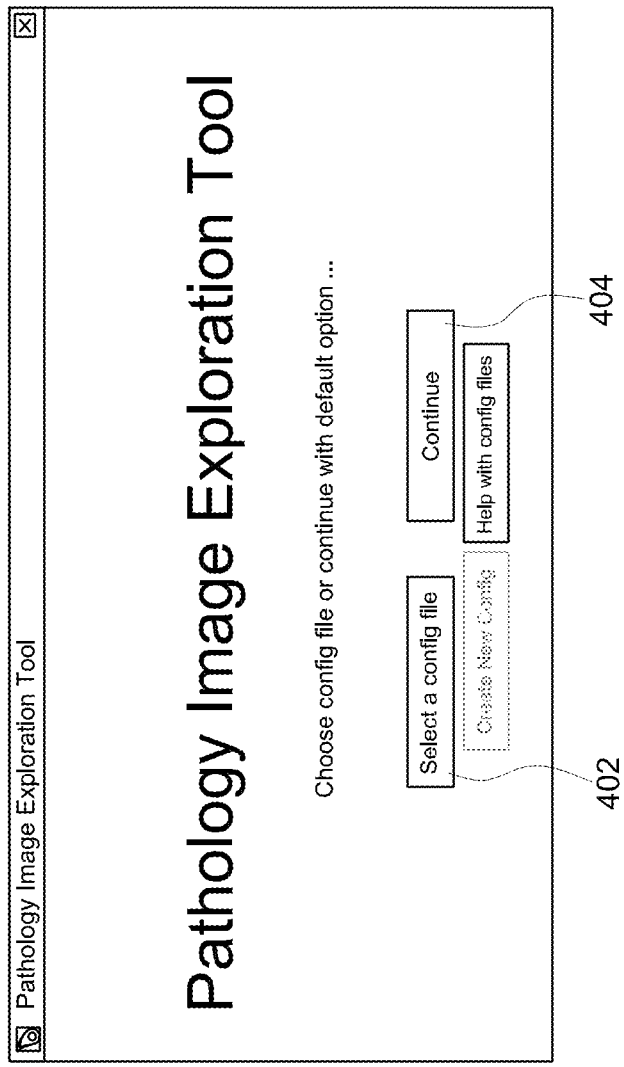
FIG. 4 illustrates an exemplary user interface that may be used to select a configuration file containing information on the source of image and/or statistical information.

As illustrated in FIG. 4, upon selection of a study or experiment, the user interface may display a configuration selection component 402 that allows a user to select a configuration file that includes options for configuring the sources and types of data that are to be displayed in the user interface. For example, an exemplary configuration file may be used to specify the pathname to a folder or file containing biological image and/or statistical data, user-defined inputs (for example, results, analysis methods, clustering options, biomarkers, slides/fields-of-view, and the like, to be viewed on the user interface), and the like. The user interface may concurrently display a continue component 404 that may allow the user to continue with a default configuration file without having to select a particular configuration file.

Figure 5:
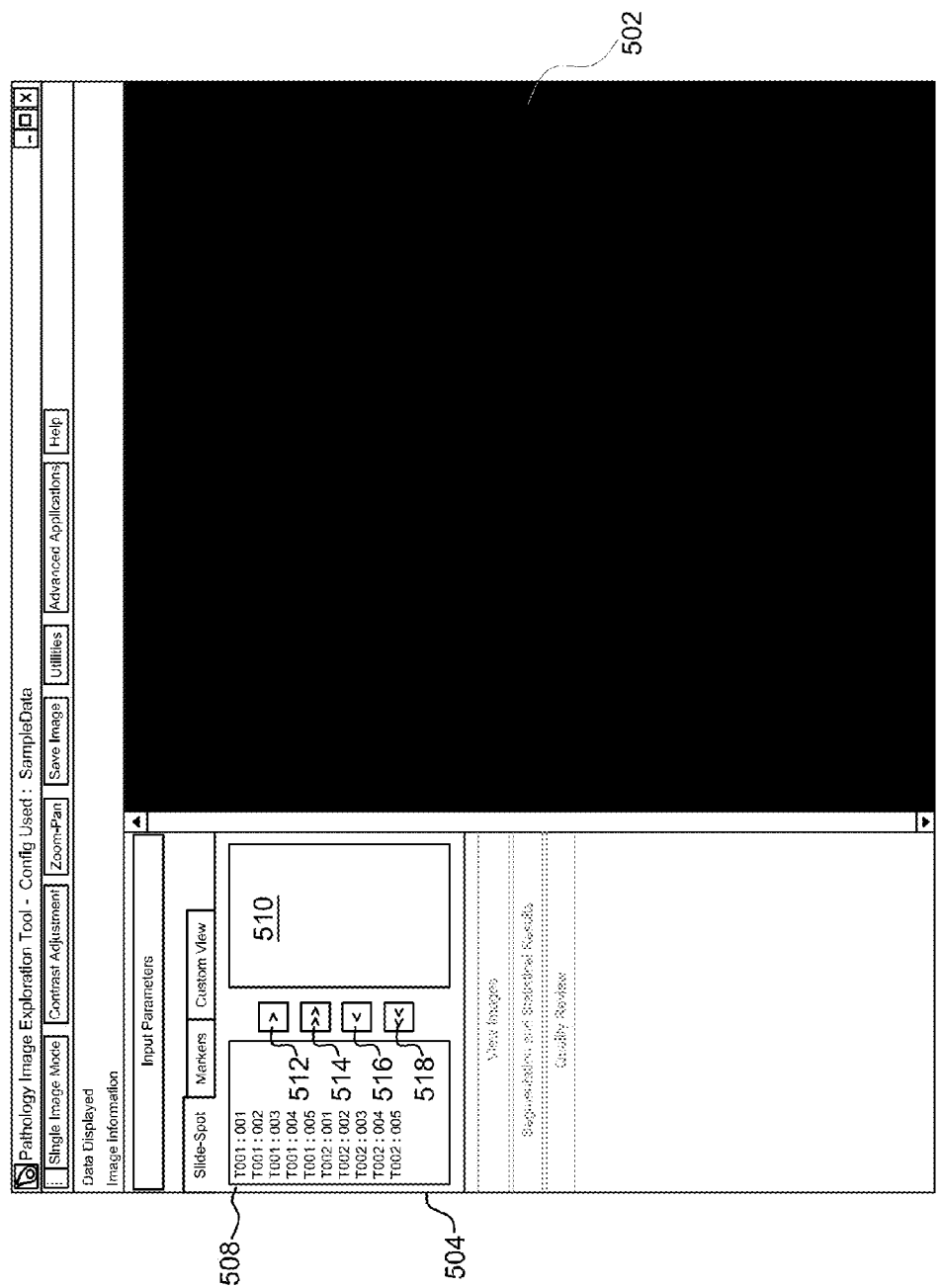
FIG. 5 illustrates an exemplary user interface that may be used to select slides and spots for display

As illustrated in FIG. 5, upon selection of a configuration file, the user interface may provide a display panel 502 in which image and/or text data corresponding to a field-of-view of biological tissue may be rendered. The user interface may also display a slide-spot selection component 504 that may allow a user to select data corresponding to one or more slides and one or more spots in the selected study or experiment. The slide-spot selection component 504 may include a slide-spot browser tool 508 that lists combinations of slides-spots in the selected study or experiment. A user may select one or more slide-spot combinations directly in the slide-spot selection component 508 and add the selected combinations to a selected slide-spot tool 510. In an exemplary embodiment, the user may use a pointing device, e.g., a mouse, to click on one or more slide-spot combinations or may use a keyboard shortcut to, e.g., holding down the "Shift" or "Ctrl" keys, to select multiple combinations at a time.

The combination of the slide-spot browser tool 508 and the selected slide-spot tool 510 allows the user to easily revise his/her slide-spot selections. For example, an "add selected slide-spot" tool 512 may allow the user to add one or more selected slide-spot combinations in the slide-spot browser tool 508 to the selected slide-spot tool 510. An "add all slide-spots" tool 514 may allow the user to add all of the slide-spot combinations in the slide-spot browser tool 508 to the selected slide-spot tool 510. A "remove selected slide-spot" tool 516 may allow the user to remove one or more selected slide-spot combinations from the selected slide-spot tool 510. A "remove all slide-spots" tool 518 may allow the user to remove all of the slide-spot combinations from the selected slide-spot tool 510.

Figure 6:
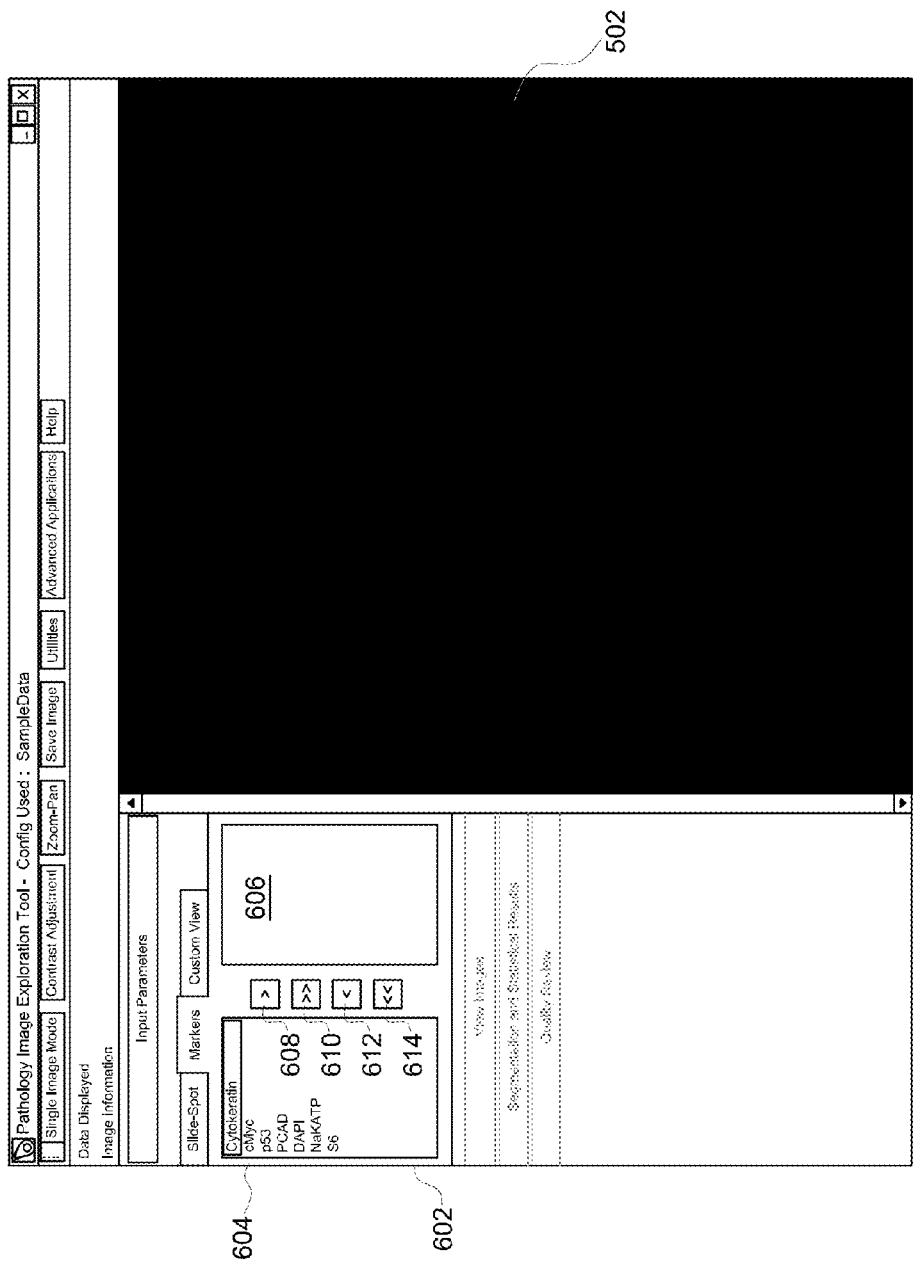
FIG. 6 illustrates an exemplary user interface that may be used to select biomarkers for display.

As illustrated in FIG. 6, the user interface may provide a marker selection component 602 to allow the user to select one or more markers whose expression levels are to be rendered on an image of the selected slide-spot. The marker selection component 602 may include a marker browser tool 604 that lists markers whose expression levels may be represented in the selected slide-spot. A user may select one or more markers directly in the marker selection component 604 and add the selected markers to a selected marker tool 606. In an exemplary embodiment, the user may use a pointing device, e.g., a mouse, to click on one or more markers or may use a keyboard shortcut to, e.g., holding down the "Shift" or "Ctrl" keys, to select multiple combinations at a time.

The combination of the marker browser tool 604 and the selected marker tool 606 allows the user to easily revise his/her marker selections. For example, an "add selected marker" tool 608 may allow the user to add one or more selected markers in the marker browser tool 604 to the selected marker tool 606. An "add all markers" tool 610 may allow the user to add all of the markers in the marker browser tool 604 to the selected marker tool 606. A "remove selected marker" tool 612 may allow the user to remove one or more selected marker from the selected marker tool 606. A "remove all markers" tool 614 may allow the user to remove all of the markers from the selected marker tool 606.

In response to the selection of one or more markers, the user interface may render, in the display panel 502, the expression levels of the selected markers in the selected slide-spot of the selected study or experiment. In an exemplary embodiment, the expression levels of a marker may be represented as a continuous range of intensities of a user-selected color. In another exemplary embodiment, the expression levels of a marker may be represented as a continuous range of two or more user-selected colors. In another exemplary embodiment, the expression levels of a marker may be represented as a first user-selected color for high expression levels (i.e., expression levels above a predefined user-selected level) and as a second user-selected color for low expression levels (i.e., expression levels below a predefined user-selected level).

The expression levels of different markers may be represented in different colors or color combinations. When two or more markers are selected for display in the display panel 502, exemplary embodiments may generate a composite overlaid image in which the colors representing expression levels of the different markers are blended, such that the expression levels of each marker has a contribution to the blended colors. In an exemplary embodiment, each pixel in the composite overlaid image may have a blended color that represents contributions of the expression levels of the selected markers. In another exemplary embodiment, each biological unit (e.g., cell) may have a blended color that represents contributions of the expression levels of the selected markers. In an exemplary embodiment, each selected marker may have an equal contribution in the composite overlaid image, for example, so that the expression levels of each marker show similar or identical brightness. Exemplary embodiments may allow a user to configure and adjust the contribution of one or more selected markers in a composite overlaid image, for example, by reducing the brightness of the colors associated with a marker to decrease the contribution of the marker.

The ability to select data using the data source selection component, the slide-spot browser tool and the marker selection component in the user interface allows intuitive, time-efficient and user-friendly selection of data sources. In particular, the ability to select particular studies/experiments, slides, spots and biomarkers using the tools provided in the data source selection component makes it unnecessary for a user to remember the locations of the files related to the studies/experiments, slides, spots and biomarkers. In contrast, certain conventional systems of displaying biological tissue data require a user to navigate a file structure to select data sources for display.

Figure 7:
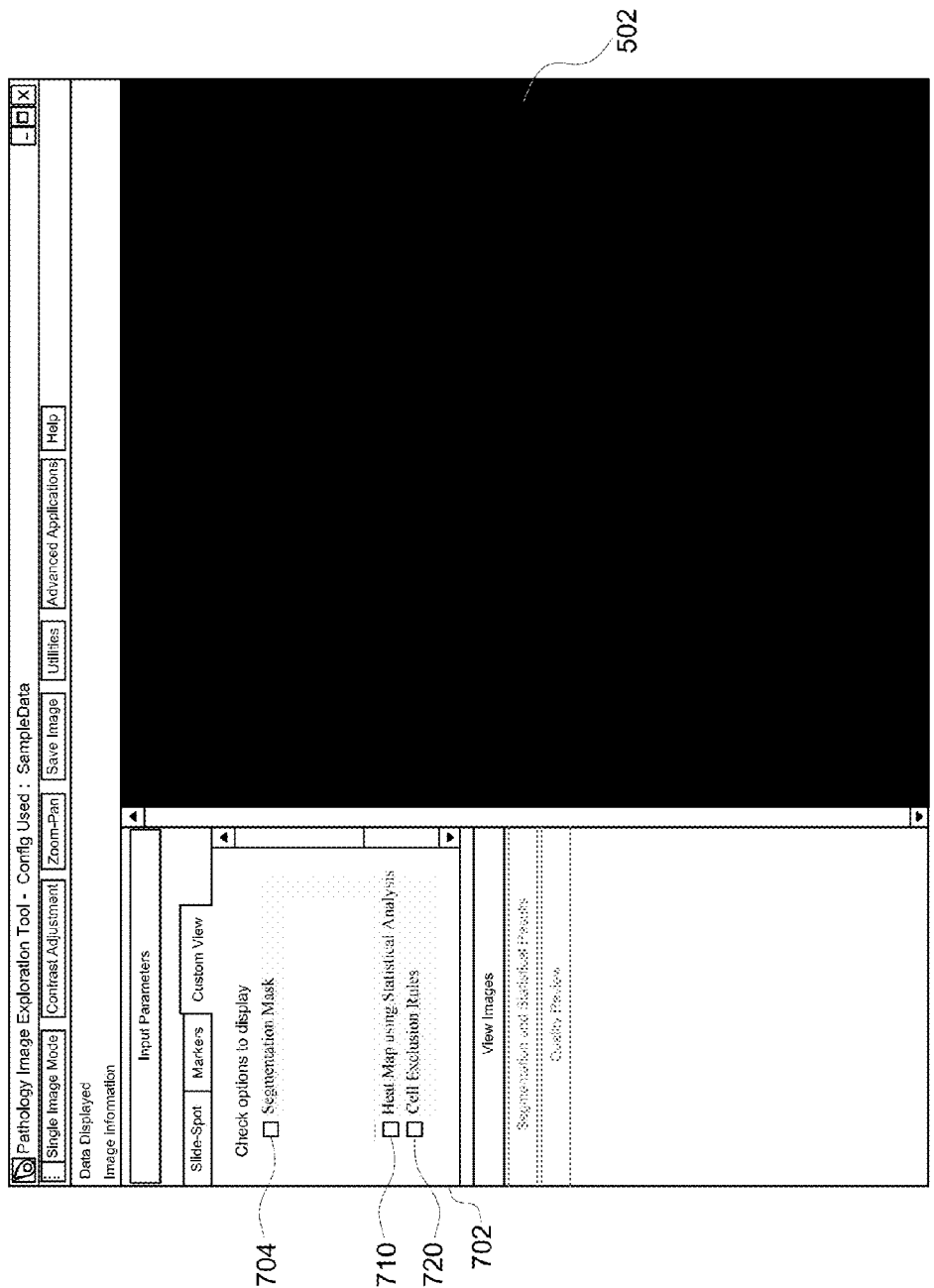
FIG. 7 illustrates an exemplary user interface that may be used to select analysis results for display.

As illustrated in FIG. 7, the user interface may display an analysis selection component 702 to allow a user to select results of one or more analysis methods for display. Exemplary analysis methods may include, but are not limited to, image segmentation 704 (that delineates biological units), heat map 710 (that displays expression levels of markers or results of statistical analysis on a cell-by-cell basis), cell exclusion 720 (that indicates cells having one or more selected morphological characteristics), and the like.

Figure 8:
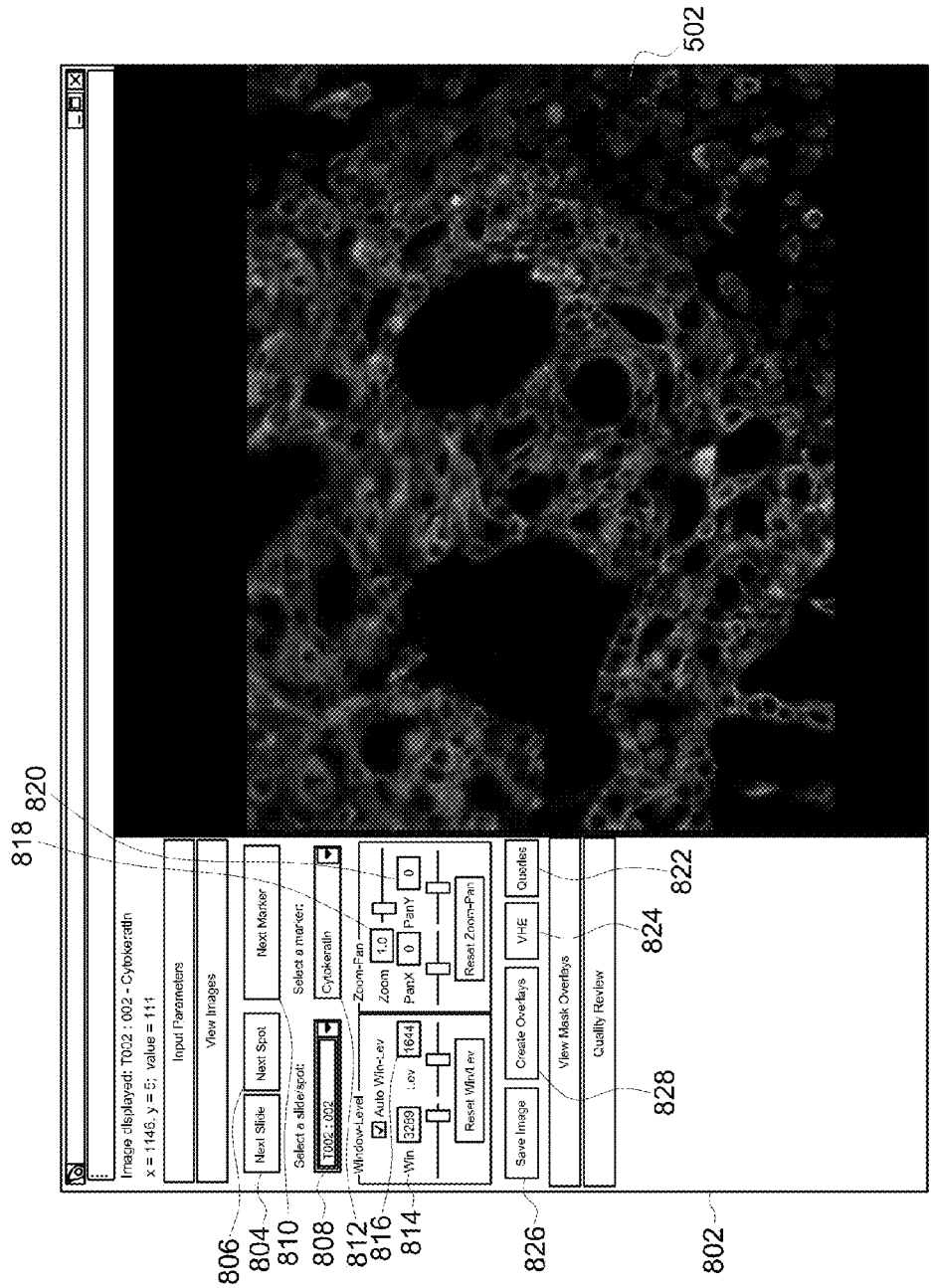
FIG. 8 illustrates an exemplary user interface for display of expression of markers and DNA sequences.

As illustrated in FIG. 8, while image and/or text data corresponding to a selected slide-spot is displayed in the display panel 502, the user interface may concurrently display a selection panel 802 adjacent to the display panel 502 to allow the user to make adjustments to the display in the display panel. In an exemplary embodiment, a "Next Slide" component 804 may allow a user to display expression levels of the currently selected biomarker in the first spot of the next slide. A "Next Spot" component 806 may allow a user to display expression levels of the currently selected biomarker in the next spot of the currently selected slide. A "Slide/Spot Selection" component 808 may allow a user to select particular slide-spot combinations available for the selected study or experiment.

The selection panel 802 may also include one or more options to display expression levels of a different marker in the same slide and spot than the currently displayed marker. For example, a user may choose to transition from viewing expression levels of biomarker NaKATP to expression levels of biomarker cytokeratin in the image of the same field-of-view. In an exemplary embodiment, a "Next Marker" component 810 may allow a user to display expression levels of a different biomarker in the same slide and spot displayed in the display panel 502. A "Marker Selection" component 812 may allow a user to select a particular marker, e.g., cytokeratin, to display expression levels of the selected marker in the display panel 502.

The selection panel 802 may include one or more options for manipulating aspects of the display in the display panel 502 including, but not limited to, magnification, brightness, contrast, and the like. The contribution of a particular marker in an overlaid image of multiple markers may be adjusted to increase or decrease the contribution of the expression levels of the marker in the image. For example, contrast and brightness may be adjusted to enhance the expression levels represented in a "dim" marker or to suppress "over-exposed" regions in images. The adjusted contrast and brightness levels (rather than the original levels) may be used in generating a blended composite image when multiple images are overlaid.

The selection panel 802 may enable setting and changing the contrast and brightness of an image displayed in the display panel 502. The ability to change the contrast and brightness allows a user to enhance certain features in the image to facilitate interpretation. The ability to change the contrast and brightness also enables adequate display of the image on a selected display device. For example, if the gray scale dynamic range of an image (i.e., the range between minimum and maximum pixel values in the image) is larger than the range that can be handled by a selected display device, the gray scale range of the image may be down-scaled in an appropriate manner to allow the device to display the image correctly. In another example, in the multiplexed marker images of exemplary embodiments, an image may be represented by 12-16 bits of information, while a typical display device may handle only 8 bits of information. In this case, only a small "window" of image values (between the maximum and minimum of the image values) may be displayed by the device.

Figure 40:
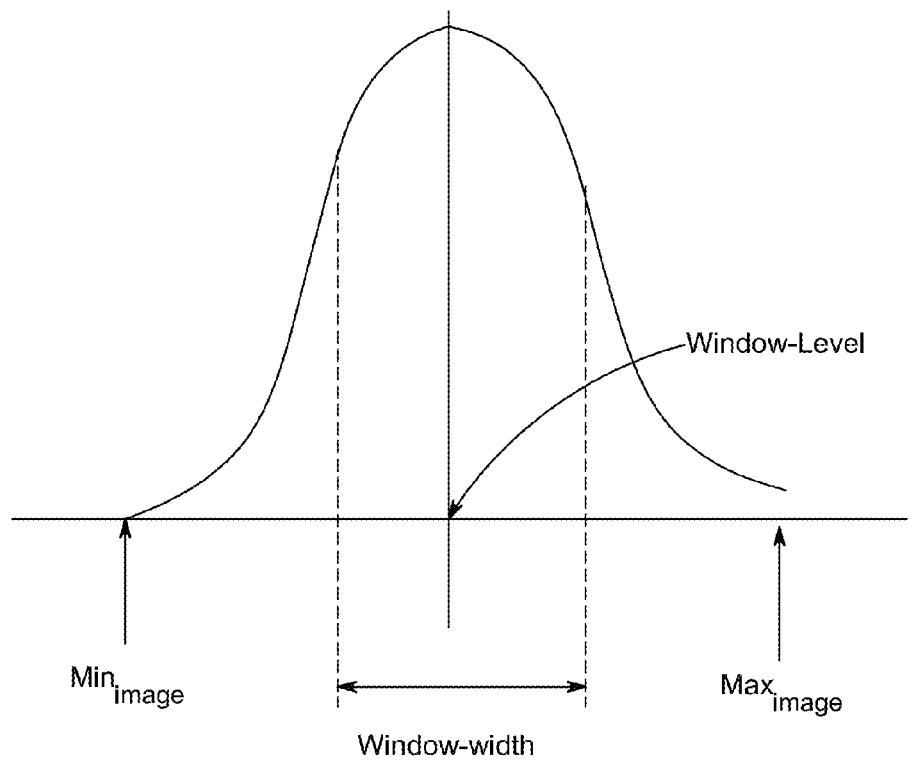
FIG. 40 is a graph showing the "window width" and "window level" on a histogram of gray scale values.

A "window level" is defined as gray scale that is the central value of the window and "window width" is defined as the range of gray scale values around the window level that will be included in the display. Typically, the "window width"

represents a linear range so that half of the window width occurs on the left side of the selected window level and the other half of the window width occurs on the right side. FIG. 40 is a graph showing the "window width" and "window level" on a histogram of gray scale values. Upon configuration of the "window width" value, the new minimum and maximum gray scale values for the displayed image are redefined by the window width. The gray scale values that lie between the new minimum and maximum gray scale values are modified to fit within an 8-bit range, in an exemplary embodiment. That is, the new minimum is set to zero, the new maximum is set to 255, and all values in between are distributed according to a specified function, such as linear interpolation.

In an exemplary embodiment, the selection panel 802 may include a "Window Width" component 814 for allowing a user to set the contrast of the display in the display panel 502. The contrast of the display increases with a decrease in the window width, and decreases with an increase in the window width. The "Window Width" component 814 may include an "Auto Window Width" tool that automatically sets the contrast to a default level. The "Window Width" component 814 may include a "Window Width Input" tool that may allow a user to input a particular level of contrast. The "Window Width" component 814 may include a "Window Width Slider" tool that may allow a user to select a relative level of contrast using a slider. The "Window Width" component 814 may also include a "Window Width Reset" tool to allow a user to reset the contrast level to a default level.

In an exemplary embodiment, the selection panel 802 may include a "Window Level" component 816 for allowing a user to set the brightness of the display in the display panel 502. The brightness of the display increases as the window level is moved toward the maximum gray scale value in the image, and decreases as the window level is moved toward the minimum gray scale value in the image. The "Window Level" component 816 may include an "Auto Window Level" tool that automatically sets the brightness to a default level. The "Window Level" component 816 may include a "Window Level Input" tool that may allow a user to input a particular level of brightness. The "Window Level" component 816 may include a "Window Level Slider" tool that may allow a user to select a relative level of brightness using a slider. The "Window Level" component 816 may also include a "Window Level Reset" tool to allow a user to reset the brightness level to a default level.

Since the "Window Level" component 816 allows a user to discard gray scale values that are too high, i.e., very bright pixels, this enables filtering out pixels generated by noise and/or dust that are typically very bright. In this case, the window level may be selected such that the bright pixels values associated with noise and/or dust fall to the right of the selected window level, and are thereby excluded from the adjusted image.

In an exemplary embodiment, the selection panel 802 may include a "Zoom Input" tool 818 for allowing a user to input a particular level of zoom, or a relative level of zoom using a slider. The zoom level may be reset to a default level. In some exemplary embodiments, the user interface may allow zooming in and out using a pointing device, for example, by clicking the right button on a mouse. In some exemplary embodiments, the user interface may allow zooming in and out using keyboard shortcuts, for example, using a combination of the "Ctrl" key and the "+" key to zoom in and using a combination of the "Ctrl" key and the "-" key to zoom out.

In an exemplary embodiment, the selection panel 802 may include a "Pan Input" tool 820 for allowing a user to input a particular level of panning constrained to the x or y-axis in the display panel 502, or a relative level of panning constrained to the x or y-axis using a slider. The pan settings may be reset to display the initially displayed field-of-view in the display panel 502. In some exemplary embodiments, the user interface may allow panning using a pointing device, for example, by clicking the left button on a mouse. In some exemplary embodiments, the user interface may allow panning using keyboard shortcuts.

In an exemplary embodiment, the selection panel 802 may include a "Biological Unit Query" component 822 for allowing a user to selectively display a set of biological units in the display panel 502 that satisfy one or more criteria. Exemplary biological units may include, but are not limited to, cells, clusters of cells, nuclei, and the like. Exemplary criteria selectable using the "Biological Unit Query" may include, but are not limited to, maximum and/or minimum expression levels of one or more markers, expression or non-expression of one or more DNA sequences, morphological characteristics (e.g., maximum and/or minimum cell size, maximum and/or nucleus size), and the like. Selection of one or more criteria may cause only those biological units that satisfy the criteria to be displayed or to be highlighted in the display panel 502. Conversely, selection of one or more criteria may cause those biological units that do not satisfy the criteria to be displayed or to be highlighted in the display panel 502.

Figure 9:
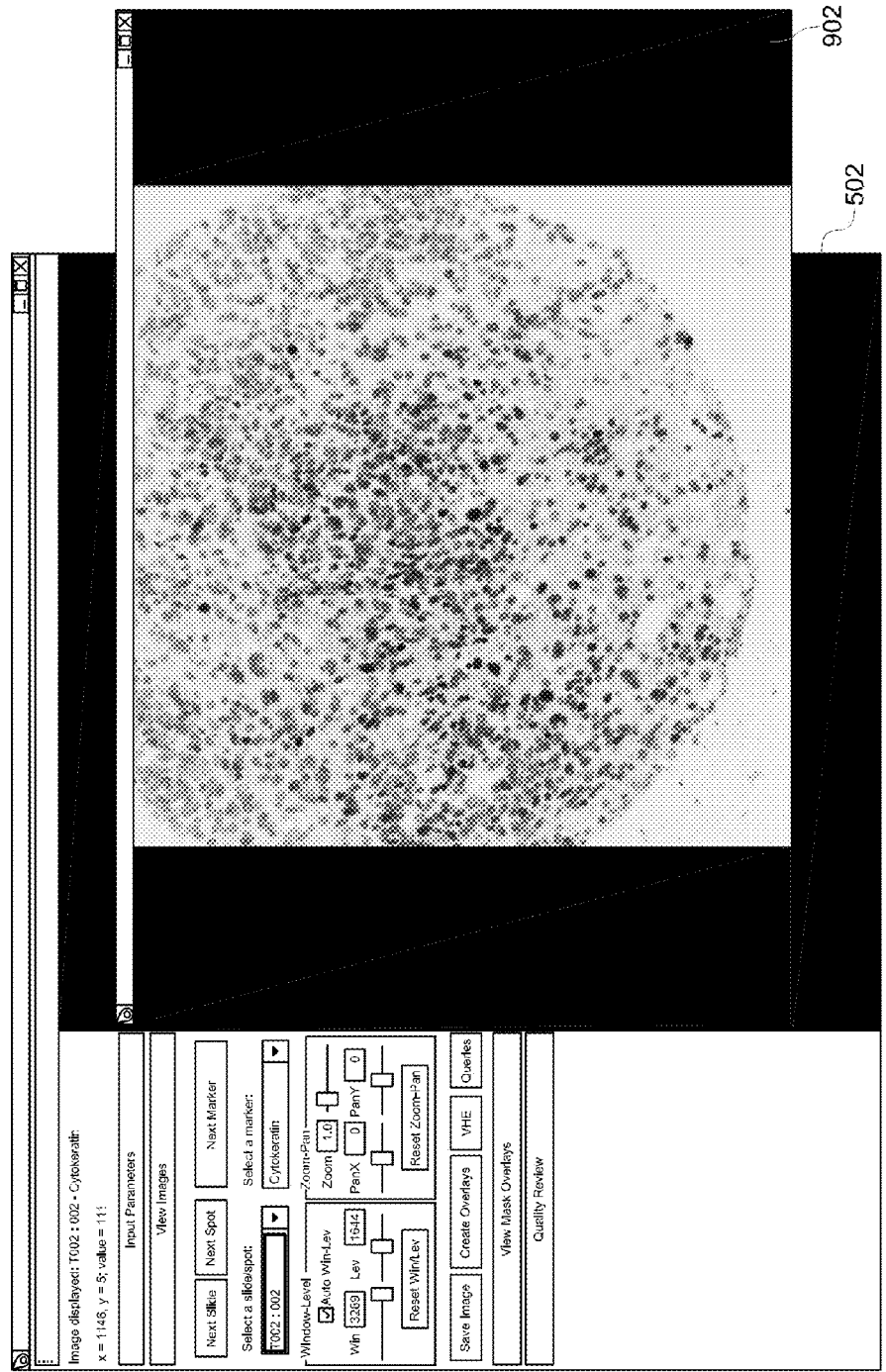
FIG. 9 illustrates an exemplary user interface showing a computer-generated image of biological tissue in which one or more images acquired from the tissue are mapped to a new color space to generate, for example, an H&E type image.

In an exemplary embodiment, the selection panel 802 may include a "VHE" component 824 that, when selected, displays a computer-generated image of the selected field-of-view of biological tissue in which one or more images acquired from the tissue are mapped to a new color space to generate, for example, a Hematoxylin and Eosin (H&E) type image. In an exemplary embodiment, the VHE image may be used as the baseline image of the biological tissue with respect to which other markers, DNA sequences, and morphological characteristics may be overlaid, compared, and/or assessed. FIG. 9 illustrates an exemplary separate display panel 902 displaying an exemplary VHE image of a selected field-of-view of biological tissue. Computer generation of H&E type images is described in U.S. Patent Publication No. 2011-0074944 A1 titled "System and Methods for Generating a Brightfield Image using Fluorescent Images," published Mar. 31, 2011.

The selection panel 802 may include a "Save Image" component 826 for allowing a user to save the image displayed in the display panel 502 in a database or storage device. Exemplary formats for the saved image may include, but are not limited to, jpg files, png files, and the like.

The selection panel 802 may include a "Create Overlay" component 828 for allowing a user to create one or more image overlays of renderings in the display panel 502. As one example, an overlay may be a rendering of a field-of-view of biological tissue in which the expression levels of a particular marker are represented in intensities of a particular color. As another example, an overlay may be a rendering of a field-of-view of biological tissue in which the expression or non-expression of a particular DNA sequence is represented in two respective colors. Image data corresponding to the expression and non-expression of DNA sequences may be obtained using fluorescence in situ hybridization (FISH).

The overlaying of a plurality of such renderings allows generation of a blended composite image in the display panel 502 that allows a user to assess co-localizations and correlations among markers, DNA sequences, and the like. In an exemplary embodiment, the blended composite image may be generated as a single layer in which colors of the different overlaid images are merged. The contribution of each biomarker or DNA sequence in the blended composite image may be adjusted to determine the extent to which the biomarker or DNA sequence contributes to the final color image.

Any number of biomarkers may be selected for concurrent display of their expression levels in an overlaid manner on the image of a selected field-of-view. Selectable numbers of biomarkers include, but are not limited to, 1, 2, 3, 4, 5, 6, 7, 8, 9, 10, 11, 12, 13, 14, 15, 16, 17, 18, 19, and 20. Expression levels of different biomarkers may be represented using intensities of different colors in an exemplary embodiment.

Figure 10:
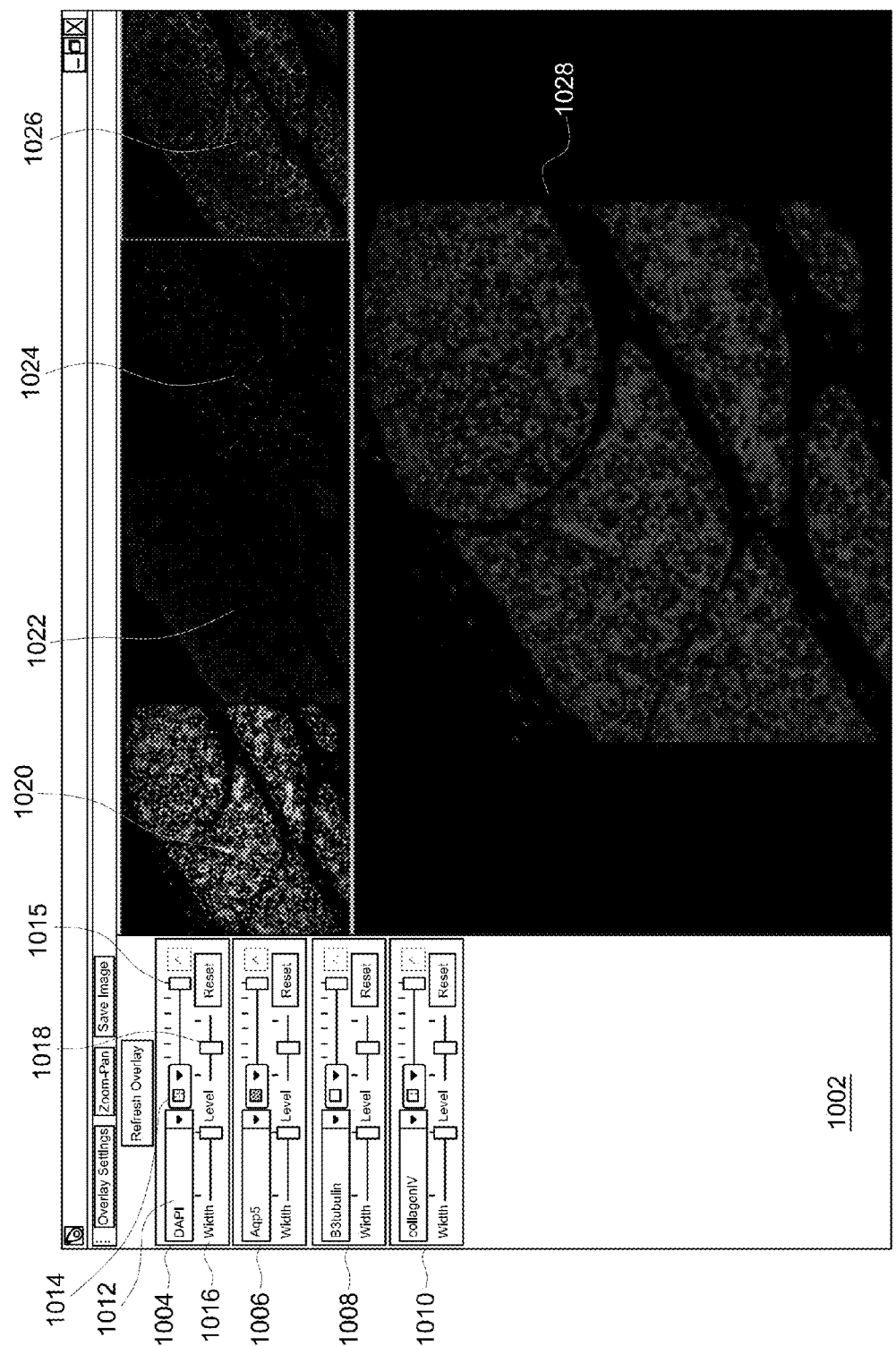
FIG. 10 illustrates an exemplary user interface showing selection of four biomarkers for overlaid display.

Upon selection of the "Create Overlay" component 828, the user interface may present a separate "Overlay Selection" panel 1002, as illustrated in FIG. 10, for allowing a user to select one or more biomarkers and/or one or more DNA sequences, whose expressions will be overlaid in the display panel 502. As illustrated in FIG. 10, the "Overlay Selection" panel 1002 may include a separate component for each biomarker or DNA sequence being selected. For example, components 1004, 1006, 1008, and 1010 may be provided for selecting biomarkers Cytokeratin, DAPI, NaKATP and S6, respectively.

Each component may include a "Marker/DNA Selection" tool 1012 for allowing a user to select a particular marker or DNA sequence whose expression will be rendered in the display panel. Each component may include a "Display/Hide" tool for allowing a user to display or hide a respective component.

Each component 1004, 1006, 1008, and 1010 may include a "Color Selection" tool 1014 for allowing a user to select a color using which expression of a marker or DNA sequence will be displayed in the display panel. For example, a user may choose to render expression levels of the markers Cytokeratin, DAPI, NaKATP and S6 in red, green, blue and pink, respectively. The "Contrast/Brightness Selection" tool and the "Color Selection" tool enhance user experience by allowing the user to control and customize the overlaid displays in the display panel.

Each component 1004, 1006, 1008, and 1010 may include a "Contribution Selection" tool (for example, a slider) 1015 associated with the "Color Selection" tool for allowing a user to select the contribution of each marker or DNA sequence to the overall overlaid image rendered in the display panel. In an exemplary embodiment, each pixel in the composite overlaid image may have a blended color that represents contributions of the expression levels of the selected markers. In another exemplary embodiment, each biological unit (e.g., cell) may have a blended color that represents contributions of the expression levels of the selected markers. Exemplary embodiments may allow a user to configure and adjust the contribution of one or more selected markers in a composite overlaid image, for example, by reducing the brightness of the colors associated with a marker to decrease the contribution of the marker.

Each component 1004, 1006, 1008, and 1010 may include a "Window Width" component 1016 for allowing a user to set the contrast of the display in the display panel. The contrast of the display increases with a decrease in the window width, and decreases with an increase in the window width. The "Window Width" component 1016 may include an "Auto Window Width" tool that automatically sets the contrast to a default level. The "Window Width" component 1016 may include a "Window Width Input" tool that may allow a user to input a particular level of contrast. The "Window Width" component 1016 may include a "Window Width Slider" tool that may allow a user to select a relative level of contrast using a slider. The "Window Width" component 1016 may also include a "Window Width Reset" tool to allow a user to reset the contrast level to a default level.

Each component 1004, 1006, 1008, and 1010 may include a "Window Level" component 1018 for allowing a user to set the brightness of the display in the display panel. The brightness of the display increases as the window level is moved toward the maximum gray scale value in the image, and decreases as the window level is moved toward the minimum gray scale value in the image. The "Window Level" component 1018 may include an "Auto Window Level" tool that automatically sets the brightness to a default level. The "Window Level" component 1018 may include a "Window Level Input" tool that may allow a user to input a particular level of brightness. The "Window Level" component 1018 may include a "Window Level Slider" tool that may allow a user to select a relative level of brightness using a slider. The "Window Level" component 1018 may also include a "Window Level Reset" tool to allow a user to reset the brightness level to a default level.

Since the "Window Level" component allows a user to discard gray scale values that are too high, i.e., very bright pixels, this enables filtering out pixel generated by noise and/or dust that are typically very bright. In this case, the window level may be selected such that the bright pixels values associated with noise and/or dust fall to the right of the selected window level, and are thereby excluded from the adjusted image.

The "Overlay Selection" panel 1002 may include one or more display panels 1020, 1022, 1024, and 1026 for separately displaying different biomarker or DNA expression images. The "Overlay Selection" Panel 1002 may also include a preview panel 1028 for showing a preview of the overlaid expression of the markers and/or DNA sequences selected. The preview panel 1028 allows a user to assess the suitability of the contrast/brightness and color settings before applying the settings to the display panel 502.

The "Overlay Selection" panel 1002 may also include a "Save Overlay Settings" tool for saving the selections of the markers and/or DNA sequences provided by a user and corresponding brightness/contrast and color settings for representing the selected markers and/or DNA sequences. Selection of the "Save Overlay Settings" tool may cause the user interface to send an instruction to store, in a database or storage device, the settings provided in the "Overlay Selection" panel 1002. In an exemplary embodiment, the settings may be saved in association with the particular slide-spot that forms the field-of-view displayed in the display panel 502. In an exemplary embodiment, the settings may be saved in association with an identification of the user who provided the settings.

In an exemplary embodiment, when the field-of-view is reloaded in the user interfaces or when the user interface is re-opened with the same field-of-view, expression of the selected markers and/or DNA sequences may be automatically rendered in the stored contrast/brightness settings and colors. In an exemplary embodiment, when a particular user saves a particular set of settings, the settings may be accessed only for that particular user. In another exemplary embodiment, subsequent users may also be able to access the settings saved by a previous user. As a result, a user may select contrast/brightness settings and colors for a set of markers at a single session, and have subsequent sessions in which the user interface automatically presents the markers expression in the same selected contrast/brightness settings and colors. This allows a significant saving of time and effort as it eliminates the need for re-setting color and contrast/brightness settings for the markers each time the user interface is used.

The "Overlay Selection" panel 1002 may also include a "Save Overlay" tool for allowing a user to save the overlaid image displayed in the preview panel in a database or storage device. Exemplary formats for the saved image may include, but are not limited to, jpg files, png files, and the like.

Figure 11:
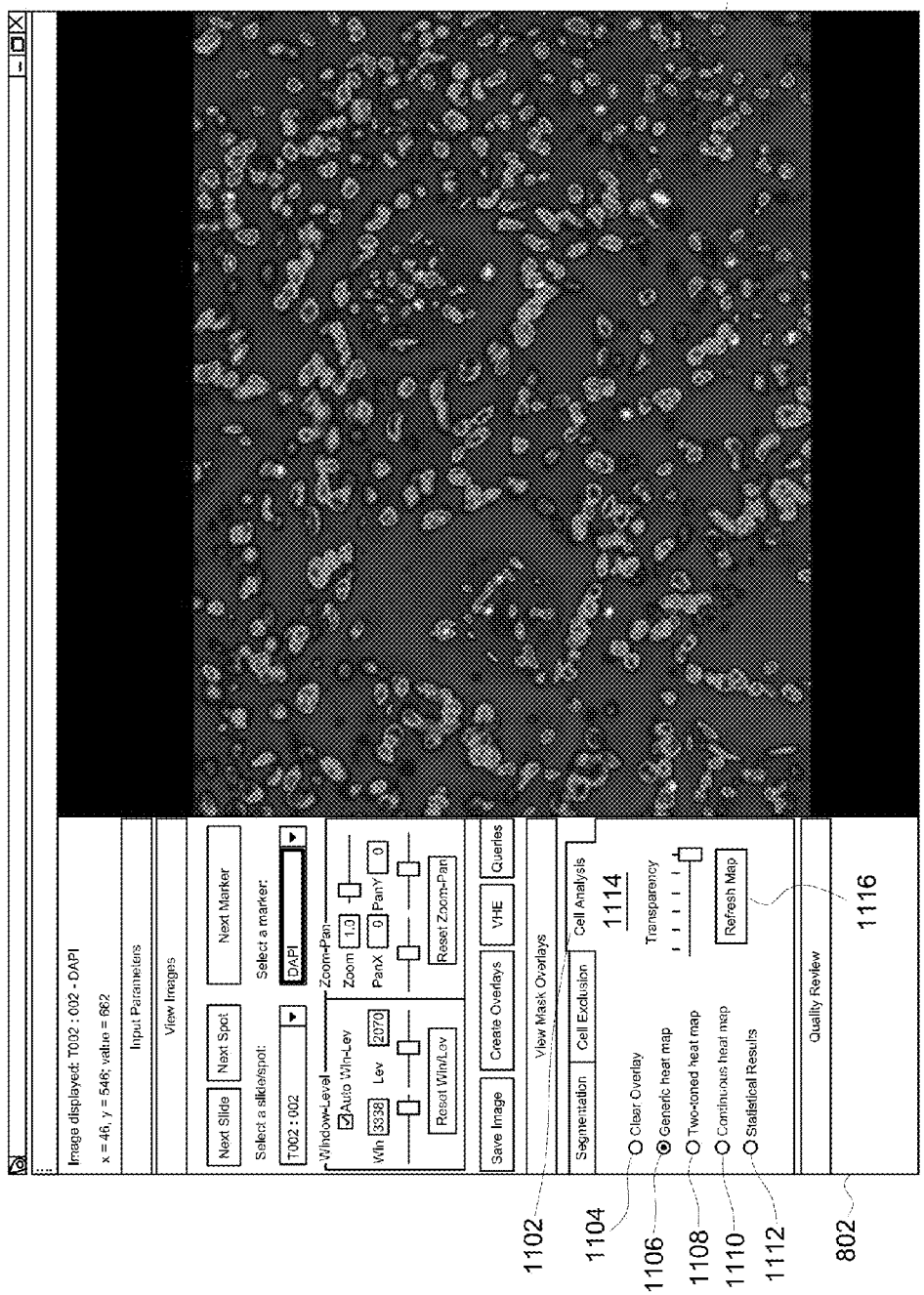
FIG. 11 illustrates an exemplary user interface showing a generic heat map of biomarker expression levels.

As illustrated in FIG. 11, once one or more overlays have been selected for display in the display panel 502, the user may visually display results of analytical methods corresponding to the markers in the selected overlays using a "Cell Analysis" component 1102 provided in the selection panel 802. The "Cell Analysis" component 1102 may allow the user to display results of analytical methods corresponding to each marker in the overlays displayed in the display panel 502. In an exemplary embodiment, the "Cell Analysis" component 1102 may enable the user to select one of the following options: a "Clear Overlay" tool 1104, a "Generic Heat Map" tool 1106, a "Two-Toned or Binary Heat Map" tool 1108, a "Continuous Heat Map" tool 1110, and a "Statistical Results" tool 1112. The "Clear Overlay" tool 1104, when selected for a, may not display expression levels of the marker.

The heat maps may display expression levels of one or more markers on a cell-by-cell basis in one or more pseudo-colors. The expression levels of a plurality of markers may be displayed in the same field-of-view as color overlays on top of a background image showing expression levels of a selected marker. In an exemplary embodiment, the expression levels may be shown on the basis of a biological unit. For example, the expression levels may be shown on a cell-by-cell basis so that a first cell having a first expression level is shown in a first color and a second cell having a second expression level is shown in a second color. In another exemplary embodiment, the expression levels may be shown on the basis of pixels. For example, the expression levels may be shown on a pixel-by-pixel basis so that a first pixel representing a tissue region having a first expression level is shown in a first color and a second pixel representing a tissue region having a second expression level is shown in a second color. In a composite overlaid image of two or more markers, the contribution of each marker may be configured and adjusted, for example, by configuring the contrast/brightness settings of the marker. Other types of colors maps may also be displayed, e.g., convergent maps, divergent maps, cool maps, hot maps, and the like.

The "Generic Heat Map" tool 1106, when selected for a marker, may display expression levels of the marker on a pixel-by-pixel or cell-by-cell basis using default pseudo-color settings. In an exemplary embodiment, a generic heat map may be a continuous heat map or a binary heat map. The display panel in FIG. 11 shows a generic heat map.

Figure 12:
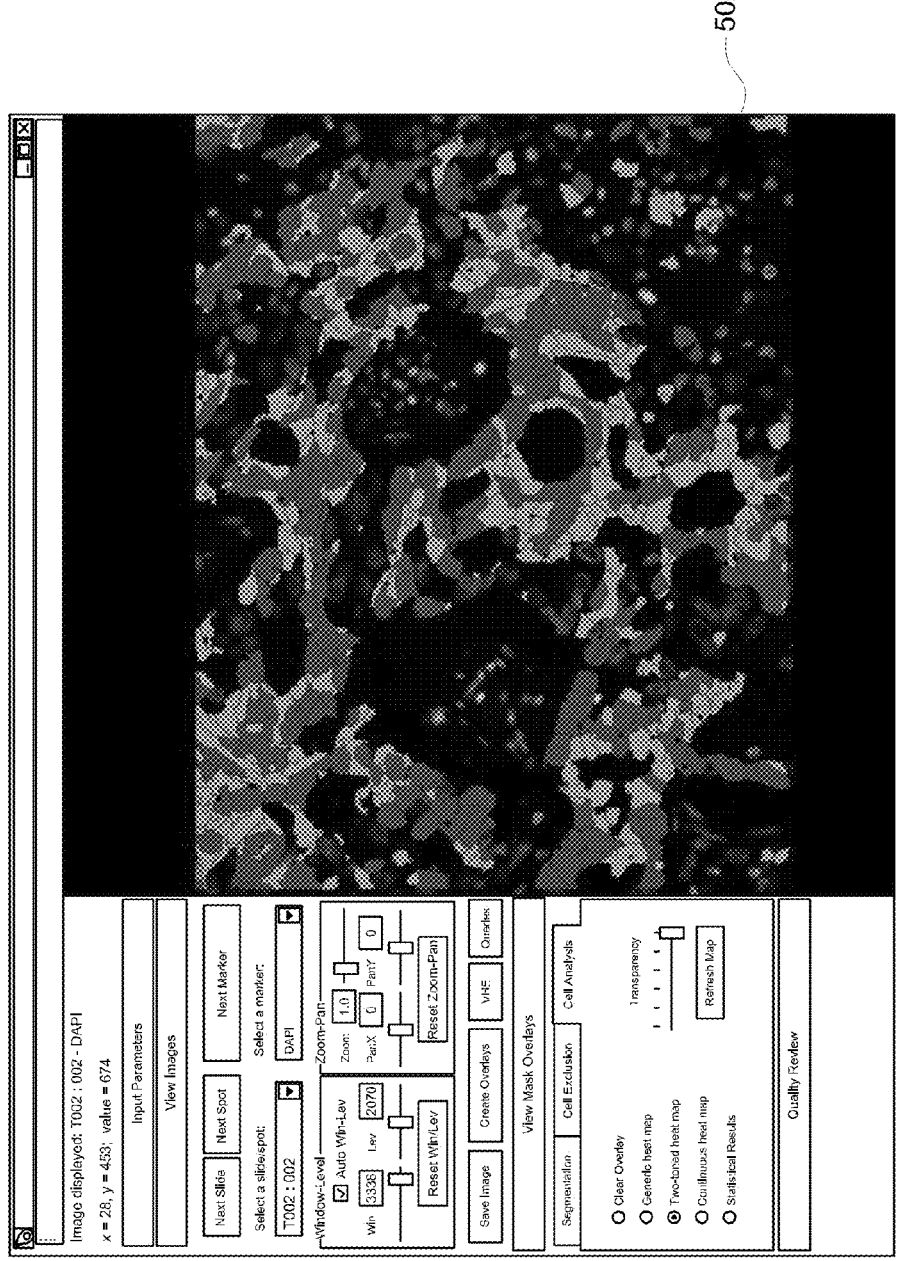
FIG. 12 illustrates an exemplary user interface showing a two-toned heat map of biomarker expression levels.

The "Two-Toned Heat Map" tool 1108, when selected for a marker, may display a binary heat map in which low expression levels of the marker (i.e., expression levels below a predefined user-selected level) are represented on a cell-by-cell basis in a first user-selected pseudo-color and high expression levels of the markers (i.e., expression levels above a predefined user-selected level) in a second user-selected pseudo-color. The image heat maps may be created by assigning a color to each pixel in an image (grayscale value) by using a specific mapping between the colors and underlying expression values. Generally, a number of intensity levels or values in the final image may be pre-defined. In the case of a binary heat map, the number of intensity levels or values is two. In this case, grayscale values may be assigned one of the two values based on one or more pre-defined criteria. For example, if the expression level of a marker in a cell is above a pre-defined threshold, the corresponding grayscale value may be an "on" or "high" value (e.g., the color red). Conversely, if the expression level of a marker in a cell is below a pre-defined threshold, the corresponding grayscale value may be an "off" or "low" value (e.g., the color green). The display panel in FIG. 12 shows a two-toned heat map.

Figure 13:
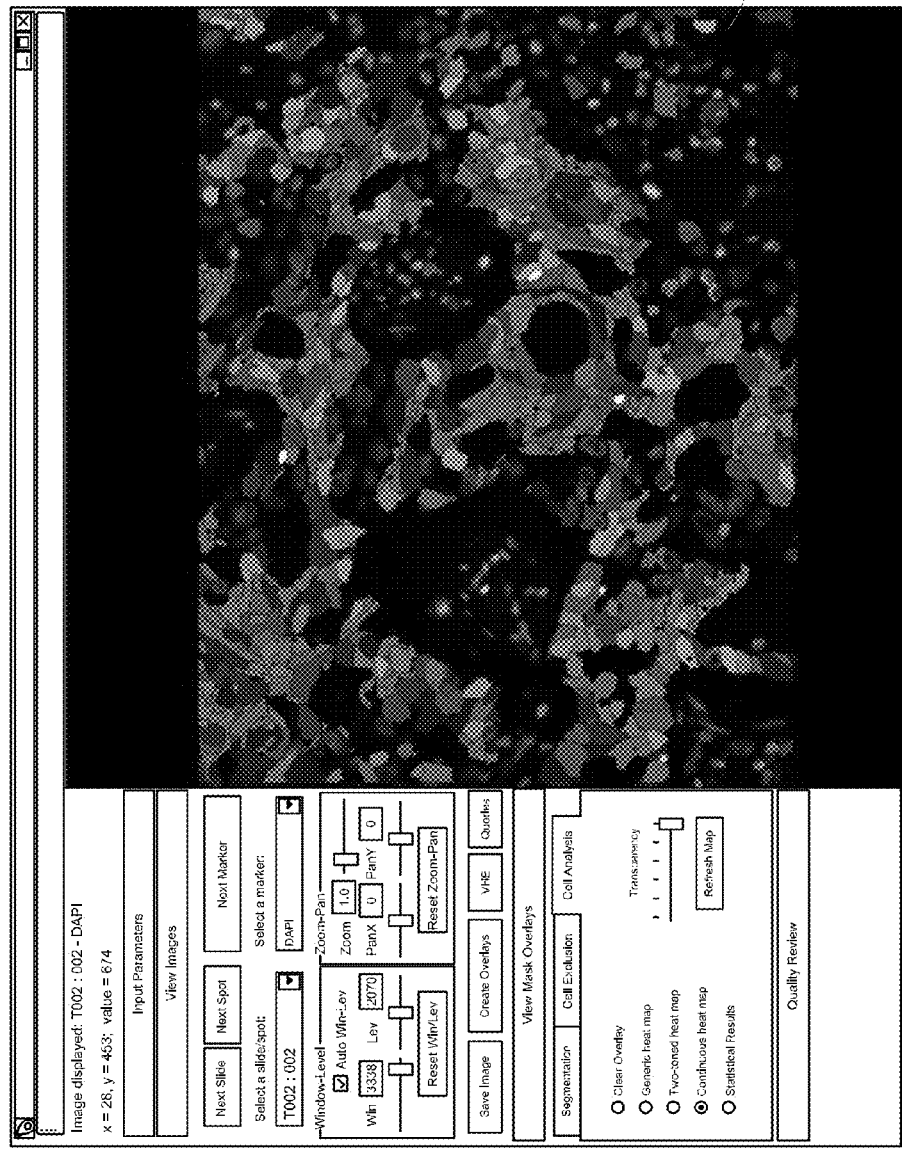
FIG. 13 illustrates an exemplary user interface showing a continuous heat map of biomarker expression levels.

The "Continuous Heat Map" tool 1110, when selected for a marker, may display expression levels of the marker on a cell-by-cell basis in a continuous range of user-selected pseudo-colors. A continuous heat map may use a rainbow color map, where each pixel in an image may be assigned to a color within the spectrum of the rainbow. A typical rainbow color map may include 190-256 unique colors. The main colors may be the 7 colors of the rainbow (VIBGYOR), with the rest of the values interpolated evenly between these main colors. The original levels in the grayscale image may be reduced to 256 or 190 levels in some embodiments. In this manner, each of the grayscale levels or values may be assigned to one of the colors in the color map. Therefore, the final image may appear to be a color image in which each pixel is assigned to a color depending on the grayscale value representing a marker or DNA expression. For example, expression levels of a particular biomarker may be displayed along a range extending between the color violet (for the lowest expression levels) to the color red (for the highest expression levels). The display panel in FIG. 13 shows a continuous heat map.

In another example, a single-cell heat map may be displayed. Rather than assigning each pixel in an image to a color, the single cell segmentation results may be used to color entire cells based on one or more cell-level metrics determined from analysis of marker and/or DNA expression. Areas of the image that are not segmented as "cells" may not be colored. In a continuous heat map, the total number of levels in the image may be converted into a color map scale and each cell may be assigned a unique color based on its metric. In a binary heat map, the same technique may be applied, except that each cell may be assigned one of two colors.

The "Statistical Results" tool 1112, when selected for a marker, may display results of one or more statistical analysis methods performed on marker expression data. The results of any suitable statistical analyses performed on expression data for a cohort may be displayed including, but not limited to, splitting the data into high and low expression values (on a cell-by-cell basis or a pixel-by-pixel basis), generating different types of heat maps, clustering cells based on similar or common characteristics, and the like. The "Statistical Results" tool 1112 enables the results of statistical analysis to be read in and displayed as color masks on top of an single or overlaid biomarker image. This overlaid display of the results of statistical analysis enables a user to assess the quality of the statistical analysis results in the context of the underlying tissue information viewable in the biomarker image.

The tools may be associated with a "Transparency Selection" tool 1114 for allowing a user to select the transparency level at which expression levels of each marker is displayed in the display panel 502. Increasing the transparency level of an image in the display panel 502 may allow the underlying images to show through to a greater degree, while decreasing the transparency level of an image in the display panel 502 may allow the underlying images to show through to a lesser degree.

The selection panel 1102 may also include a "Refresh Map" tool 1116 for allowing a user to load a new overlay in the display panel 502 at runtime. In one example, selection of the "Refresh Map" tool 1116 may allow the user to load one or more new overlays from an external user interface, program (e.g., a program written in the R programming language), device, and the like.

Figure 14:
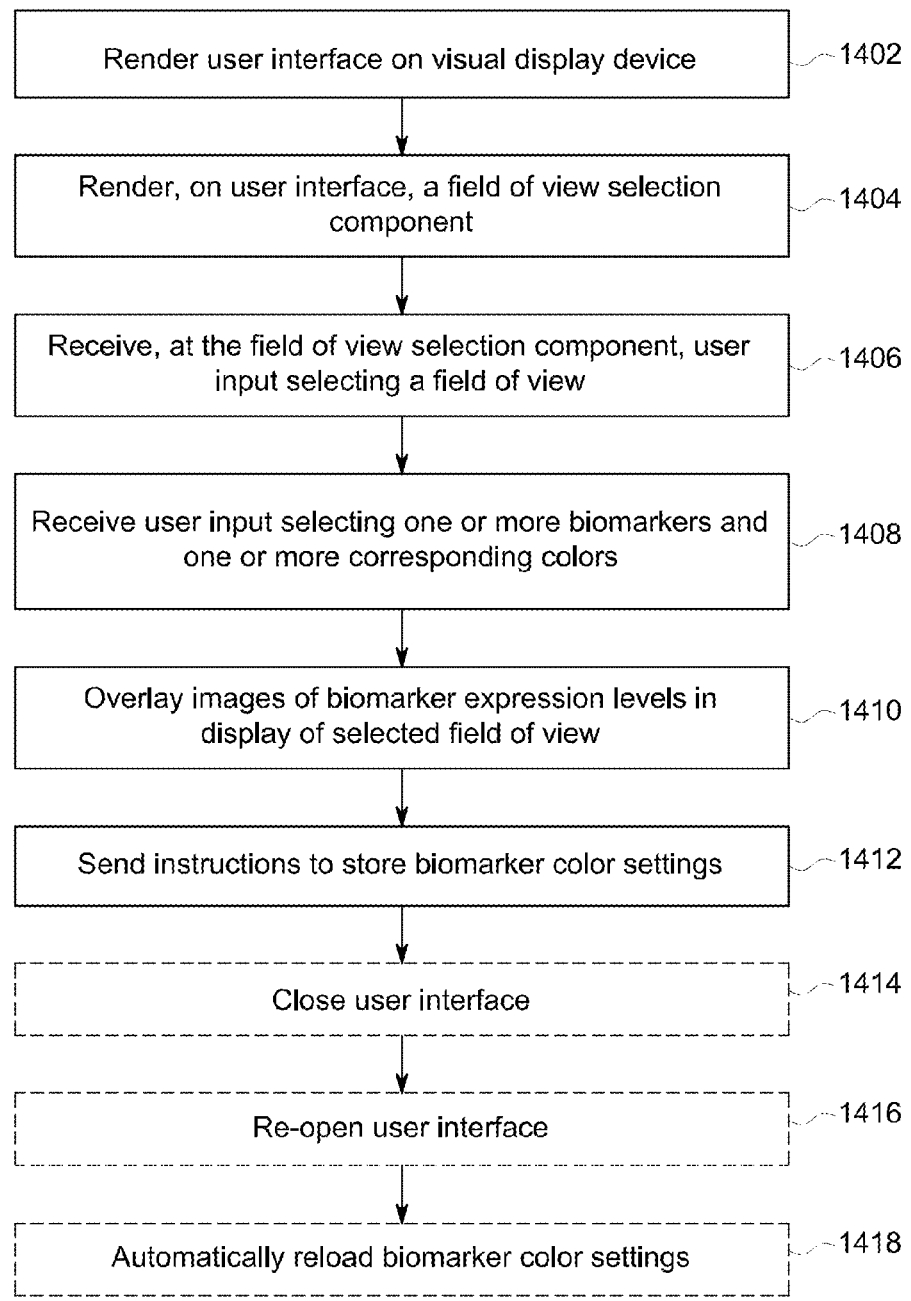
FIG. 14 is a flowchart of an exemplary method for displaying biomarker expression levels.

FIG. 14 is a flowchart illustrating an exemplary computer-implemented method for displaying expression levels of one or more biomarkers in a field-of-view of a biological tissue.

In step 1402, a graphical user interface is rendered on a visual display device.

In step 1404, a field-of-view selection component may be rendered on the graphical user interface. The field-of-view selection component allows a user to select a field-of-view of biological tissue from a data set of a cohort including tissue profile data. The tissue profile data in the data set may include multiplexed biomarker images capturing expression of one or more biomarkers in a plurality of fields-of-view of biological tissue.

In step 1406, the user interface may receive, at the field-of-view selection component, user input selecting a field-of-view of biological tissue.

In step 1408, the user interface may receive user input selecting a first biomarker and a second biomarker. The user interface may also receive user input selecting a first color to represent expression levels of the first biomarker and a second color to represent expression levels of the second biomarker. One of ordinary skill in the art will recognize that the user interface may receive user input selecting a single biomarker and a single color for representing expression levels of the selected biomarker. Similarly, one of ordinary skill in the art will recognize that that user interface may receive user input selecting three or more biomarkers and three or more colors for representing expression levels of the selected biomarkers.

In step 1410, in response to the user input, the user interface may render in an overlaid manner a first image of the selected field-of-view of biological tissue in which expression levels of the first biomarker represented as one or more intensities of the first color, and a second image of the selected field-of-view corresponding to the biological tissue in which the expression levels of the second biomarker are represented as one or more intensities of the second color.

In step 1412, one or more instructions may be sent to store, on a storage device, the selected first color in association with the first biomarker to indicate that expression levels of the first biomarker are to be represented in the first color, such that the first color will be automatically selected in response to receiving user input selecting the first biomarker. Similarly, one or more instructions may be sent to store, on a storage device, the selected second color setting in association with the second biomarker to indicate that expression levels of the second biomarker are to be represented in the second selected color, such that the second color will be automatically selected in response to receiving user input selecting the second biomarker.

In step 1414, the user interface or the image displayed for the selected field-of-view of biological tissue may be closed. In step 1416, a user may re-open the user interface and select the previously selected field-of-view of biological tissue, the previously selected first biomarker, and the previously selected second biomarker.

In step 1418, the user interface may render in an overlaid manner the first image of the selected field-of-view of biological tissue in which expression levels of the first biomarker are automatically represented as one or more intensities of the first color, and a second image of the selected field-of-view corresponding to the biological tissue in which the expression levels of the second biomarker are automatically represented as one or more intensities of the second color.

Figure 15:
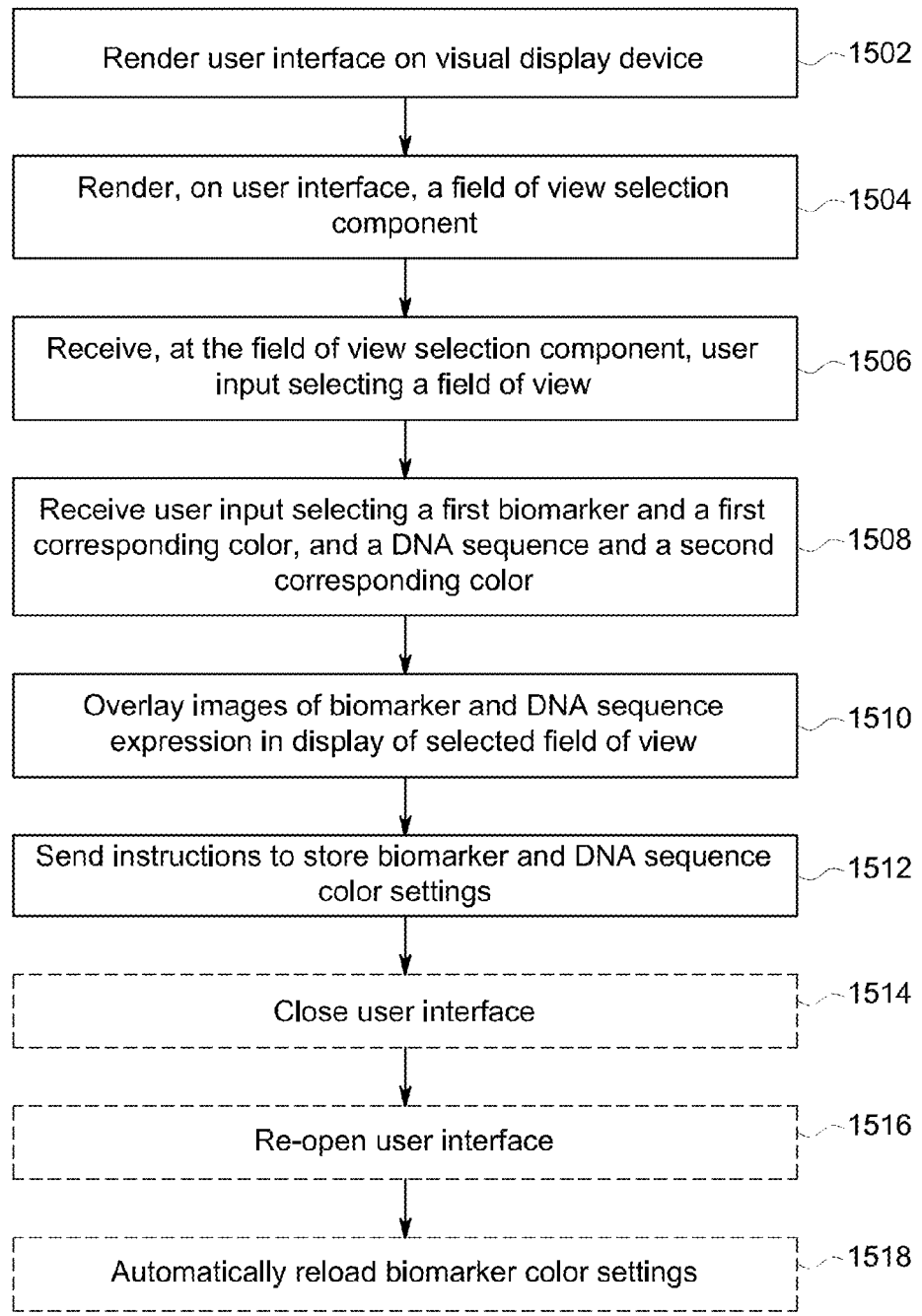
FIG. 15 is a flowchart of an exemplary for displaying biomarker and DNA sequence expression.

FIG. 15 is a flowchart illustrating an exemplary computer-implemented method for displaying expression and non-expression of one or more DNA sequences in a field-of-view of a biological tissue.

In step 1502, a graphical user interface is rendered on a visual display device.

In step 1504, a field-of-view selection component may be rendered on the graphical user interface. The field-of-view selection component allows a user to select a field-of-view of biological tissue from a data set of a cohort including tissue profile data. The tissue profile data in the data set may include multiplexed biomarker images capturing expression of one or more biomarkers in a plurality of fields-of-view of biological tissue.

In step 1506, the user interface may receive, at the field-of-view selection component, user input selecting a field-of-view of biological tissue.

In step 1508, the user interface may receive user input selecting a first biomarker, a first color to represent expression levels of the first biomarker, a first DNA sequence, and a second color to represent expression levels of the second biomarker. Any number of biomarkers and any number of DNA sequences may be selected for concurrent display of their expression and non-expression in an overlaid manner on the image of the selected field-of-view. Selectable numbers of biomarkers include, but are not limited to, 1, 2, 3, 4, 5, 6, 7, 8, 9, 10, 11, 12, 13, 14, 15, 16, 17, 18, 19, and 20. Selectable numbers of DNA sequences include, but are not limited to, 1, 2, 3, 4, 5, 6, 7, 8, 9, 10, 11, 12, 13, 14, 15, 16, 17, 18, 19, and 20. In an exemplary embodiment, image data corresponding to the expression and non-expression of DNA sequences may be obtained using fluorescence in situ hybridization (FISH).

In step 1510, in response to the user input, the user interface may render in an overlaid manner a first image of the selected field-of-view of biological tissue in which expression levels of the first biomarker are represented as one or more intensities of the first color, and a second image of the selected field-of-view corresponding to the biological tissue in which expression and non-expression of the first DNA sequence are represented as one or more intensities of the second color. In another exemplary embodiment, expression of the first DNA sequence may be represented in the second color, and non-expression of the first DNA sequence may be represented in a third color.

In step 1512, one or more instructions may be sent to store, on a storage device, the selected first color in association with the first biomarker to indicate that expression levels of the first biomarker are to be represented in the first color, such that the first color will be automatically selected in response to receiving user input selecting the first biomarker. One or more instructions may be sent to store, on a storage device, the selected second color setting in association with the first DNA sequence to indicate that each expression of the first DNA sequence is to be represented in the second selected color, such that the second color will be automatically selected in response to receiving user input selecting the first DNA sequence. In another exemplary embodiment, one or more instructions may be sent to store, on a storage device, the selected second color setting in association with the first DNA sequence to indicate that expression of the DNA sequence is to be represented using the second color. One or more instructions may also be sent to store a selected third color setting in association with the first DNA sequence to indicate that non-expression of the DNA sequence is to be represented using the third color.

In step 1514, the user interface or the image displayed for the selected field-of-view of biological tissue may be closed.

In step 1516, a user may re-open the user interface and select the previously selected field-of-view of biological tissue, the previously selected first biomarker, and the previously selected first DNA sequence.

In step 1518, the user interface may render in an overlaid manner the first image of the selected field-of-view of biological tissue in which expression levels of the first biomarker are automatically represented as one or more intensities of the first color, and a second image of the selected field-of-view corresponding to the biological tissue in which expression of the first DNA sequence is automatically represented by one or more intensities of the second color. In another exemplary embodiment, expression of the first DNA sequence may be automatically represented in the second color, while non-expression of the first DNA sequence may be automatically represented in a third color.

Exemplary embodiments may display expression of one or more DNA sequences and one or more protein biomarkers in an overlaid manner in the same display panel. The expression and non-expression of DNA sequences on a cell-by-cell basis may be determined based on fluorescence in situ hybridization (FISH). FISH is a technique used to detect and localize the presence or absence of specific DNA sequences on chromosomes. FISH is used in a similar manner as used for multiplexing to detect the hybridization of DNA probes at the cellular level. The probes may look like tiny bright dots on a dark background, with each dot representing a probe on one copy of the gene. The brighter a spot, the more likely it is that the dot represents overlapping copies of the gene. One goal of this technique is to detect the number of copies of specific genes/gene sequences in the tissue, which is accomplished by counting the number of dots (accounting for the brightness of the dots) in an image. Typically, this is done in the context of another ubiquitous gene. Thus, providing an overlay of two or more DNA expression images makes it easier to count the spots for the DNA sequences at the same time. A nuclear marker (such as DAPI) may also be included to provide information on the morphology of the tissue.

Figure 16:
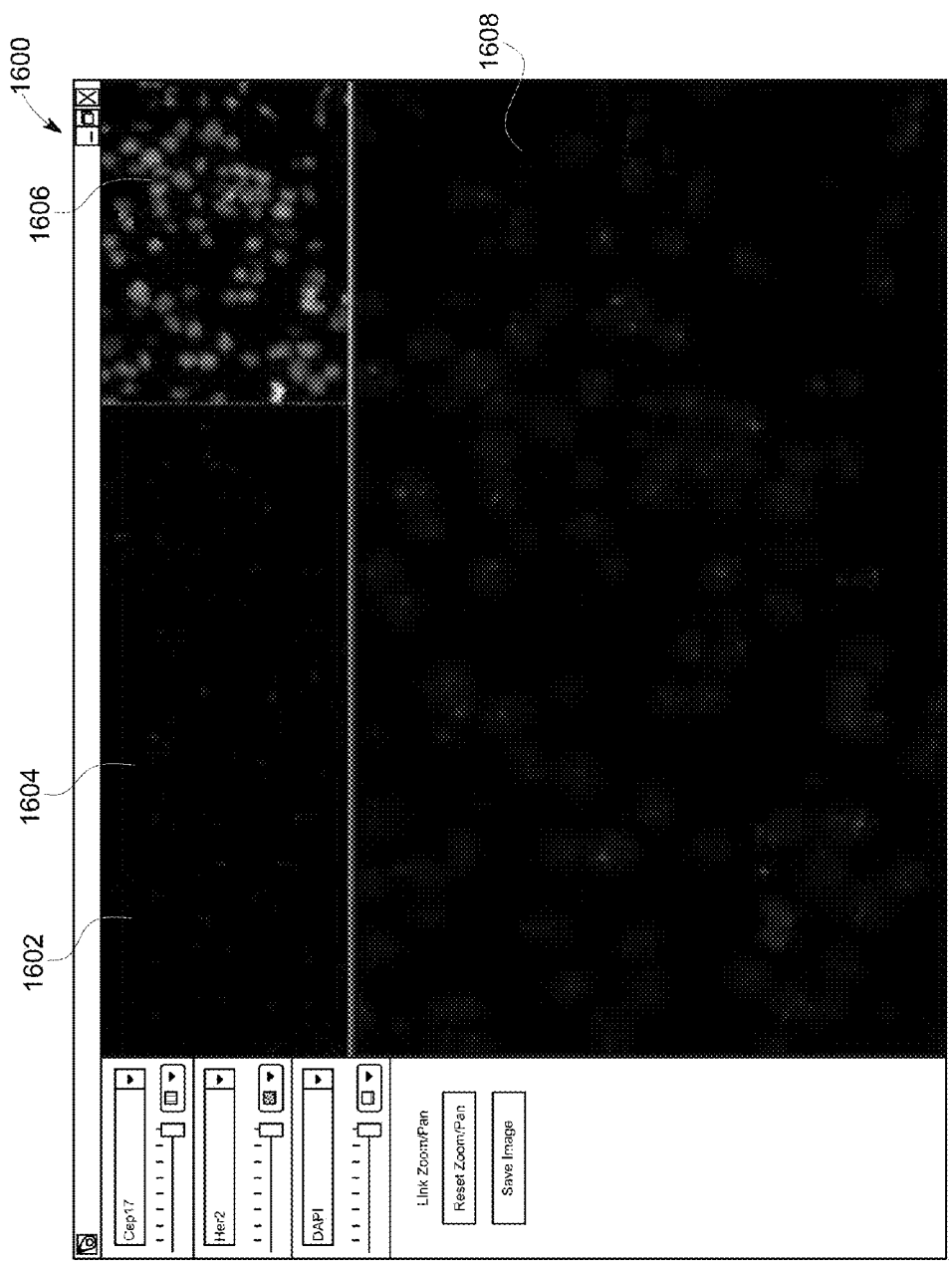
FIG. 16 illustrates an exemplary user interface showing selection of two DNA sequences and a nuclear marker for overlaid display.

FIG. 16 illustrates an exemplary user interface 1600 displaying a first display panel 1602 showing expression and non-expression of a first DNA sequence in a field-of-view of a biological tissue, a second display panel 1604 showing expression and non-expression of a second DNA sequence, and a third display panel 1606 showing expression levels of a nuclear marker. The user interface 1600 includes a fourth display panel 1608 that displays the above three image displays together in an overlaid manner. In the overlaid image display, the expression of the first DNA sequence, the expression of the second DNA sequence, and the expression levels of the nuclear marker are represented together in one blended image. In the blended image, the expression of the first DNA sequence, the second DNA sequence and the nuclear marker are represented with varying intensity levels of different colors. The overlaid image may be created using blending of the different colors representing the DNA sequences and nuclear marker. The contrast and/or brightness of the overlaid image may be adjusted automatically or by user selection to obtain the best visualization. The contribution of the expression of the DNA sequences and the nuclear marker to the overlaid composite image may be adjusted to make counting the DNA spots easier.

The user interface 1600 may include selection components for each marker and DNA sequence selected for display in the panels 1602, 1604, 1606, and 1608. The selection components may be similar to the selection components 1004, 1006, 1008, and 1010 of FIG. 10.

One of ordinary skill in the art will recognize that FIG. 16 shows an illustrative blended image showing expression of the first DNA sequence, the second DNA sequence and the nuclear marker. A blended image may be generated in accordance with exemplary embodiments to represent expression of any number and combination of DNA sequences and/or biomarkers.

Exemplary Implementation of Morphological Feature Selection and Co-localization

The present disclosure addresses a need for improved systems and methods for jointly presenting and/or analyzing inter-particle characteristics, such as such as relative position, orientation and alignment of particles, and intra-particle characteristics, such as size and shape of particles, in a biological sample. More particularly, systems and methods are disclosed herein for presenting and/or analyzing inter-particle morphological characteristics of a biological sample in conjunction with biomarker expression levels of individual particles. As used herein the terms "particle" or "biological particle" are synonymous with the term "biological unit."

In exemplary embodiments, the systems and methods of the present disclosure simultaneously render morphological and statistical representations of the biological sample. Notably, the morphological and statistical representations of the biological sample may be interdependent, for example, wherein a selection of a population of particles with respect to either representation is automatically applied to the other representation. The simultaneous rendering of morphological and statistical representations advantageously allows a user to analyze the same set of data from two different perspectives at the same time.

As described with reference to FIG. 19, systems and methods of the present disclosure may involve a graphical user interface, for example graphical user interface 1900, for facilitating presentation and/or analysis of data related to inter-particle characteristics, for example, inter-particle morphological characteristics, and intra-particle characteristics, for example biomarker expression levels. The graphical user interface may advantageously be used to render, for example, in real time, one or more representations of a selected field-of-view of a biological sample. Graphical user interface 1900 may include a field of view selection component 1930 and a biomarker selection component 1940, each of which may be similar to components described above. Graphical user interface 1900 may further include an expression level criterion selection component 1950 and a morphological feature selection component 1960, each of which will be described below.

Figure 19:
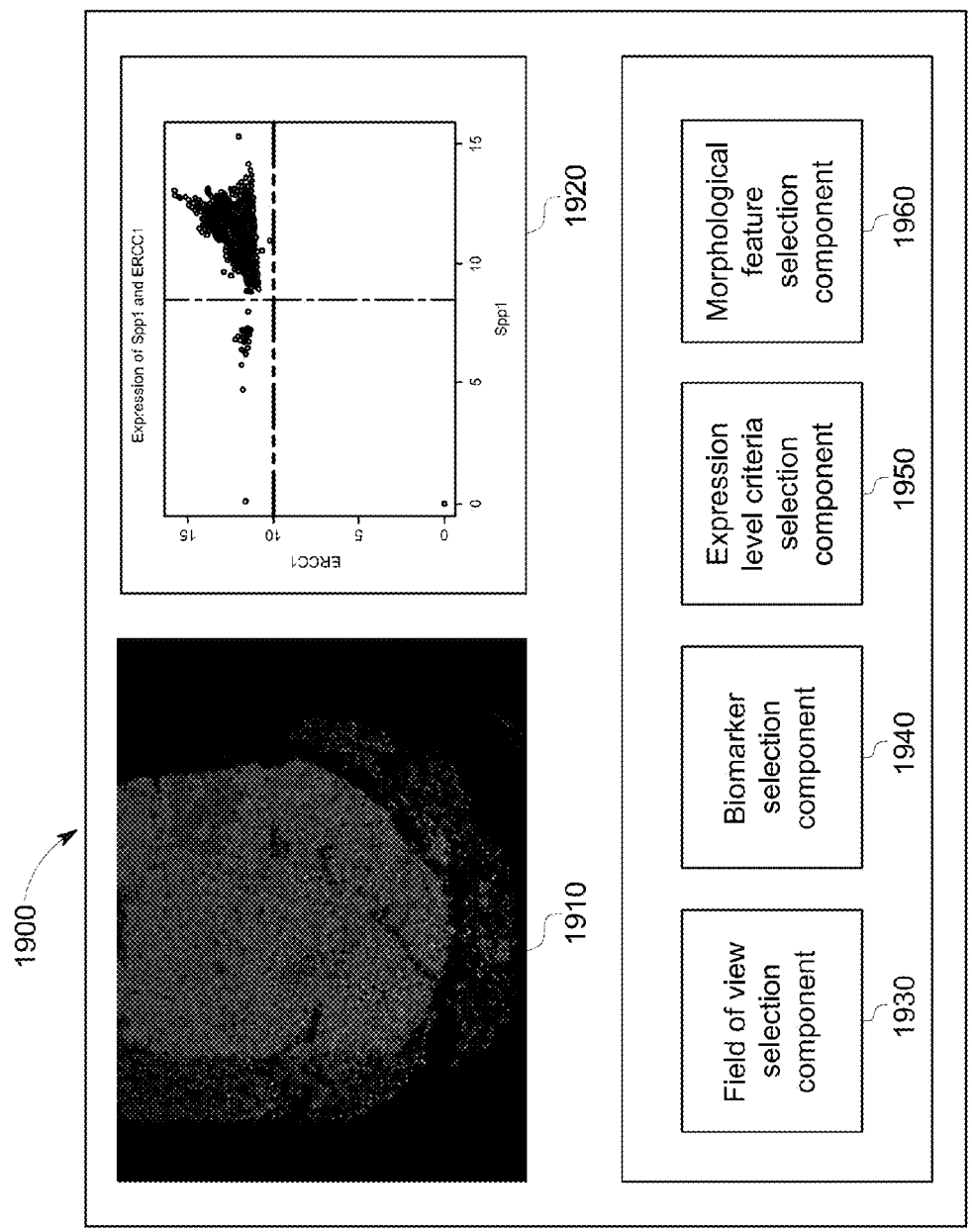
FIG. 19 illustrates an exemplary graphical user interface including both a morphological representation and a statistical representation of a biological sample.

In exemplary embodiments, such as depicted in FIG. 19, the one or more representations of the selected field-of-view may include a morphological representation 1910 of the field of view based on multiplexed, registered images derived from a plurality of images capturing the expression levels of different biomarkers. In some embodiments, the morphological representation 1910 may include an overlay of a plurality of the images of biomarker expression levels. The morphological representation 1910 may include an overlay of five images, for example, each representing biomarker expression levels for a corresponding biomarker in a different color. The morphological representation 1910 may also include a delineation of individual biological particles in the image. Accordingly, the morphological representation 1910 may include a background image identifying, e.g., outlining, the individual biological particles in the biological sample. In exemplary embodiments, the image identifying the individual biological particles may be, or may be derived from, one of the images of biomarkers expression levels.

In exemplary embodiments, the morphological representation 1910 may render a field-of-view of the biological sample selected via the field-of-view selection component 1930. In exemplary embodiments, the morphological representation 1910 may identify one or more populations of biological particles in the biological sample, for example, based on a selected particle characteristic or a group of selected particle characteristics. The one or more populations may be identified by color, transparency, contrast and/or brightness.

In exemplary embodiments, the biomarker selection component 1940 of the graphical user interface 1900 enables a user to select a plurality of biomarkers of interest. In some embodiments, the selection of the plurality of biomarkers is reflected, for example, in real time, in the morphological representation 1910. The morphological representation 1910 may be updated to depict only the selected biomarkers, for example, by including only images corresponding to the selected biomarkers. Alternatively, the morphological representation 1910 may be updated to distinguish the selected biomarkers from the other biomarkers, for example, by adjusting the images corresponding to the selected biomarkers, the non-selected biomarkers, or both. For example, the color, transparency, contrast and/or brightness of any image may be adjusted. In exemplary embodiments, the morphological representation 1910 may advantageously provide visual feedback regarding the one or more selected biomarker(s). For example, the morphological representation 1910, may advantageously facilitate validating/evaluating the effectiveness of the biomarker selection in isolating a target morphologically-related population of particles. In other embodiments, the morphological representation 1910 may facilitate identifying one or more biomarkers that are effective for isolating a target morphologically-related population of particles.

In exemplary embodiments, the expression level criteria selection component 1950 of the graphical user interface 1900 enables a user to select expression level criteria for each of the selected biomarkers. For example, the criteria may be that the expression level is above a certain threshold value, below a certain threshold value, or between two threshold values. In some embodiments, the expression level criteria selection component 1950 may be implemented as a slider for setting upper and/or lower threshold values. Additionally or alternatively, the expression level criteria selection component 1950 may be implemented as one or more boxes for inputting upper and/or lower threshold values.

The selection of the expression level criteria may be reflected in real time in the morphological representation 1910. For example, the morphological representation 1910 may be updated to depict only the population of particles with biomarker expression levels satisfying the selected criteria. This may be accomplished, for example, by filtering out portions of images of biomarker expression levels. Alternatively, the morphological representation 1910 may be updated to distinguish the population of particles with biomarker expression levels satisfying the selected criteria. For example, color, transparency, contrast and/or brightness may be used to distinguish populations of particles.

In exemplary embodiments, the multiplexed image may advantageously provide visual feedback regarding the selected expression level criteria for one or more biomarkers. For example, the morphological representation 1910 may advantageously facilitate validating/evaluating the effectiveness of the expression level criteria for isolating a target morphologically-related population of particles. In other embodiments, the multiplexed image may facilitate identifying appropriate expression level criteria for isolating a target morphologically-related population of particles. In embodiment implementing the expression level criteria selection with a slider may be useful for tuning/adjusting the expression level criteria so as to optimize the criteria for isolating a target morphologically-related population of particles.

In exemplary embodiments, the selected expression level criteria may be used for a subsequent analysis or for sorting of biological particles in one or more biological samples as one might otherwise do with a flow cytometer. For example, a biological sample may first be analyzed using graphical user interface 1900 as described above to determine a set of expression level criteria for one or more biomarkers characterizing a particular population of biological particles in the sample. A biological sample may then be run through a flow cytometer wherein individual biological particles are identified or sorted based on the determined set of expression level criteria.

As described above, a population of biological particles may be selected based on an expression level selection criteria for a plurality of corresponding biomarkers. The selected population of biological particles may then be identified in the morphological representation 1910. For example, the morphological representation 1910 may distinguish a population of biological particles in the biological sample that satisfies each of the biomarker expression level criteria. This may be implemented by distinguishing the population of biological particles that satisfies the biomarker expression level criteria in each of the individual images of a corresponding biomarker expression level. In exemplary embodiments, the population of biological particles that satisfies all of the biomarker expression level criteria may be highlighted in a different color in each of the individual images. Alternatively, the population of biological particles that satisfies all of the biomarker expression level criteria may be highlighted in the same color in each of the individual images.

In some embodiments, a population of biological particles that satisfies one of a plurality of biomarker expression level criteria may be highlighted in the individual image for biomarker with the satisfied expression level criteria. Such a population of particles may be highlighted with a different color and/or transparency than the population of biological particles that satisfies all of the biomarker expression level criteria. In some embodiments, the populations of biological particles that satisfy individual biomarker expression level criteria and the population of biological particles that satisfies all of the biomarker expression level criteria may each be highlighted in a different color. In other embodiments, the population of biological particles can be identified based on a co-location of biomarker expressions levels matching the selected expression level criteria across the overlaid individual images of biomarker expression levels for the selected biomarkers.

In exemplary embodiments, the identity of a population of biological particles that satisfies all of the biomarker expression level criteria may be saved for further experimentation/study. For example, the population may be analyzed to facilitate correlation of the selected biomarkers and corresponding expression level criteria with a biological outcome. Thus, in exemplary embodiments, a plurality of biomarkers and corresponding expression level selection criteria may be used to identify a plurality of particle populations, wherein each population is then correlated to a corresponding biological outcome. Notably, correlation studies for different particle populations may be implemented collaboratively, e.g., via a network infrastructure such as described in greater detail herein with respect to FIG. 2.

In exemplary embodiments, the biomarker selection component 1940 and/or the expression level criteria selection component 1950 may enable a user to select a plurality of biological particles directly in the morphological representation 1910 of the biological sample. This may be implemented, for example, by allowing a user to employ a pointing device to identify and select a plurality of individual biological particles in the morphological representation 1910. A supervised learning algorithm may then be applied to identify, from the set of selected particles, one or more biomarkers and corresponding expression level criteria that distinguish the user selected particles from other particles.

In exemplary embodiments, the morphological feature selection component 1960 of the graphical user interface 1900, additionally or alternatively, enables a user to select a population of biological particles. In some embodiments, the population of biological particles may be selected based on one or more inter-particle morphological characteristics such as proximity or alignment. In other embodiments, the population of biological particles may be selected based on intra-cellular morphological characteristics, such as particle size, particle orientation, major and/or minor axis lengths, second-order momentums, polar signature, templates, boundary length, Euler number, boxing rectangle, compactness, second-order moments, axis of minimal inertia, polar signature, skeletons or any number of internal features of the biological particles. In exemplary embodiments, the morphological feature selection component may advantageously facilitate selection of a population of biological particles that share a common feature. In exemplary embodiments, the morphological feature selection component 1960 may enable a user to define one or more spatial regions of interest in the field of view. For example, the morphological feature selection component 1960 may enable a user to draw a box or other shape around the region(s) of interest.

In exemplary embodiments, the morphological feature selection component 1960 may initiate a cluster analysis of the morphological representation 1910, or a portion thereof, to identify biological particles therein that are characterized by similar morphological features. In exemplary embodiments, a user can provide R script for analysis. The graphical user interface may be adapted to identify the selected cluster(s) of biological particles, for example, by highlighting the selected cluster(s).

In some embodiments, the morphological feature selection component 1960 may enable a user to selecting an intra-particle morphological feature and a corresponding selection criteria, such as a lower threshold, an upper threshold, or two thresholds, for the feature. In some such embodiments, the morphological feature selection component 1960 may enable a user to selecting a plurality of intra-particle morphological features and a corresponding selection criteria for each of the feature. The selection criteria may then be applied to identify a population of particles.

In exemplary embodiments, the morphological feature selection component 1960 may enable a user to select one or more biological particles directly in the morphological representation 1910 for inclusion in an analysis and/or for exclusion from the analysis. This may be implemented, for example, by allowing a user to employ a pointing device to identify and select a plurality of individual biological particles in the morphological representation 1910. A supervised learning algorithm may then be applied to identify, from the set of selected particles, one or more morphological features and corresponding characteristics that distinguish the user selected particles from other particles. In exemplary embodiments, morphological feature selection component 1960 may enable the user to select one or more morphological features for the supervised learning algorithm to consider when identifying distinguishing characteristics. In other embodiments, the supervised learning algorithm may analyze the one or more particles identified by the user to determine which morphological characteristics are best for correlating similarities. The morphological feature selection component 1960 may also enable a user to refine the results of the learning algorithm. For example, the morphological feature selection component 1960 may also enable a user to eliminate one or more particles that should not have been included in the original set and/or to select one or more particles that should have been included in the original set.

In exemplary embodiments, a population of biological particles may be selected for inclusion or exclusion from further analysis based on morphological features and/or biomarker expression characteristics. In some embodiments, the morphological feature selection component may be used to select a population of biological particles for inclusion in further analysis. In other embodiments, the morphological feature selection component may be used to select a population of biological particles for exclusion from further analysis.

In exemplary embodiments, the systems and methods of the present disclosure may automatically select the biomarker(s) and/or the biomarker expression criteria based on the selection of the population of biological cells using the morphological feature selection component. For example, the systems and methods of the present disclosure may advantageously identify those biomarker(s) and/or expression level criteria which best correlate to the biological particles in selected region(s) of the multiplexed image, for example which best differentiate the biological particles inside the selected region(s) from the biological particles outside the selected region(s). Thus, the systems and methods of the present disclosure may advantageously be utilized to determine one or more biomarkers and/or expression level criteria for detecting a biological feature of the biological sample. In exemplary embodiments, the morphological feature selection component may complement or function as the biomarker selection component and/or the biomarker expression level criteria selection component, e.g., by recommending or automatically selecting those biomarker(s) and/or the biomarker expression criteria which best correlate to the biological particles in selected region(s) of the multiplexed image.

In exemplary embodiments, the biomarker selection component, biomarker expression level criteria selection component and/or the morphological feature selection component may be implemented using machine learning to model a population of cells. More particularly, machine learning may be utilized to model a population of cells (for example, in order to distinguish a first population of cells from a second population of cells) based on biomarker expression level characteristics and/or morphological features. The model may then be used as the basis for selecting biomarker(s), biomarker expression level characteristic(s) and/or morphological features.

Figure 39:
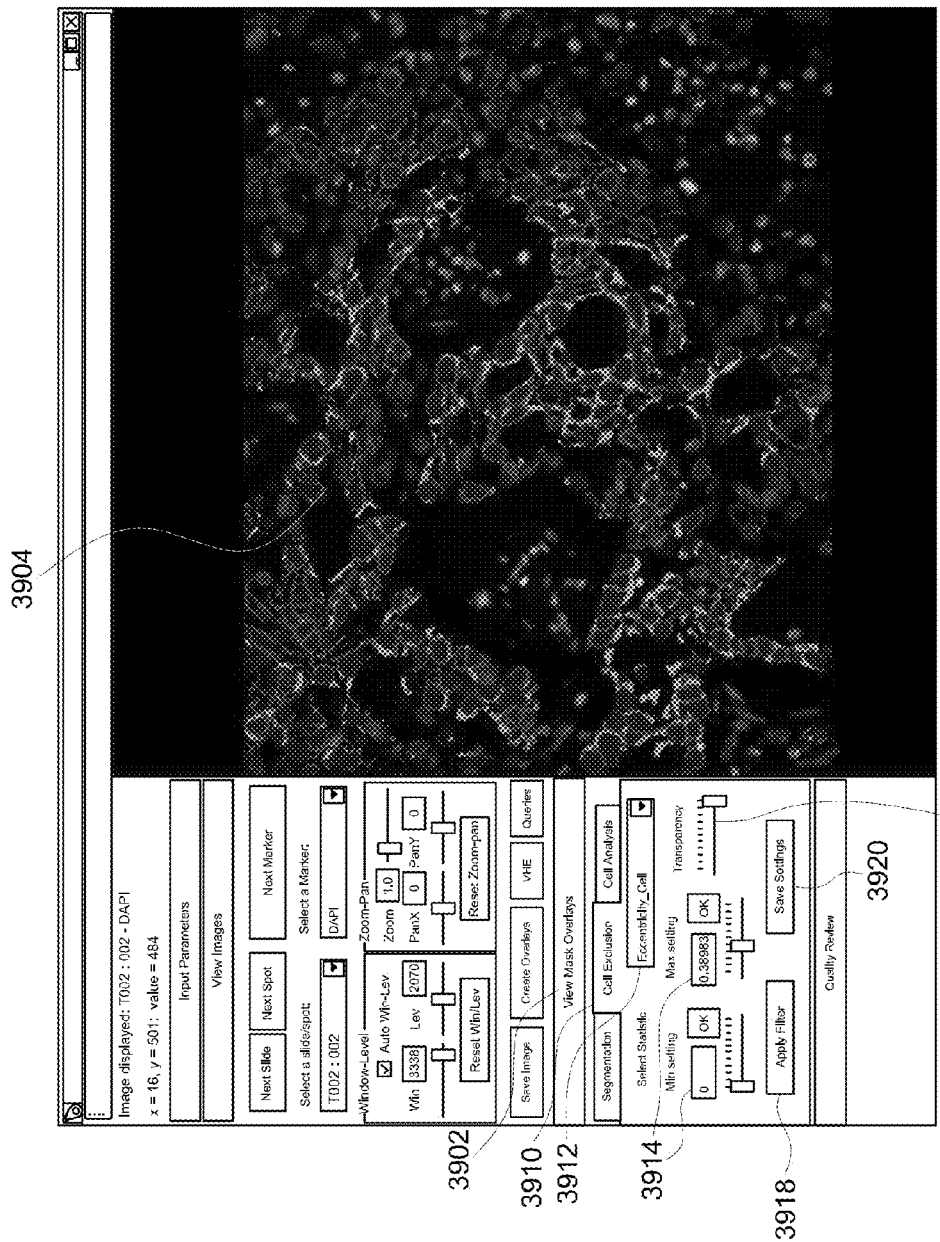
FIG. 39 depicts an exemplary implementation of a morphological feature selection component of a graphical user interface.

FIG. 39 depicts an implementation of an exemplary morphological feature selection component 3910 for selecting a population of biological particles (i.e., cells) for exclusion from further analysis. Note that while the exemplary morphological feature selection component 3910 depicted in FIG. 39 is directed towards cellular exclusion a similar implementation may be used for cellular inclusion. The morphological feature selection component 3910 may include a field 3912 for selecting a morphological feature as well fields 3914 for selecting corresponding criteria, for example min and/or max thresholds, for excluding (or including) biological particles based on the selected feature. The morphological feature selection component 3910 may advantageously be implemented as a mask overlay 3902 with respect to a morphological representation 3904 of a biological sample. Thus, the morphological feature selection component 3910 may include a transparency selection component such as slider 3916 for selecting/adjusting the transparency of the overlay. The morphological feature selection component 3910 may further include a control 3918 for applying the overlay as well as a control 3920 for saving the selection settings, for example, as a .txt file.

In exemplary embodiments, such as depicted in FIG. 19, the graphical user interface 1900 may include a statistical representation 1920 for describing distributions of the biological particles in the biological sample with respect to one or more intra-cellular characteristics, such as biomarker expression levels for one or more biomarkers. In some embodiments, the statistical representation 1920 may be a scatter plot having one or more dimensions, wherein each dimension of the scatter plot represents an intra-cellular characteristic such as an expression level for a particular biomarker. In exemplary embodiments, the statistical representation may be associated with a biomarker selection component for selecting one or more biomarkers. Thus, in exemplary embodiments, the biomarker selection component 1940 may be used to select the intra-cellular characteristic(s) of interest for the statistical representation. For example, the biomarker selection component 1940 may be used to select one or more dimensions for the scatter plot. In some embodiments, the biomarker selection component 1940 may be the same biomarker selection component discussed above with respect to the morphological representation 1910. Alternatively, the biomarker selection component 1940 may be a different biomarker selection component having a dedicated association with the statistical representation 1920.

Figure 17:
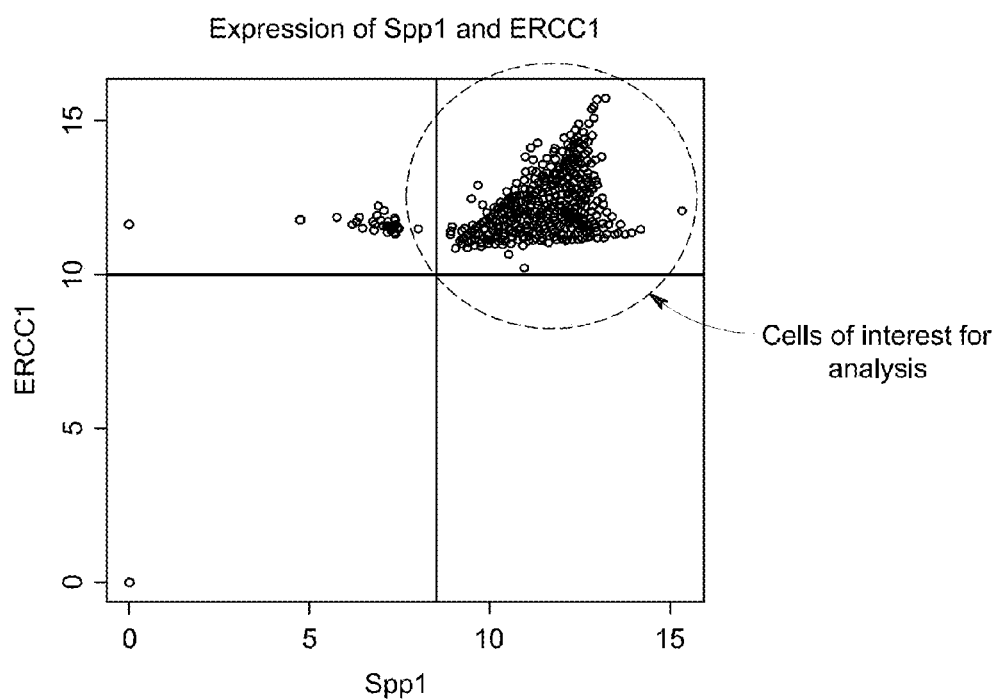
FIG. 17 illustrates an exemplary selection of a population of biological particles in a statistical representation of a biological sample, according to the present disclosure.
Figure 18:
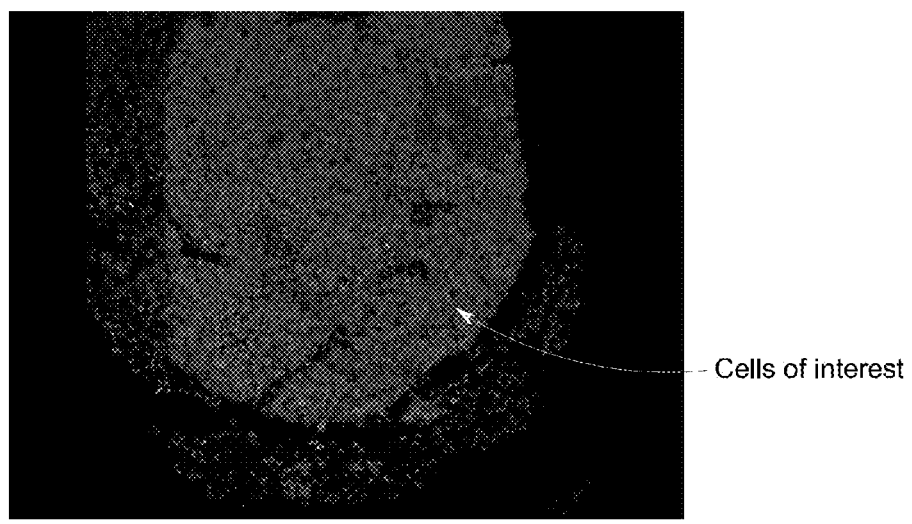
FIG. 18 illustrates an exemplary morphological representation of the biological sample of FIG. 17, reflecting the selected population of biological particles.

In exemplary embodiments, the statistical representation 1920 may advantageously facilitate identification of one or more populations of biological particles having similar intra-cellular characteristics, e.g., similar biomarker expression levels for one or more biomarkers. In exemplary embodiments, a user may identify and/or select a population of biological particles having similar intra-cellular characteristics by defining a region of interest in the statistical representation 1920. For example, the statistical representation 1920 may enable a user to draw a box or other shape around a region of interest, such as depicted in FIG. 17. Alternatively, the statistical representation 1920 may enable a user to select a region of interest by selecting one of the four regions defined by the two thresholds illustrated in FIG. 17. The particles in the region of interest selected in the statistical representation 1920 may then be identified in the morphological representation 1910. For example, particles may be highlighted (e.g., via a color-label) in the morphological representation 1910, such as depicted in FIG. 18.

In other embodiments, cluster analysis may be used to automatically identify and/or select the one or more populations of biological particles having similar intra-cellular characteristics. In exemplary embodiments, the biomarker expression level criteria selection component may be implemented by selecting for example, manually or automatically via cluster analysis, of one or more populations of biological particles in the statistical representation (e.g., wherein the selected expression level criteria for one or more biomarkers defines the selected region in the statistical representation).

In exemplary embodiments, a graphical user interface may be configured to simultaneously display a morphological representation 1910 and a statistical representation 1920 reflecting, for a desired field-of-view, the same selected population of biological particles. Thus, the morphological representation 1910 and the statistical representation 1920 may provide different perspectives on the same analysis and/or manipulation of the same set of data. Moreover, any modification of the information selected for display in the morphological representation 1910 or the statistical representation 1920 may affect the information displayed in both representations. For example, a selection of a biomarker and/or an expression level criteria may affect both the morphological representation 1910 and the statistical representation 1920 at approximately the same time. Moreover, any selection of a population of biological particles may be simultaneously identified in both the morphological representation 1910 and the statistical representation 1920. Thus, the systems and methods of the present disclosure advantageously facilitate simultaneous morphological and statistical inspection of characteristics of a biological sample. Thus, the graphical user interface 1900 may enable a user to select a population of biological particles by a cluster in the statistical representation 1920, such as depicted in FIG. 17, and then enable the user to see how the biological particles in the selected population correlate in the morphological representation 1910, such as depicted in FIG. 18. The morphological representation 1910 thus enable the user to explore a possible correlation of the selected biological particles to a morphological feature. Additionally or alternatively, the graphical user interface 1900 may enable a user to select a population of biological particles based on a clustering in the morphological representation 1910 and then enable the user to see how the biological particles in the selected population correlate in the statistical representation 1910. The statistical representation 1920 thus enable the user to explore a possible correlation of the selected biological particles to a statistical feature.

Figure 38A:
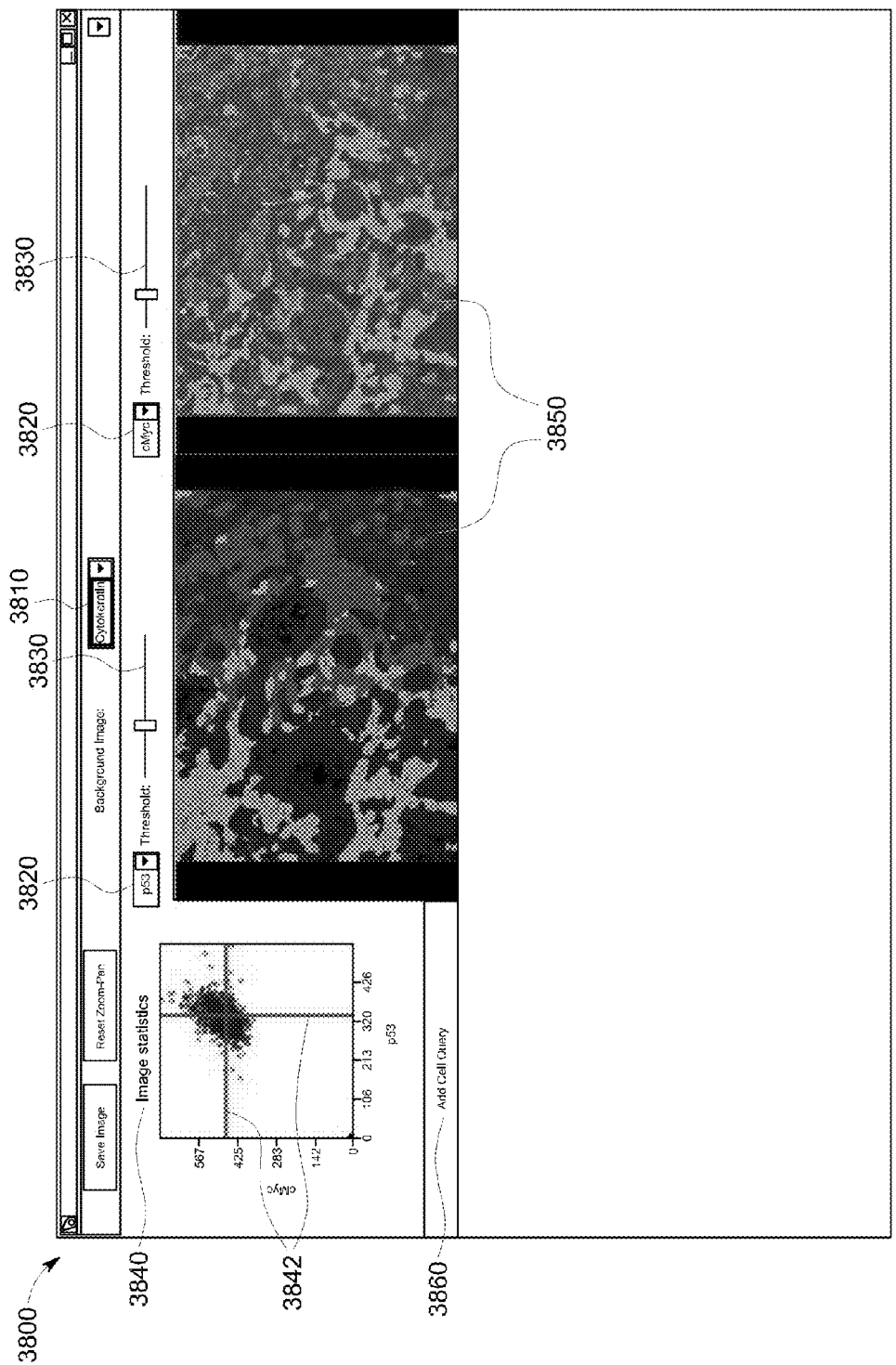
FIGS. 38A, 38B, and 38C depict and an exemplary graphical user interface including a statistical representation.
Figure 38B:
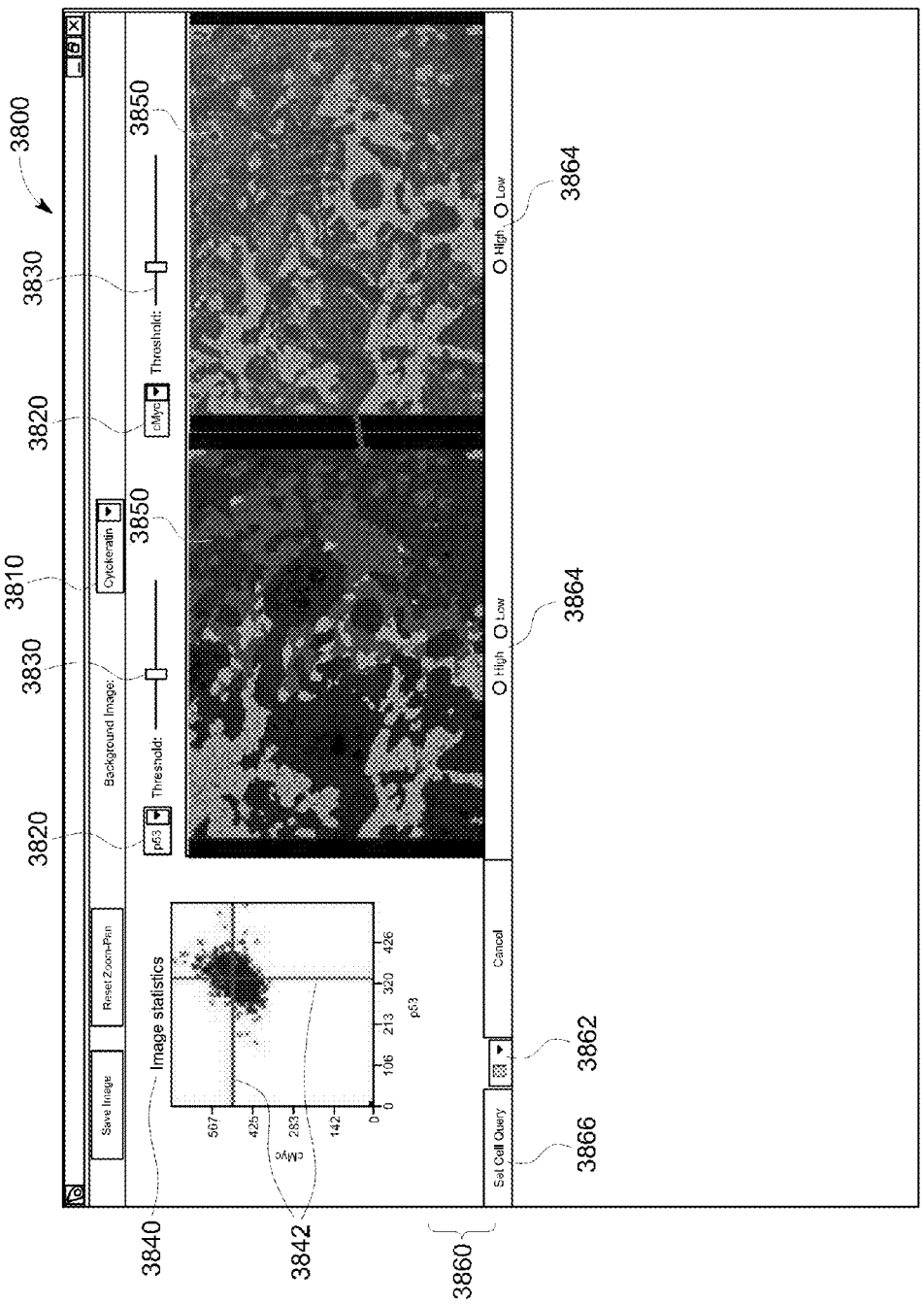
Figure 38C:
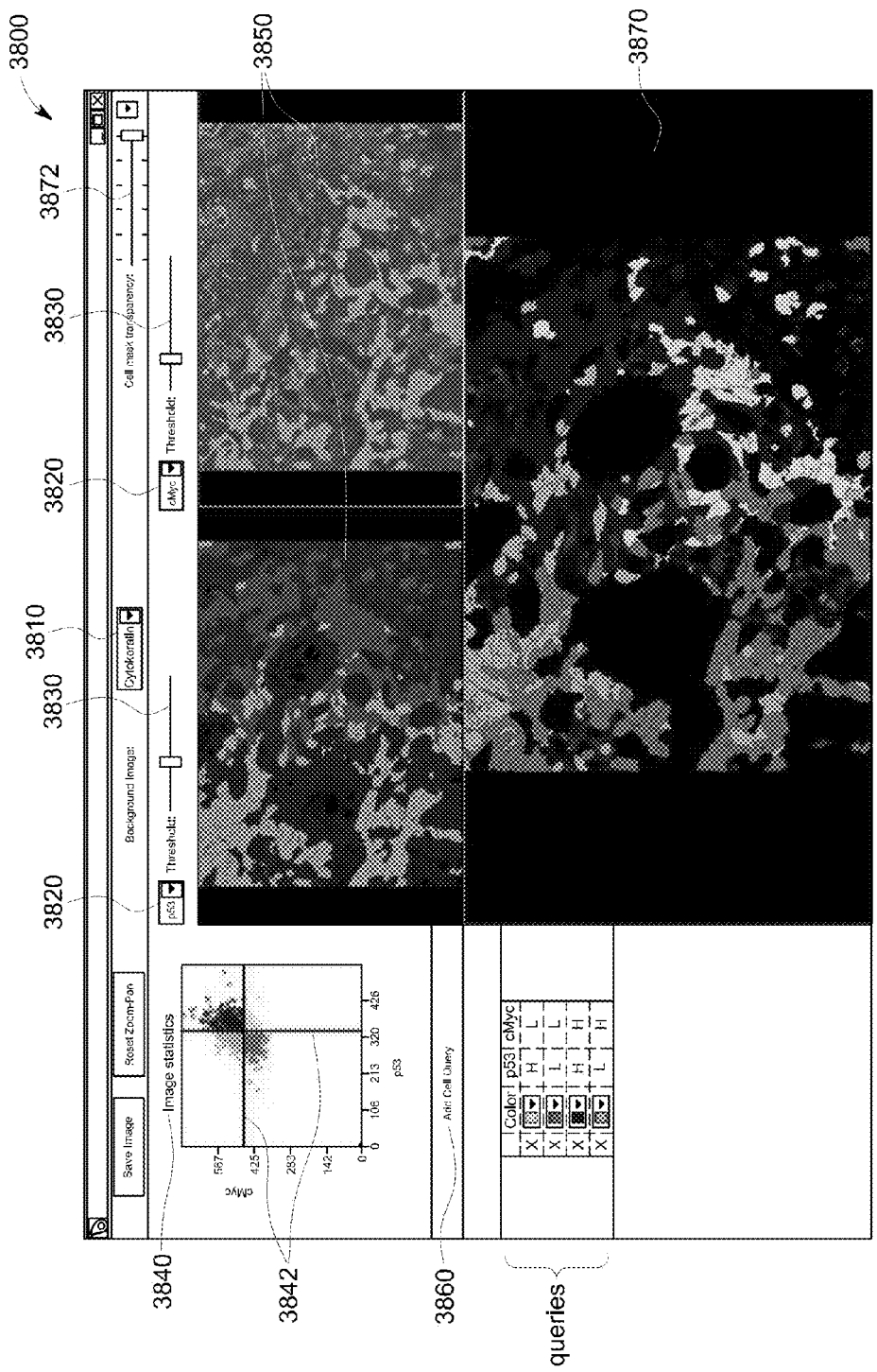

FIGS. 38A-38C depict an exemplary graphical user interface 3800 simultaneously displaying morphological and statistical representations of a biological sample. As noted above, an exemplary morphological representation may be a multiplexed imaged overlaying one or more mask overlays based on biomarker expression level over a background image of the biological sample and an exemplary statistical representation may be a scatter plot. The graphical user interface 3800 may include a background image selection component 3810 for selecting a background image of the biological sample, a biomarker selection component 3820 for selecting one or more biomarkers of interest and a biomarker expression level criteria selection component 3830 for selecting expression level criteria (for example, a threshold) for each of the selected biomarkers. Each of the background image selection component 3810, biomarker selection component 3820 and biomarker expression level criteria selection component 3830 may be similar to components described above. The biomarker selection component 3810 may be used to select one or more biomarkers as dimensions for a displayed statistical representation 3840 of the biological sample. The biomarker expression level criteria selection component 3820 may then be used to select criteria for each selected biomarker. The selected criteria may be simultaneously reflected in both statistical and morphological representations. Thus, the graphical user interface 3800 may both overlay the selected criteria 3842 with respect to the statistical representation 3840 and display, for each biomarker, a morphological representation 3850 of the biological sample, differentiating (for example, via color) populations of particles based on the selected criteria for that biomarker.

In some embodiments, the selected biomarker expression level criteria for the biomarkers may be adjusted based on the statistical and/or morphological implications thereof. Thus, for example, biomarker expression level criteria for a biomarker may be adjusted so as to differentiate a morphologically significant population of particles as reflected in the morphological representation 3850 for that biomarker. Alternatively, biomarker expression level criteria for a biomarker may be adjusted so as to differentiate between statistically significant clusters of particles, as reflected in the statistical representation 3840. Once biomarker expression level criteria are satisfactory established for each of the biomarkers, a query control 3860 may generate a query of the biological sample based on the established biomarker expression level criteria.

As depicted in FIG. 38B, the query control 3860 may include a color selection component 3862 for selecting, a color representative of the query, a query parameter control 3864 for selecting query parameters for the query and a field 3866 for confirming the query. In particular, the query parameter control may be used to establish, for each biomarker, whether to include or exclude, particles satisfying the expression level criteria for that biomarker from the query. The query parameter control may also be used to establish whether the query is an "AND" query or and "OR" query for the selected query parameters. Thus, the query may advantageously be configured to return a population of biological particles matching all of the query parameters or a population of biological particles matching any of the query parameters.

As depicted in FIG. 38C, results for queries established via the query control 3860 may be reflected in a morphological representation 3870 as well as in the statistical representation 3840. In exemplary embodiments, the queries may be implemented as a mask overlay with respect to the morphological representation 3870 of a biological sample. A transparency control, for example, slider 3872, may be used to adjust a transparency of an overlaid cell query mask.

Figure 35:
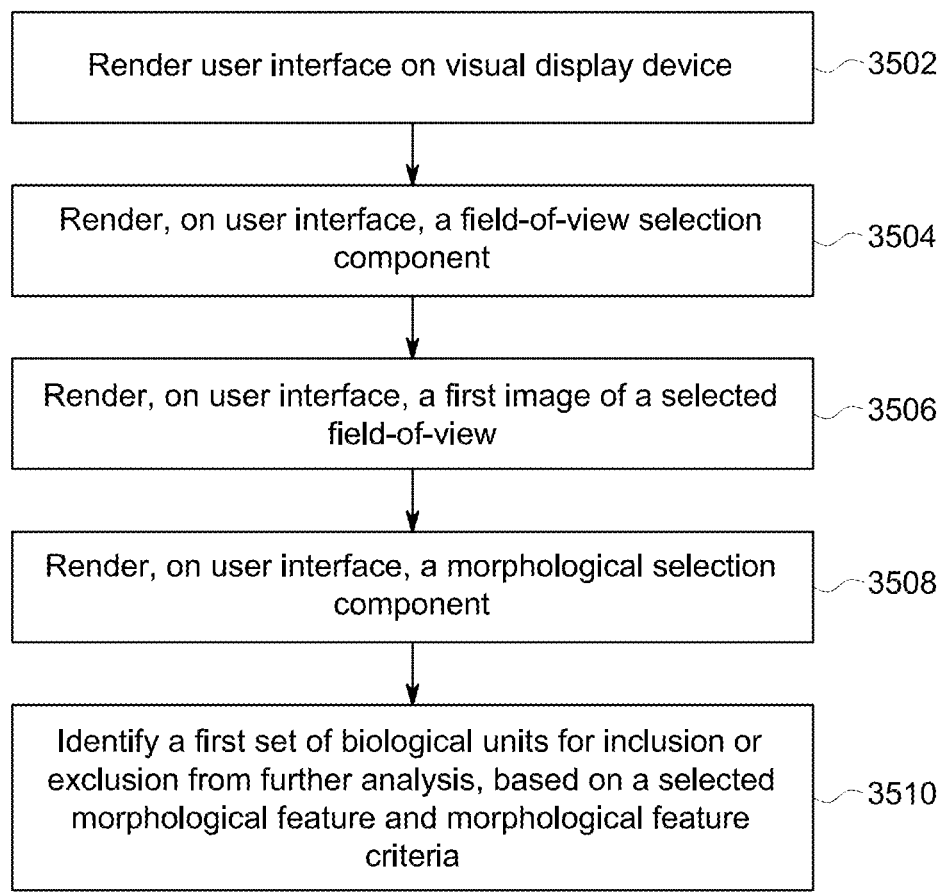
FIG. 35 is a flowchart of an exemplary method for selectively displaying representations of biological units of interest in a biological tissue.

FIG. 35 is a flow chart illustrating an exemplary computer-implemented method 3500 for selectively displaying representations of biological units of interest in biological tissue.

In step 3502, a graphical user interface is rendered on a visual display device.

In step 3504, a field-of-view selection component is rendered on the graphical user interface allowing a user to select a field-of-view from a data set comprising tissue profile data including registered multiplexed biomarker images capturing expression of a plurality of biomarkers in a plurality of fields of view of biological tissue. Advantageously the individual biological units in the plurality of fields of view may delineated.

In step 3506, in response to user input selecting the field-of-view corresponding to a biological tissue at the field-of-view selection component, rendering, on the graphical user interface, a first image of the selected field-of-view corresponding to the biological tissue, the first image representing expression levels of a first biomarker and including representations of individual biological units in the biological tissue.

In step 3508 a morphological feature selection component is rendered on the graphical user interface allowing a user to select from among the delineated individual biological units a first morphological feature meeting at least one first morphological feature criteria.

In step 3510, in response to user input selecting a first morphological feature meeting at least one first morphological feature criteria, a first set of biological units represented in the first image is identified that meet the at least one first morphological feature criteria in the first image of the selected field-of-view as biological units for inclusion or exclusion from further analysis.

Figure 36:
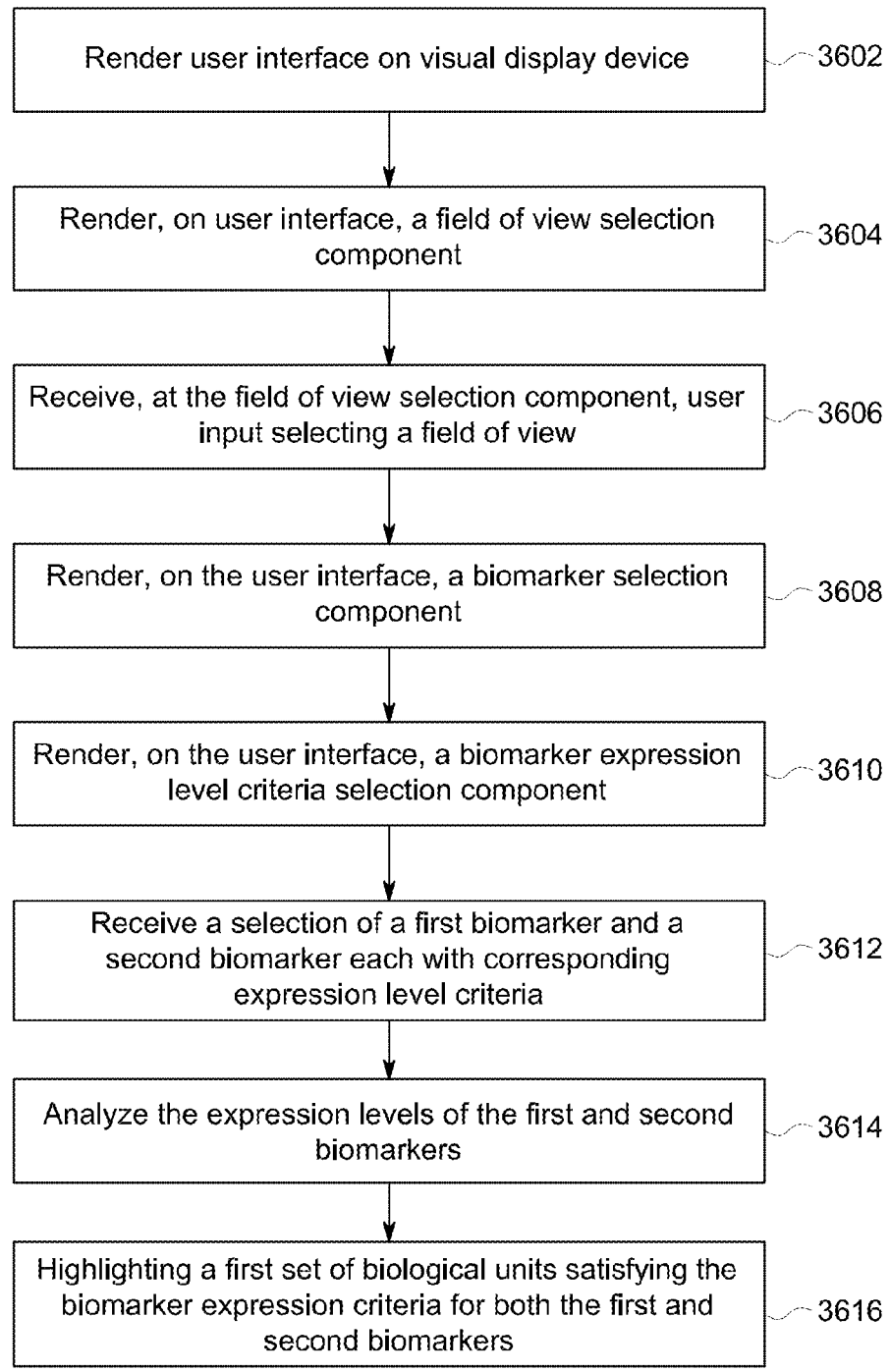
FIG. 36 and is a flow chart of exemplary method for displaying expression levels of two or more biomarkers in a biological tissue.

With reference to FIG. 36, an exemplary computer-implemented method 3600 for displaying expression levels of two or more biomarkers in biological tissue is presented.

In step 3602 a graphical user interface is rendered on a visual display device.

In step 3604 a field-of-view selection component is rendered on the visual display device allowing a user to select a field-of-view from a data set comprising tissue profile data including registered multiplexed biomarker images capturing expression of a plurality of biomarkers in a plurality of fields of view of biological tissue, wherein individual biological units in the plurality of fields of view are delineated.

In step 3606 user input is received at the field-of-view selection component of the graphical user interface, selecting a field-of-view corresponding to a biological tissue.

In step 3608 a biomarker selection component is rendered on the graphical user interface allowing a user to select a first biomarker and a second biomarker from among the plurality of biomarkers having a corresponding image in the multiplexed biomarker images of the selected field-of-view.

In step 3610 a biomarker expression level selection component is rendered on the graphical user interface allowing a user to select a first biomarker expression level criterion for the selected first biomarker and a second biomarker expression level criterion for the selected second biomarker.

In step 3612 user input is received at the graphical user interface, selecting the first biomarker, the first biomarker expression level criterion, the second biomarker, and the second biomarker expression level criterion.

In step 3614 the expression levels of the selected first biomarker and the expression levels of the selected second biomarker in the selected field-of-view are automatically analyzed.

In step 3616 the corresponding images of the selected field-of-view are rendered in an overlaid manner on the graphical user interface and highlighting a first set of biological units in the biological tissue that meets both the first biomarker expression level criterion for the selected first biomarker and the second biomarker expression level criterion for the selected second biomarker.

Figure 37:
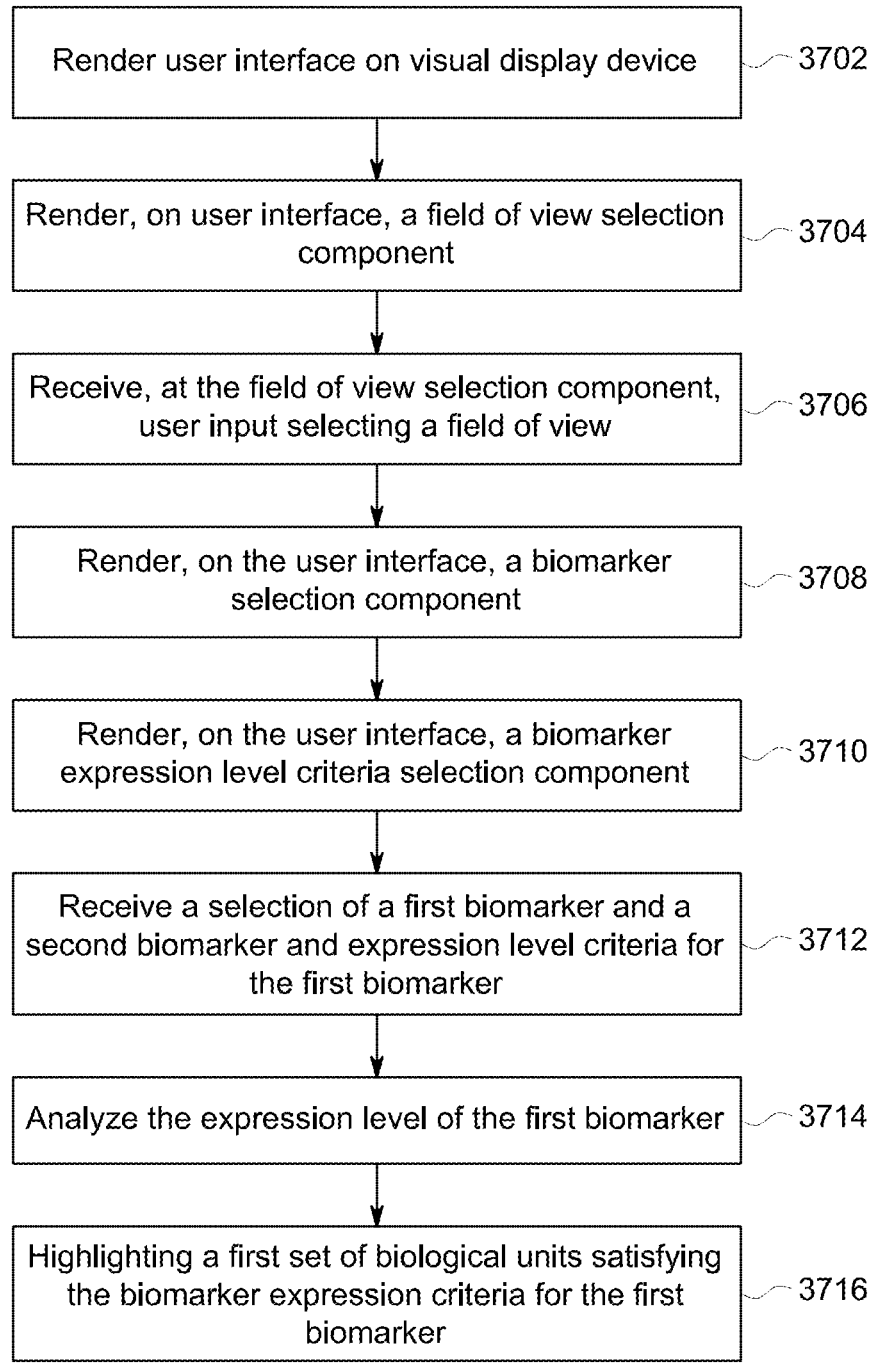
FIG. 37 is a flowchart of an exemplary method for displaying biomarker expression levels.

With reference to FIG. 37, an exemplary computer-implemented method is presented for displaying expression levels of two or more biomarkers in biological tissue.

In step 3702 a graphical user interface is rendered on a visual display device.

In step 3704 a field-of-view selection component is rendered on the graphical user interface allowing a user to select a field-of-view from a data set comprising tissue profile data including registered multiplexed biomarker images capturing expression of a plurality of biomarkers in a plurality of fields of view of biological tissue, wherein individual biological units in the plurality of fields of view are delineated.

In step 3706 user input is received at the field-of-view selection component of the graphical user interface, selecting a field-of-view corresponding to a biological tissue.

In step 3708 a biomarker selection component is rendered on a graphical user interface allowing a user to select a first biomarker and a second biomarker from among the plurality of biomarkers having a corresponding image in the multiplexed biomarker images of the selected field-of-view.

In step 3710 a biomarker expression level selection component is rendered on the graphical user interface allowing a user to select a first biomarker expression level criterion for the selected first biomarker.

In step 3712 user input is received at the graphical user interface, selecting the first biomarker, the first biomarker expression level criterion, and the second biomarker.

In step 3714 the expression levels of the selected first biomarker in the selected field-of-view are automatically analyzed.

In step 3716 corresponding images of the selected field-of-view are rendered in an overlaid manner on the graphical user interface and highlighting a first set of biological units in the biological tissue that meets both the first biomarker expression level criterion for the selected first biomarker.

Exemplary Correlation of Clinical Outcome with Tissue Characteristics

Exemplary embodiments may provide or configure a user interface to allow a user to determine a correlation between a clinical outcome and a user-selectable aspect of a field-of-view of biological tissue displayed on the user interface. Exemplary user-selectable clinical outcomes may include, but are not limited to, positive diagnosis of a disease or tissue condition, negative diagnosis of a disease or tissue condition, a disease prognosis, a prediction of drug response, stratification into a clinically-relevant group, and the like. Exemplary user-selectable aspects of a field-of-view of biological tissue may include, but are not limited to, one or more cells, one or more sub-cellular components of cells, one or more collections of multiple cells, one or more regions of the field-of-view, one or more characteristics of biological units in the field-of-view, expression levels of one or more biomarkers, and the like.

Upon user selection of one or more aspects of a field-of-view of biological tissue, exemplary embodiments may access biological tissue data corresponding to a cohort to which the selected field-of-view belongs. For example, if the user-selected field-of-view corresponds to a first biological tissue sample of a first patient with breast cancer, exemplary embodiments may access data corresponding to multiple biological tissue samples corresponding to a patient cohort including the first patient and one or more other patients with breast cancer. Exemplary embodiments may retrieve data for the cohort corresponding to one or more features characteristic of the user-selected aspects of the field-of-view. Exemplary embodiments may then automatically perform correlation analysis between the selected clinical outcome and the one or more features for the cohort. The correlation analysis may be used to determine whether a positive correlation or a negative correlation exists between the selected clinical outcome and the one or more features for the cohort.

Exemplary embodiments may, for example, determine that high expression levels of a particular biomarker in biological tissue of a patient cohort are correlated with a disease diagnosis. This may allow automatic determination of one or more biomarkers that are clinically relevant to a particular clinical outcome, which may open avenues for further research into the pathologies of the clinical outcome. Furthermore, the determination of a correlation may allow creation of a predictive model. For example, if it is determined that a clinical outcome is positively correlated with high expression levels of a particular biomarker in biological tissue of a patient cohort, then subsequent detection of high expression levels of the biomarker may indicate the possibility of the clinical outcome in the biological tissue.

Figure 20:
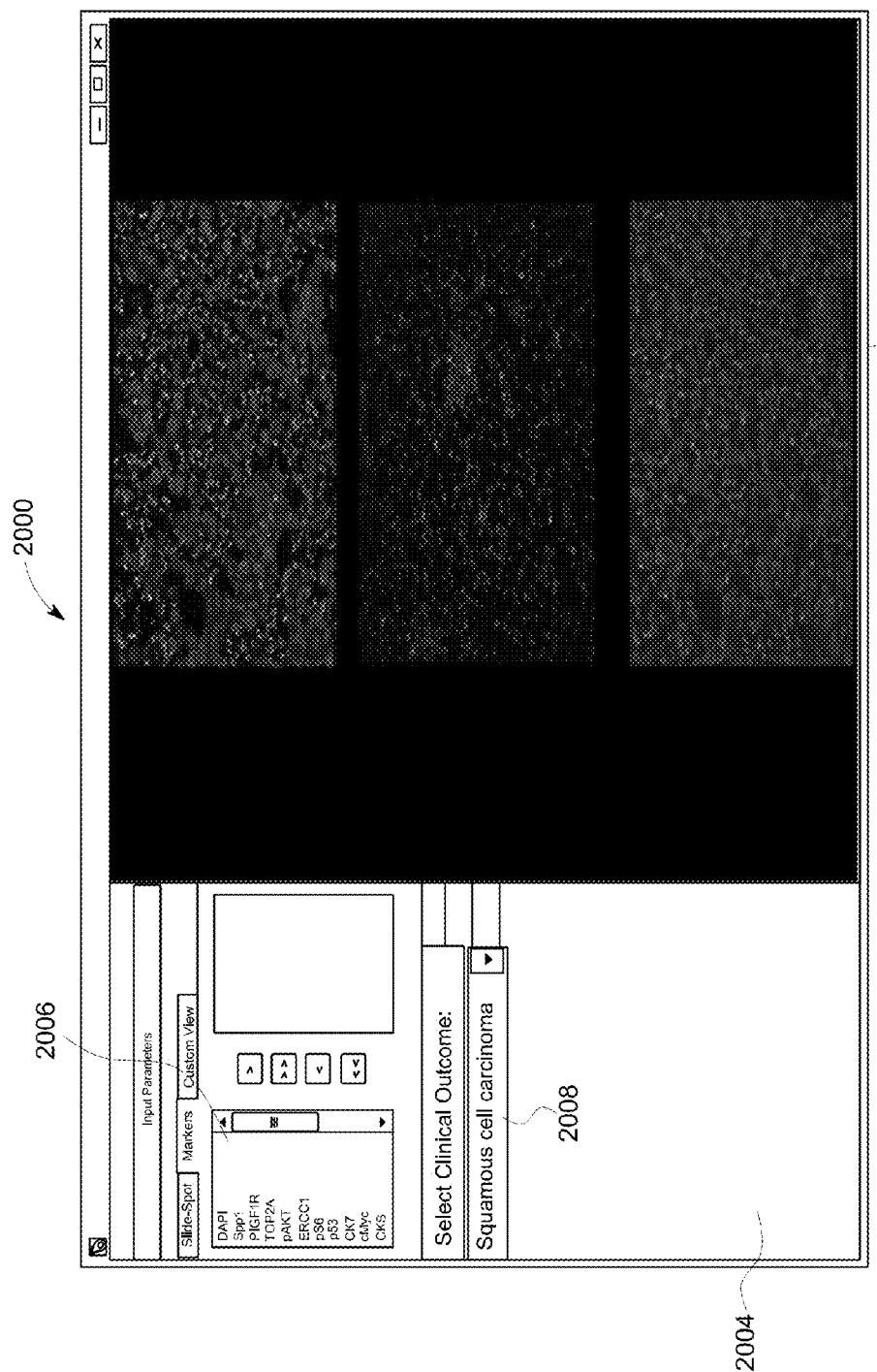
FIG. 20 illustrates an exemplary user interface allowing selection of a marker and a clinical outcome.

Exemplary user interfaces are illustrated in FIGS. 20-23. FIG. 20 illustrates an exemplary user interface 2000 that enables a user to determine a positive or negative correlation between a clinical outcome and expression levels of one or more biomarkers in biological tissue of a cohort. The exemplary user interface 2000 may enable a user to select, directly on the user interface, a field-of-view of biological tissue for display on the user interface. The ability to select particular studies/experiments, slides, spots and biomarkers using the tools provided on the user interface makes it unnecessary for a user to remember the locations of the files related to the studies/experiments, slides, spots and biomarkers, and enables the user to select data sources in an intuitive, time-efficient and user-friendly manner.

The user interface 2000 may include a display panel 2002 for displaying one or more fields-of-view of biological tissue. In the example of FIG. 20, the display panel 2002 displays three exemplary fields-of-view of biological tissue that are overlaid or displayed separately. Each of the fields-of-view may display expression levels of one or more biomarkers. The different fields-of-view may correspond to different spots on the same slide or spots on different slides.

The user interface 2000 may include a selection panel 2004 having a marker selection component 2006 that enables a user to select one or more markers whose expression levels are displayed in the display panel 2002. Additionally or alternatively, exemplary embodiments may enable a user to select biomarkers and high and/or low thresholds to be used in an analysis of a possible correlation with a clinical outcome. For example, the user may perform a correlation analysis between a clinical outcome and high expression levels of one or more biomarkers and/or low expression levels of one or more biomarkers.

In response to the selection of one or more markers, in an exemplary embodiment, the user interface may display or highlight the selected markers in the display panel 2002. In an exemplary embodiment, the user interface may remove the display of expression levels of all markers except the selected markers. In another exemplary embodiment, the user interface may highlight expression levels of the selected markers, for example, by representing their expression levels using higher intensities or using specific colors.

The selection panel 2004 may also include a clinical outcome selection component 2008 for allowing a user to select one or more clinical outcomes that may be associated with the biological tissue displayed in the display panel 2002. In an exemplary embodiment, in response to the selection of one or more clinical outcomes, the user interface 2000 may display which fields-of-view in the display panel 2002 are associated with the selected clinical outcomes, for example, in a database. For example, in response to the selection of the clinical outcome of breast cancer, the user interface 2000 may display fields-of-view of breast tissue that correspond to patients in a cohort having breast cancer. One of ordinary skill in the art will recognize that any suitable patient cohort may be used in exemplary embodiments including, but not limited to, a cohort of patients in the same stage of a disease, a cohort of patients having the same disease outcome, and the like.

In response to the selection of the one or more markers and a clinical outcome, exemplary embodiments may automatically perform a correlation analysis between the clinical outcome and expression levels of the markers in biological tissue for a cohort of patients. In an exemplary embodiment, the automatic correlation may be performed by a separate computing or processing module than the module generating and managing the user interface that displays the markers. Exemplary embodiments may access biological tissue data corresponding to the cohort to which the selected field-of-view belongs. For example, if the user-selected field-of-view corresponds to a first biological tissue sample of a first patient with breast cancer, exemplary embodiments may access data corresponding to multiple biological tissue samples corresponding to a patient cohort including the first patient and one or more other patients with breast cancer. Exemplary embodiments may retrieve biomarker expression data for the cohort corresponding to the selected biomarkers. Exemplary embodiments may then automatically perform correlation analysis between the selected clinical outcome and the biomarker expression data for the cohort. The correlation analysis may be used to determine whether a positive correlation or a negative correlation exists between the selected clinical outcome and the selected biomarkers for the cohort.

For example, exemplary embodiments may determine whether high or low expressions of one or more biomarkers are correlated with a clinical outcome. In one example, upon selection of a positive diagnosis of squamous cell carcinoma (as the clinical outcome) and biomarkers SLC7A5, TRIM29 and CK5/6 (as the aspects of the fields-of-view), exemplary embodiments may automatically determine whether the clinical outcome is positively correlated with high expression levels of the biomarkers. In another example, upon selection of a positive diagnosis of adenocarcinoma (as the clinical outcome) and biomarkers CEACAM5 and MUC1 (as the aspects of the fields-of-view), exemplary embodiments may automatically determine whether the clinical outcome is positively correlated with high expression levels of the biomarkers. In another example, upon selection of squamous cell carcinoma (as the clinical outcome) and biomarkers SLC7A5, TRIM29, CK5/6, CEACAM5 and MUC1 (as the aspects of the fields-of-view), exemplary embodiments may automatically determine whether the clinical outcome is positively correlated with high expression levels of all biomarkers but only when the high expression levels are collocated within the same cells.

Exemplary embodiments may store, in a database or storage device, and display, in the user interface, results of the correlation analysis between the selected clinical outcome and expression levels of the one or more selected biomarkers in the cohort associated with the selected field-of-view.

In another exemplary embodiment, a correlation analysis may be performed between a clinical outcome and one or more features characteristic of one or more user-selected biological units (e.g., cells). In an exemplary embodiment, one or more biological units may be selected randomly, based on certain morphological characteristics, based on biomarker expression levels, based on DNA sequence expression or non-expression, based on location in biological tissue, and the like. In one example, exemplary embodiments may determine whether certain types of user-selected cells are correlated with a disease diagnosis. In another example, exemplary embodiments may determine that cells having high or low expression levels of certain biomarkers are correlated with a disease diagnosis. In another example, exemplary embodiments may determine whether cells located in a selected region of biological tissue are correlated with a disease diagnosis. In another example, exemplary embodiments may determine whether cells having certain morphological characteristics are correlated with a disease diagnosis. In another exemplary embodiment, one or more biological units may be selected for performing a correlation analysis based on a hypothesis generated based on biological knowledge.

Figure 21:
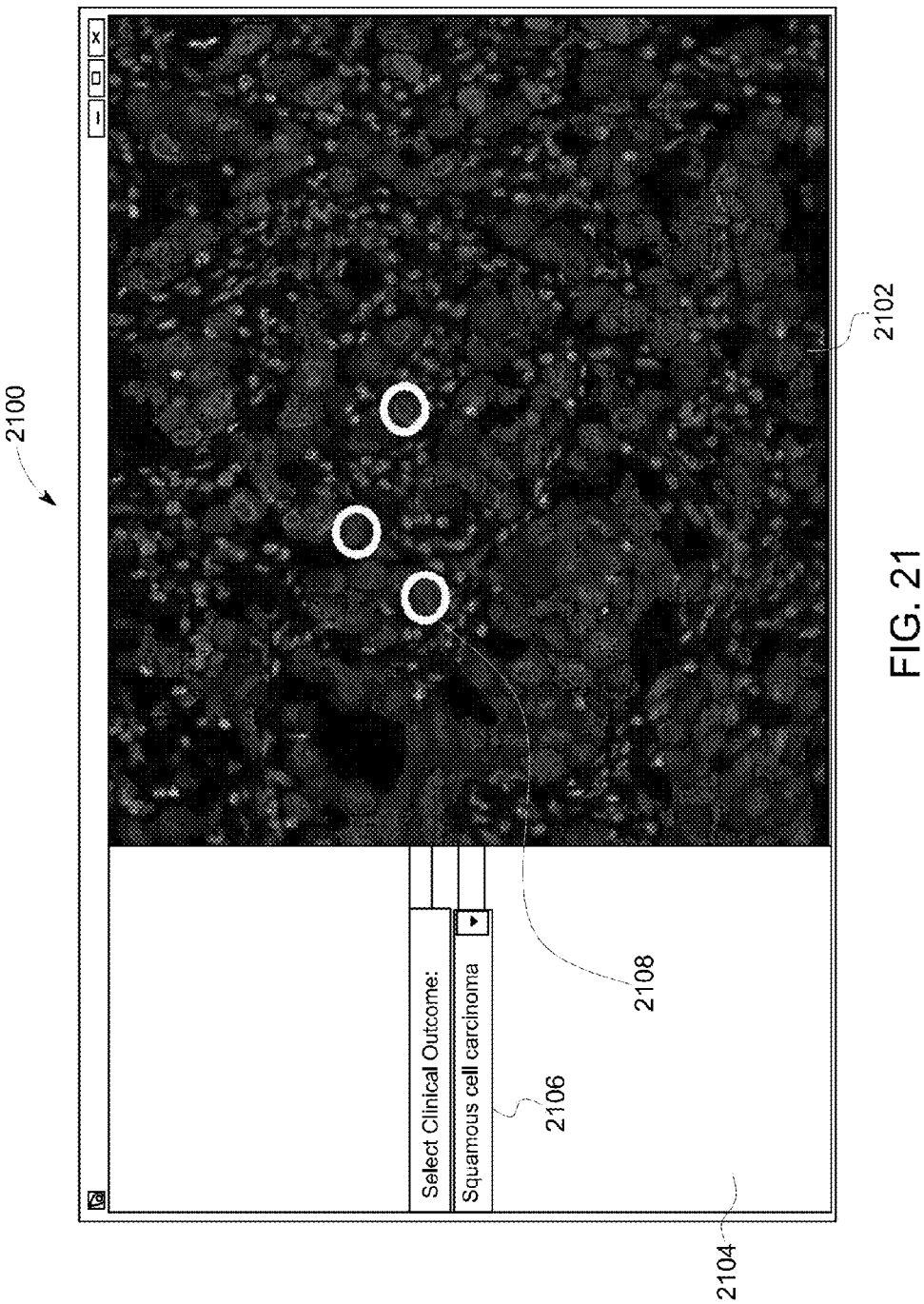
FIG. 21 illustrates an exemplary user interface allowing selection of biological units and a clinical outcome.

FIG. 21 illustrates an exemplary user interface 2100 that enables a user to determine a positive or negative correlation between a clinical outcome and one or more features characteristic of one or more biological units in biological tissue of a cohort. The exemplary user interface 2100 may enable a user to select, directly on the user interface, a field-of-view of biological tissue for display on the user interface. The ability to select particular studies/experiments, slides, spots and biomarkers using the tools provided on the user interface makes it unnecessary for a user to remember the locations of the files related to the studies/experiments, slides, spots and biomarkers, and enables the user to select data sources in an intuitive, time-efficient and user-friendly manner.

The user interface 2100 may include a display panel 2102 for displaying one or more fields-of-view of biological tissue. The field-of-view rendered in the display panel 2102 may display selectable biological units and expression levels of one or more biomarkers in the biological units. A user may directly select one or more biological units (for example, cell 2108) directly in the display panel 2102. In an exemplary embodiment, the user may use a pointing device, for example, a mouse, to click on and select individual biological units, to draw an area on the display panel 2102 to select all of the biological units falling the area, and the like. In an exemplary embodiment, the user may use a different selection option to select the biological units, for example, by selecting units from a drop-down list of biological units, by selecting biological units by filtering them based on one or more morphological characteristics, and the like. In an exemplary embodiment, in response to the selection of one or more biological units, in an exemplary embodiment, the user interface may selectively display or highlight the selected biological units in the display panel 2102.

The selection panel 2104 may also include a clinical outcome selection component 2106 for allowing a user to select one or more clinical outcomes that may be associated with the biological tissue displayed in the display panel 2102. In an exemplary embodiment, in response to the selection of one or more clinical outcomes, the user interface 2100 may display which fields-of-view in the display panel 2102 are associated with the selected clinical outcomes, for example, in a database. For example, in response to the selection of the clinical outcome of breast cancer, the user interface 2100 may display fields-of-view of breast tissue that correspond to patients in a cohort having breast cancer.

In response to the selection of the one or more biological units and a clinical outcome, exemplary embodiments may automatically perform a correlation analysis between the clinical outcome and one or more features characteristic of the selected units in biological tissue for a cohort of patients. Exemplary embodiments may access biological tissue data corresponding to the cohort to which the selected field-of-view belongs. For example, if the user-selected field-of-view corresponds to a first biological tissue sample of a first patient with breast cancer, exemplary embodiments may access data corresponding to multiple biological tissue samples corresponding to a patient cohort including the first patient and one or more other patients with breast cancer.

Exemplary embodiments may retrieve data for the cohort corresponding to features characteristic of the selected biological units. Characteristics of the biological units may include, but are not limited to, one or more morphological characteristics, one or more functional characteristics, one or more biomarker expression levels, one or more locations in biological tissue, one or more types of cells, and the like. For example, if the user-selected biological units are cells having an abnormally large size, exemplary embodiments may retrieve data for the cohort indicating the cell sizes of biological tissue of the cohort. Exemplary embodiments may then automatically perform correlation analysis between the selected clinical outcome and the data for the cohort corresponding to features characteristic of the selected biological units. The correlation analysis may be used to determine whether a positive correlation or a negative correlation exists between the selected clinical outcome and the features characteristic of the selected biological units for the cohort.

Exemplary embodiments may store, in a database or storage device, and display, in the user interface, results of the correlation analysis between the selected clinical outcome and one or more features characteristic of the one or more selected biological units for the cohort. One exemplary embodiment may calculate and store, in a database or storage device, and display, in the user interface, results of the correlation analysis.

In another exemplary embodiment, a correlation analysis may be performed between a clinical outcome and one or more features characteristic of biological units (e.g., cells) rendered in one or more user-selected regions of a field-of-view of biological tissue. A user may select one or more regions of a field-of-view of the biological tissue. One or more features characteristic of the biological units rendered in the selected regions may be automatically analyzed by exemplary embodiments. Exemplary characteristics analyzed may include, but are not limited to, one or more morphological characteristics, one or more functional characteristics, one or more biomarker expression levels, one or more locations in biological tissue, one or more types of cells, and the like.

Figure 22:
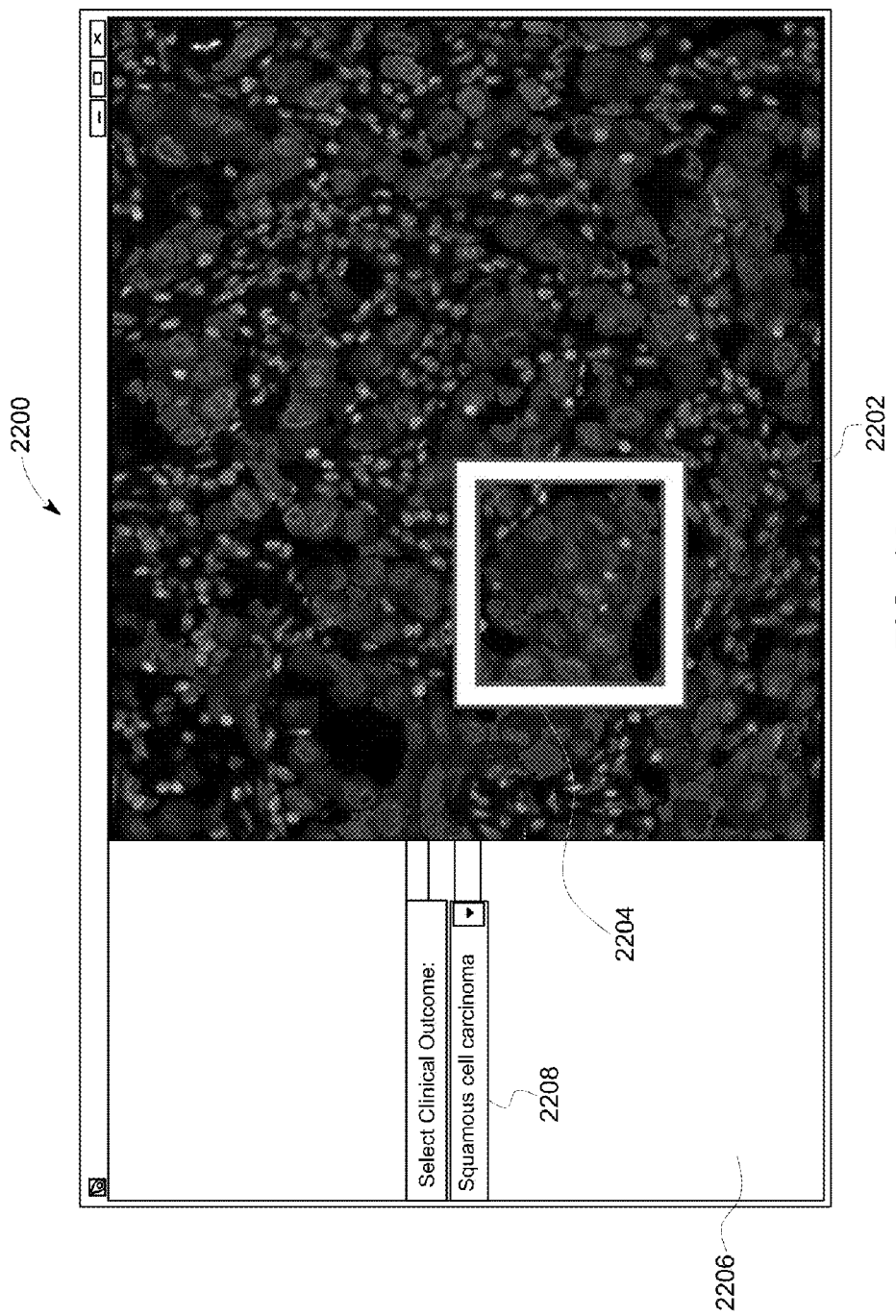
FIG. 22 illustrates an exemplary user interface allowing selection of a region in an image and a clinical outcome.

FIG. 22 illustrates an exemplary user interface 2200 that enables a user to determine a positive or negative correlation between a clinical outcome and one or more features characteristic of biological units falling in one or more user-selected regions of a field-of-view. The exemplary user interface 2200 may enable a user to select, directly on the user interface, a field-of-view of biological tissue for display on the user interface. The ability to select particular studies/experiments, slides, spots and biomarkers using the tools provided on the user interface makes it unnecessary for a user to remember the locations of the files related to the studies/experiments, slides, spots and biomarkers, and enables the user to select data sources in an intuitive, time-efficient and user-friendly manner.

The user interface 2200 may include a display panel 2202 for displaying one or more fields-of-view of biological tissue. The field-of-view rendered in the display panel 2202 may display biological units and expression levels of one or more biomarkers in the biological units. A user may directly select one or more regions (for example, region 2204) directly in the display panel 2202. In an exemplary embodiment, the user may use a pointing device, for example, a mouse, to draw an area on the display panel 2202 to select all of the biological units falling the area, and the like. In an exemplary embodiment, the user may use a different selection option to select the biological units, for example, by selecting coordinates in the field-of-view in input text boxes. In response to the selection of one or more regions in the field-of-view, in an exemplary embodiment, the user interface may selectively display or highlight the biological units falling in the selected region in the display panel 2202.

The selection panel 2206 may also include a clinical outcome selection component 2208 for allowing a user to select one or more clinical outcomes that may be associated with the biological tissue displayed in the display panel 2202. In an exemplary embodiment, in response to the selection of one or more clinical outcomes, the user interface 2200 may display which fields-of-view in the display panel 2202 are associated with the selected clinical outcomes, for example, in a database. For example, in response to the selection of the clinical outcome of breast cancer, the user interface 2200 may display fields-of-view of breast tissue that correspond to patients in a cohort having breast cancer.

In response to the selection of the one or more regions in the field-of-view and a clinical outcome, exemplary embodiments may automatically perform a correlation analysis between the clinical outcome and one or more features characteristic of the biological units falling in the user-selected regions for a cohort of patients. Exemplary embodiments may access biological tissue data corresponding to the cohort to which the selected field-of-view belongs. For example, if the user-selected field-of-view corresponds to a first biological tissue sample of a first patient with breast cancer, exemplary embodiments may access data corresponding to multiple biological tissue samples corresponding to a patient cohort including the first patient and one or more other patients with breast cancer.

Exemplary embodiments may retrieve data for the cohort corresponding to features characteristic of the biological units falling in the user-selected regions of the field-of-view. Characteristics of the biological units may include, but are not limited to, one or more morphological characteristics, one or more functional characteristics, one or more biomarker expression levels, one or more locations in biological tissue, one or more types of cells, and the like. For example, if the biological units in a user-selected region are cells having an abnormally large size, exemplary embodiments may retrieve data for the cohort indicating the cell sizes of biological tissue of the cohort. Exemplary embodiments may then automatically perform correlation analysis between the selected clinical outcome and the data for the cohort corresponding to features characteristic of the biological units. The correlation analysis may be used to determine whether a positive correlation or a negative correlation exists between the selected clinical outcome and the features characteristic of the biological units for the cohort.

Exemplary embodiments may store, in a database or storage device, and display, in the user interface, results of the correlation analysis between the selected clinical outcome and one or more features characteristic of the one or more biological units for the cohort. One exemplary embodiment may calculate and store, in a database or storage device, and display, in the user interface, results of the correlation analysis.

In another exemplary embodiment, a correlation analysis may be performed between a clinical outcome and one or more selected morphological characteristics of biological units (e.g., cells). Exemplary morphological characteristics may include, but are not limited to, cell size, nucleus size, cell eccentricity, and the like.

Figure 23:
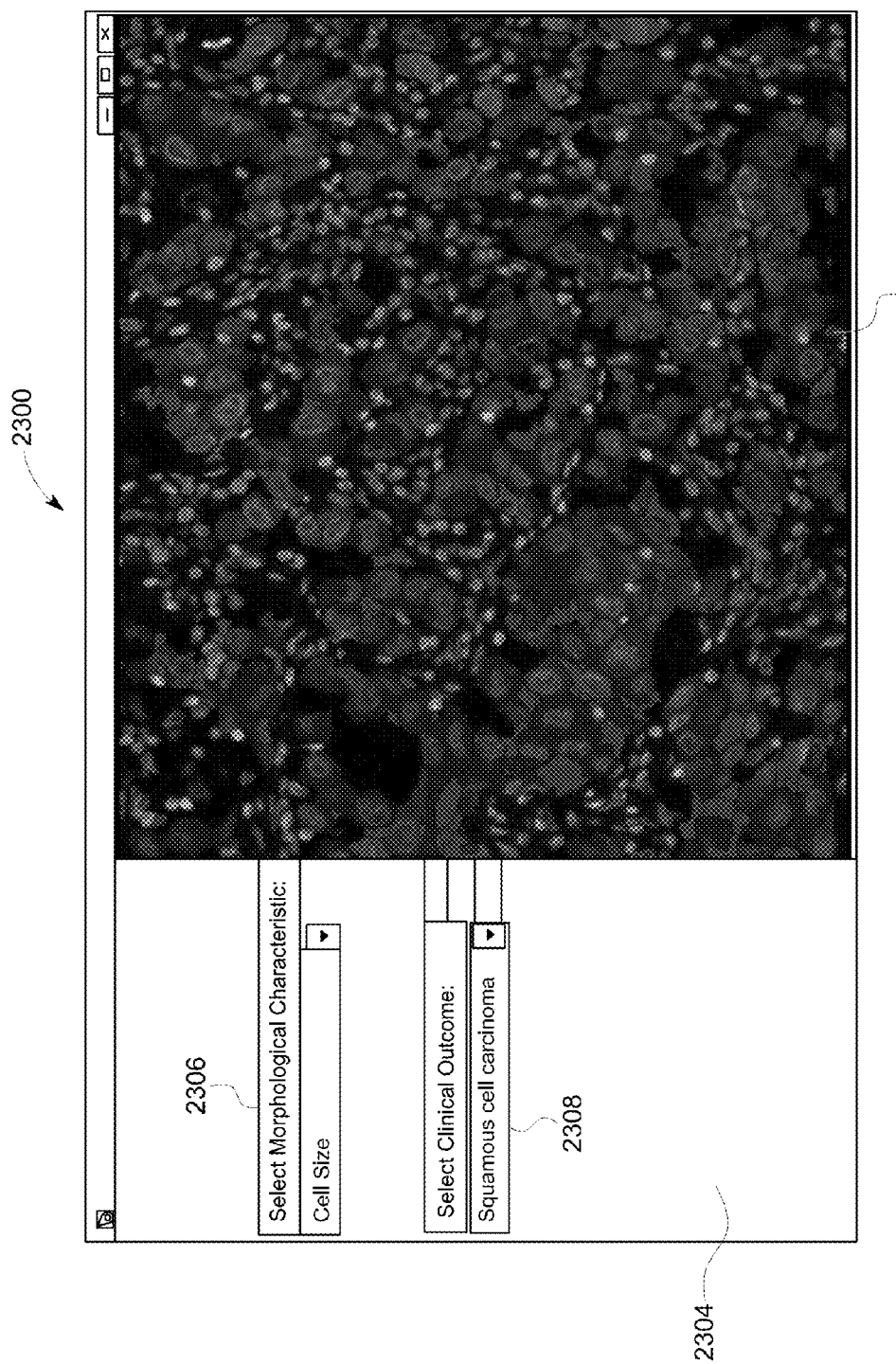
FIG. 23 illustrates an exemplary user interface allowing selection of a morphological characteristic of biological units and a clinical outcome.

FIG. 23 illustrates an exemplary user interface 2300 that enables a user to determine a positive or negative correlation between a clinical outcome and the selected morphological characteristics in biological tissue of a cohort. The exemplary user interface 2300 may enable a user to select, directly on the user interface, a field-of-view of biological tissue for display on the user interface. The ability to select particular studies/experiments, slides, spots and biomarkers using the tools provided on the user interface makes it unnecessary for a user to remember the locations of the files related to the studies/experiments, slides, spots and biomarkers, and enables the user to select data sources in an intuitive, time-efficient and user-friendly manner.

The user interface 2300 may include a display panel 2302 for displaying one or more fields-of-view of biological tissue. A selection panel 2304 may include a morphological characteristic selection component 2306 for allowing a user to select one or more morphological characteristics of biological units displayed in at least one field-of-view in the display panel 2302.

The selection panel 2304 may also include a clinical outcome selection component 2308 for allowing a user to select one or more clinical outcomes that may be associated with the biological tissue displayed in the display panel 2302. In an exemplary embodiment, in response to the selection of one or more clinical outcomes, the user interface 2300 may display which fields-of-view in the display panel 2302 are associated with the selected clinical outcomes, for example, in a database. For example, in response to the selection of the clinical outcome of breast cancer, the user interface 2300 may display fields-of-view of breast tissue that correspond to patients in a cohort having breast cancer.

In response to the selection of the one or more morphological characteristics and a clinical outcome, exemplary embodiments may automatically perform a correlation analysis between the clinical outcome and morphological characteristics of biological tissue for a cohort of patients. Exemplary embodiments may access biological tissue data corresponding to the cohort.

Exemplary embodiments may retrieve data for the cohort corresponding to the user-selected morphological characteristics. For example, if the user-selected morphological characteristic is an abnormally large size of cells, exemplary embodiments may retrieve data for the cohort indicating the cell sizes of biological tissue of the cohort. Exemplary embodiments may then automatically perform correlation analysis between the selected clinical outcome and the data for the cohort corresponding to the user-selected morphological characteristics. The correlation analysis may be used to determine whether a positive correlation or a negative correlation exists between the selected clinical outcome and the user-selected morphological characteristics of the selected biological units for the cohort.

Exemplary embodiments may store, in a database or storage device, and display, in the user interface, results of the correlation analysis between the selected clinical outcome and the morphological characteristics. One exemplary embodiment may calculate and store, in a database or storage device, and display, in the user interface, results of the correlation analysis.

One of ordinary skill in the art will recognize that any combinations of a plurality of aspects of a field-of-view may be used in determining their correlation with a clinical outcome.

Figure 24A:
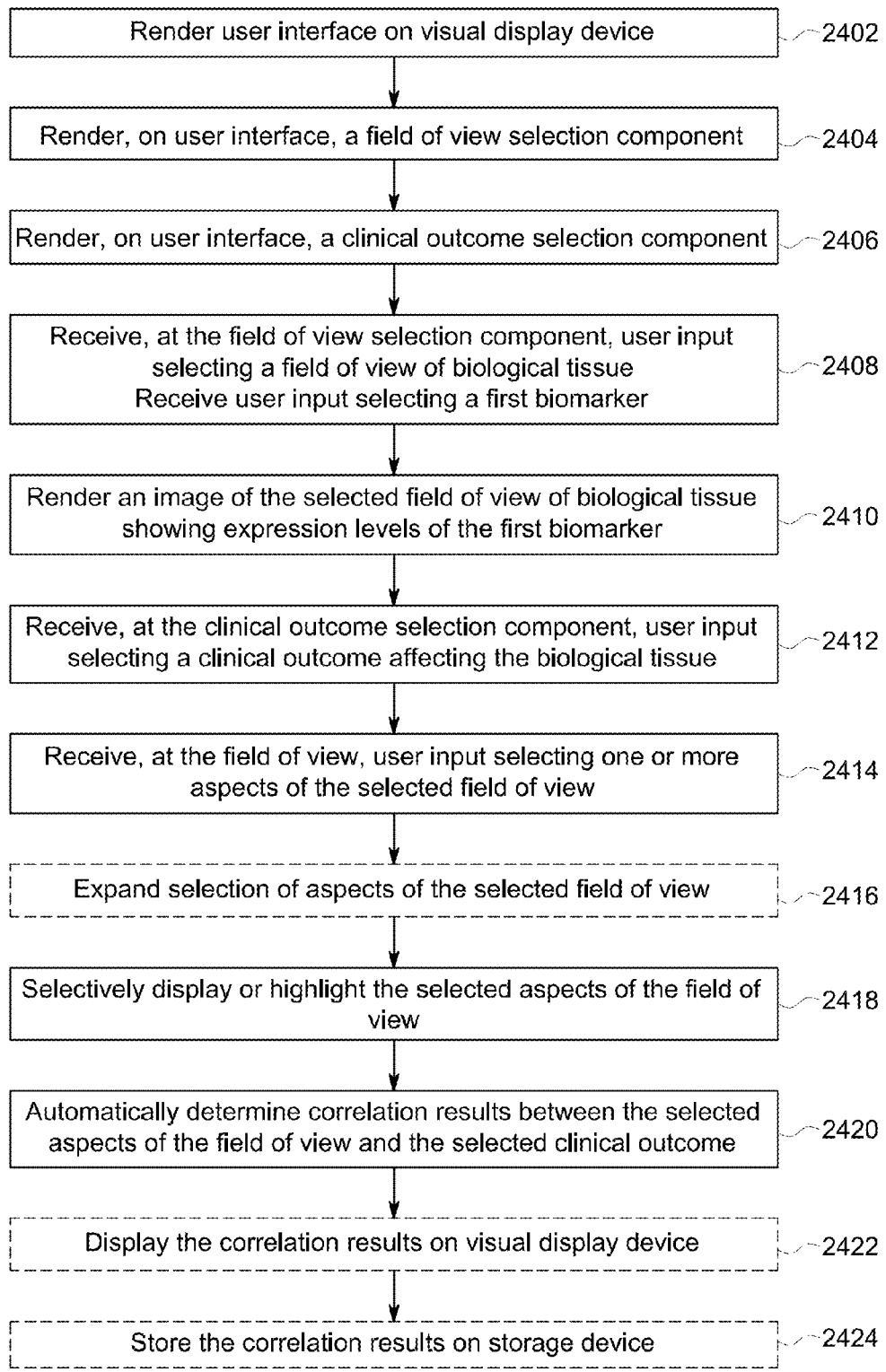
FIG. 24A is a flowchart of a method for determining a positive or negative correlation between a clinical outcome and one or more features in a selection based on a field-of-view of biological tissue.

FIG. 24A is a flowchart of a method for determining a positive or negative correlation between a clinical outcome and one or more features in a selection in a field-of-view of biological tissue.

In step 2402, a graphical user interface may be rendered on a visual display device.

In step 2404, a field-of-view selection component may be rendered on the graphical user interface. The field-of-view selection component allows a user to select a field-of-view of biological tissue from a data set including tissue profile data. The tissue profile data in the data set may include multiplexed biomarker images capturing expression of one or more biomarkers displayed in an overlaid manner in one or more fields-of-view of biological tissue. Any number of biomarker expression overlays may be displayed in the same field-of-view including, but not limited to, 1, 2, 3 4, 5, 6, 7, 8, 9, 10, 11, 12, 13, 14, 15, 16, 17, 18, 19, and 20. The expression levels of different biomarkers in the different overlays may be displayed in different colors to prevent confusion and to make the biomarker levels visually distinguishable from one another.

In step 2406, a clinical outcome selection component may be rendered on the graphical user interface to allow a user to select a clinical outcome associated with the biological tissue displayed in the user interface.

In step 2408, the user interface may receive, at the field-of-view selection component, user input selecting a field-of-view of biological tissue. The user interface may also receive user input selecting one or more biomarkers whose expression levels are to be displayed in the selected field-of-view of the biological tissue.

In step 2410, in response to the user input, the user interface may render an image of the selected field-of-view of biological tissue in which expression levels of the selected one or more biomarkers are shown as intensities of one or more corresponding colors.

In step 2412, the user interface may receive, at the clinical outcome selection component, user input selecting a clinical outcome, for example, positive diagnosis of a disease or tissue condition, negative diagnosis of a disease or tissue condition, a disease prognosis, a prediction of drug response, stratification into a clinically-relevant group, and the like.

In step 2414, in an exemplary embodiment, the user interface may receive user input selecting one or more aspects of the field-of-view displayed in the user interface. Exemplary selectable aspects of the field-of-view may include, but are not limited to, one or more biological units, one or more regions in the field-of-view, one or more morphological characteristics, one or more functional characteristics, one or more biomarkers, one or more DNA sequences, and the like.

In another exemplary embodiment, the aspects of the field-of-view may be selected automatically, for example, by a clustering method or algorithm encoded on one or more non-transitory computer-readable media and implemented as computer-executable instructions that cluster the aspects. For example, a clustering method may automatically select one or more biological units (e.g., cells, sub-cellular components, etc.) that are clustered based on one or more common features. These common features may include, but are not limited to, similar expression levels of one or more biomarkers, similar or identical morphological characteristics of the biological units, similar or identical functional characteristics of the biological units, combinations of any of the aforementioned features, certain common regions of the biological tissue, and the like.

In step 2416, in an exemplary embodiment, the selection of the aspects of the field-of-view may be automatically expanded using a supervised learning method or algorithm encoded on one or more non-transitory computer-readable media and implemented as computer-executable instructions. A supervised learning method may expand the selection of the aspects of the field-of-view by including one or more additional aspects in the same data cohort having one or more similar features. For example, if the user selects one or more biological units, exemplary embodiments may expand the selection with one or more additional biological units in the cohort having one or more similar features as in the user-selected biological units.

In step 2418, the user interface may selectively display or highlight the aspects of the field-of-view selected in step 2414 or the expanded selection of step 2416. In an exemplary embodiment, if a set of biological units (e.g., cells) is selected, the user interface may highlight the selected cells, for example, using higher color intensities to represent biomarker expression levels in the selected cells.

In step 2420, exemplary embodiments may automatically perform a correlation analysis between the selected clinical outcome and data for a cohort of patients corresponding to the selected aspects of the field-of-view. In an exemplary embodiment, if a set of biological units (e.g., cells) is selected, exemplary embodiments may determine whether the selected clinical outcome is correlated with one or more features characteristic of the biological units in data for the cohort.

In step 2422, exemplary embodiments may display the results of the correlation analysis on the user interface rendered on the visual display device.

In step 2424, exemplary embodiments may store the results of the correlation analysis in a database or a storage device.

Figure 24B:
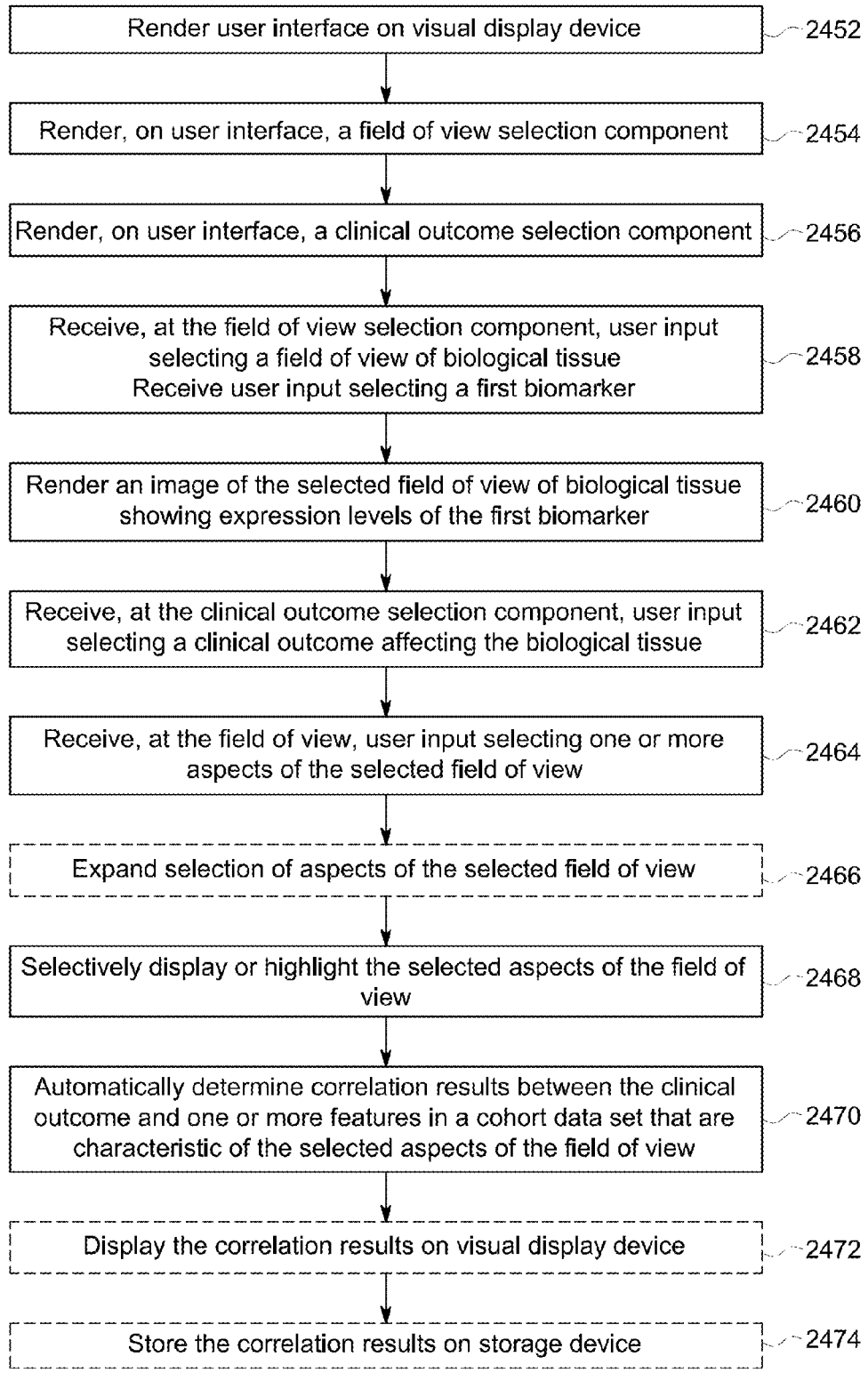
FIG. 24B is a flowchart of a method for determining a positive or negative correlation between a clinical outcome and one or more features in a cohort data set that are characteristic of a selection based in a field-of-view of biological tissue.

FIG. 24B is a flowchart of a method for determining a positive or negative correlation between a clinical outcome and one or more features in a cohort data set that are characteristic of a selection performed in a field-of-view of biological tissue.

In step 2452, a graphical user interface may be rendered on a visual display device.

In step 2454, a field-of-view selection component may be rendered on the graphical user interface. The field-of-view selection component allows a user to select a field-of-view of biological tissue from a data set of a cohort including tissue profile data. The tissue profile data in the data set may include multiplexed biomarker images capturing expression of one or more biomarkers displayed in an overlaid manner in one or more fields-of-view of biological tissue. Any number of biomarker expression overlays may be displayed in the same field-of-view including, but not limited to, 1, 2, 3 4, 5, 6, 7, 8, 9, 10, 11, 12, 13, 14, 15, 16, 17, 18, 19, 20, and the like. The expression levels of different biomarkers in the different overlays may be displayed in different colors to prevent confusion and to make the biomarker levels visually distinguishable from one another.

In step 2456, a clinical outcome selection component may be rendered on the graphical user interface to allow a user to select a clinical outcome associated with the biological tissue displayed in the user interface.

In step 2458, the user interface may receive, at the field-of-view selection component, user input selecting a field-of-view of biological tissue. The user interface may also receive user input selection one or more biomarkers whose expression levels are to be displayed in the selected field-of-view of the biological tissue.

In step 2460, in response to the user input, the user interface may render an image of the selected field-of-view of biological tissue in which expression levels of the selected one of more biomarkers are shown as intensities of one or more corresponding colors.

In step 2462, the user interface may receive, at the clinical outcome selection component, user input selecting a clinical outcome, for example, positive diagnosis of a disease or tissue condition, negative diagnosis of a disease or tissue condition, a disease prognosis, a prediction of drug response, stratification into a clinically-relevant group, and the like.

In step 2464, in an exemplary embodiment, the user interface may receive user input selecting one or more aspects of the field-of-view displayed in the user interface. Exemplary selectable aspects of the field-of-view may include, but are not limited to, one or more biological units, one or more regions in the field-of-view, one or more morphological characteristics, one or more functional characteristics, one or more biomarkers, one or more DNA sequences, and the like.

In another exemplary embodiment, the aspects of the field-of-view may be selected automatically, for example, by a clustering method or algorithm encoded on one or more non-transitory computer-readable media and implemented as computer-executable instructions that cluster the aspects. For example, a clustering method may automatically select one or more biological units (e.g., cells, sub-cellular components, etc.) that are clustered based on one or more common features. These common features may include, but are not limited to, similar expression levels of one or more biomarkers, similar or identical morphological characteristics of the biological units, similar or identical functional characteristics of the biological units, combinations of any of the aforementioned features, certain common regions of the biological tissue, and the like.

In step 2466, in an exemplary embodiment, the selection of the aspects of the field-of-view may be automatically expanded using a supervised learning method or algorithm encoded on one or more non-transitory computer-readable media and implemented as computer-executable instructions. The supervised learning method may expand the selection of the aspects of the field-of-view by including one or more additional aspects in the same data cohort having one or more similar features. For example, if the user selects one or more biological units, exemplary embodiments may expand the selection with one or more additional biological units in the cohort having one or more similar features as in the user-selected biological units.

In step 2468, the user interface may selectively display or highlight the aspects of the field-of-view selected in step 2464 or the expanded selection of step 2466. In an exemplary embodiment, if a set of biological units (e.g., cells) is selected, the user interface may highlight the selected cells, for example, using higher color intensities to represent biomarker expression levels in the selected cells.

In step 2470, upon selection of a clinical outcome and one or more aspects of the field-of-view (for example, a cell type), exemplary embodiments may automatically perform correlation analysis between the selected clinical outcome and data on the selected cell type for an entire cohort of patients. For example, if a cell type is selected in a field-of-view corresponding to a first patient, correlation analysis may be performed against data on the selected cell type for an entire cohort of patients to which the first patient belongs.

In step 2472, exemplary embodiments may display the results of the correlation analysis on the user interface rendered on the visual display device.

In step 2474, exemplary embodiments may store the results of the correlation analysis in a database or a storage device.

Exemplary Quality Scoring of Image Analysis

Exemplary embodiments may provide or configure a user interface to allow a user to perform quality review of image or statistical analysis performed on one or more images of biological tissue. An exemplary user interface displays results of an image analysis method performed on an image of biological tissue in an overlaid manner on an image of biological tissue. The exemplary user interface enable a user to provide, directly on the user interface, one or more quality review scores to indicate the user's assessment of the quality of the image analysis performed on the image. Exemplary embodiments may store the quality review scores provided by the user in association with the image analysis method and the image of biological tissue.

In an exemplary embodiment, one or more images of a selected field-of-view of biological tissue may be rendered on a user interface. In an exemplary embodiment, the user interface may overlay, on the image of the selected field-of-view, one or more results of an image segmentation method performed on the image displayed. Image segmentation is the process of partitioning a digital image into multiple segments, and is typically used to locate objects and boundaries in images. The image segmentation method may process multiplexed biomarker image data corresponding to a field-of-view of biological tissue to generate a set of one or more segments delineating one or more biological units of interest (e.g., cells, sub-cellular components, collections of cells). By overlaying the results of the image segmentation method over the image of the selected field-of-view, the user interface allows a user to assess the results of the image segmentation method and provide quality scores.

Figure 27:
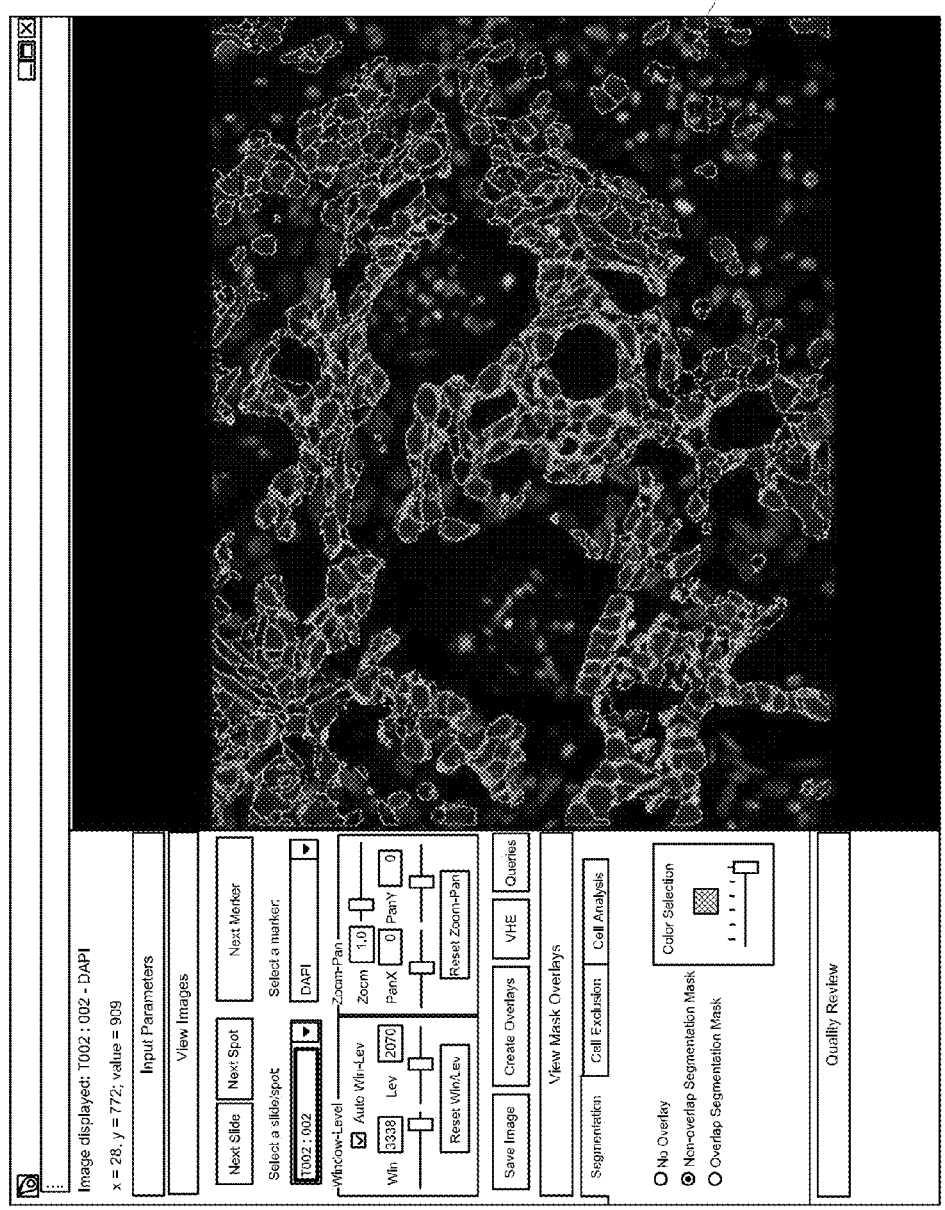
FIG. 27 illustrates an exemplary user interface showing a non-overlapping segmentation mask.
Figure 28:
FIG. 28 illustrates an exemplary user interface showing an overlaid segmentation mask.

Exemplary image segmentation methods may include overlapping or non-overlapping segmentation methods. FIG. 27 shows a user interface in which the results of a non-overlapping segmentation method run on an image of biological tissue are overlaid on the image of biological tissue. FIG. 28 shows a user interface in which the results of a segmentation method run on an image of biological tissue is overlaid on the image of biological tissue.

Figure 25:
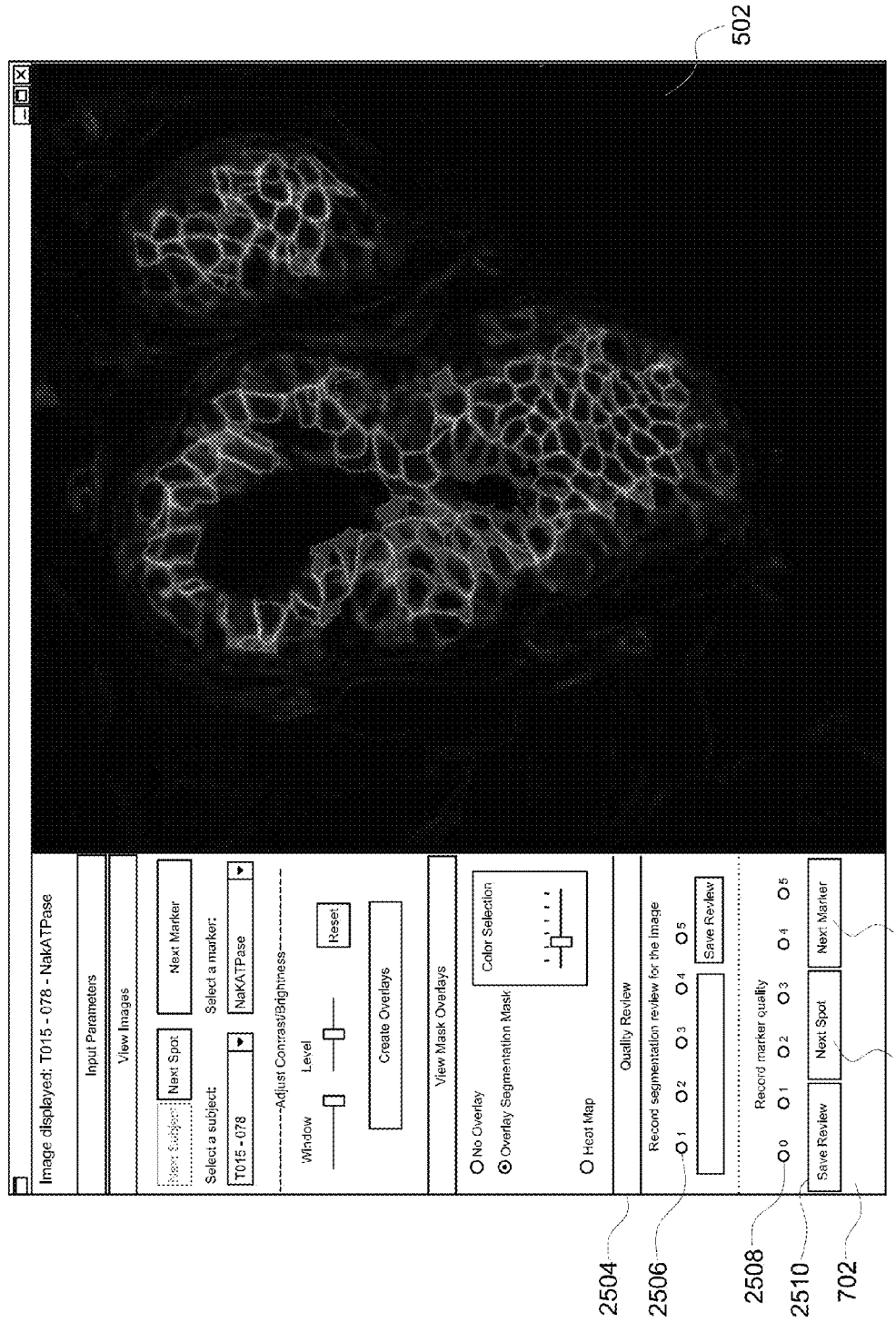
FIG. 25 illustrates an exemplary user interface allowing a user to provide quality scores.

FIG. 25 illustrates an exemplary user interface including a display panel 502 for displaying one or more images of biological tissue and/or one or more results of morphological or statistical analysis, and a selection panel 702. Selection panel 702 is described in connection with FIG. 7 and may allow a user to select one or more image analysis methods in order to display the results of the method in the display panel 502. The selection panel 702 may provide a color selection tool for selecting one or more colors for representing the results of the selected analysis method. For example, the user may specify that cells identified by an image segmentation method be displayed as blue units on the display panel 502. In another example, the user may specify that cell membranes identified by an image segmentation method be displayed as blue lines on the display panel 502.

Figure 26B:
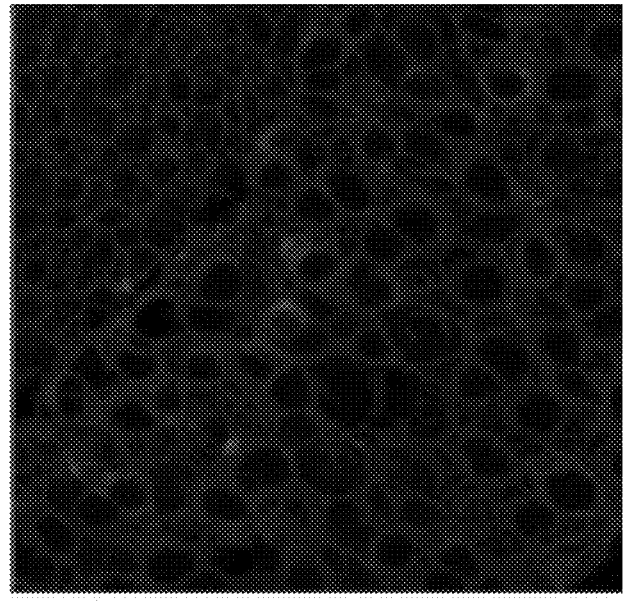
FIGS. 26A and 26B illustrate exemplary image segmentation results overlaid on a background image.
Figure 26A:
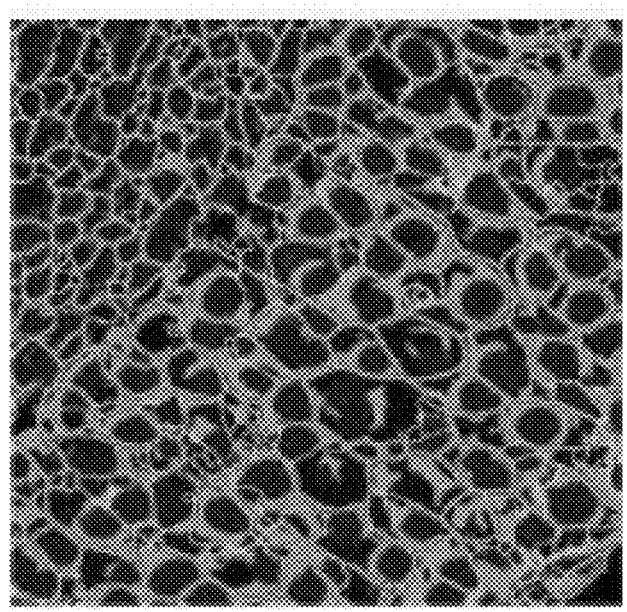

The selection panel 702 may provide a transparency selection tool (e.g., a slider bar slidable between 0% transparency to 100% transparency) for selecting one or more transparency levels for representing the results of the selected morphological analyses. Transparency of an image layer is the extent to which light can pass through the layer so that the underlying layers are partially visible. The extent of visibility of the underlying layers is controlled by the transparency level. For example, the user may specify that the results of a first morphological analysis are to be represented by lines and colors that are at 50% transparency on the image in the display panel 502. FIG. 26A illustrates a segmentation results mask overlaid over a biomarker image at 0% transparency or 100% opacity. FIG. 26B illustrates the segmentation results mask overlaid at 60% transparency or 40% opacity, in which the underlying biomarker image is visible through the segmentation mask.

In an exemplary embodiment, the selection panel 702 may also provide options to select and adjust a contrast and/or a brightness of the overlay of the results of the selected analysis method.

The selection panel 702 may also include a quality review selection component 2504 for allowing a user to provide one or more quality scores. In an exemplary embodiment, the quality review selection component 2504 may include a segmentation quality selection component 2506 that allows a user to provide one or more segmentation quality scores that indicate an evaluation of a performance of the image segmentation method. For example, if the user determines that a location on the image includes a separate cell, but if the result of the image segmentation method does not depict cell membranes in that location, the user may determine that the image segmentation method failed to locate the cell at that location. This may affect the segmentation quality score provided by the user at the quality review selection component on the user interface. In an exemplary embodiment, the user interface may allow a user to directly identify one or more biological units that are incorrectly identified by an image segmentation method on the image. This may allow subsequent review of the results and performance of the image segmentation method.

Exemplary embodiments may automatically determine whether one or more segmentation quality scores, corresponding to a particular image segmentation method performed on one or more images of a particular type of biological tissue, are below a predefined quality threshold. If one or more of the segmentation quality scores are below the quality threshold, exemplary embodiments may make an automatic determination that the particular image segmentation method is unsuitable for processing the type of biological tissue. In this case, an indication may be provided that the image segmentation method is unsuitable for processing images of the type of biological tissue, and needs to be refined and/or replaced.

The quality review selection component 2504 may include a marker quality selection component 2508 that allows a user to provide one or more scores that indicate an evaluation of a quality of a marker used to treat the biological tissue prior to capturing the image of the biological tissue. For example if an image segmentation method is determined to be very suitable for a type of biological tissue, but if the results of the image segmentation method appear inconsistent with a particular image of the type of biological tissue, a user may determine that the biomarker used for treating the biological tissue was unsuitable. This may affect the marker quality score provided by the user at the quality review selection component on the user interface.

Exemplary embodiments may automatically determine whether one or more marker quality scores, corresponding to one or more images obtained by treating biological tissue using a particular marker, are below a predefined quality threshold. If one or more of the marker quality scores are below the quality threshold, exemplary embodiments may determine that the particular marker is unsuitable for treating the type of biological tissue. That is, if a marker is associated with multiple marker quality scores that are poor, this may indicate that the marker is unsuitable for treating the biological tissue. In this case, an indication may be provided that the marker is unsuitable for treating processing the type of biological tissue and needs to be replaced.

The quality review selection component 2504 may include a "Save Review" tool 2510 to allow a user to save one or more quality review scores provided using the quality review selection component. In response, the user interface may send instructions to store the quality review scores on a storage device. In an exemplary embodiment, the quality review scores may be stored in association with the data corresponding to the field-of-view corresponding to the biological tissue and in association with the selected morphological analysis. In an exemplary embodiment, the instruction may indicate that the quality review scores are to be stored in associated with an identification of the user who provided the quality review scores. In this embodiment, the quality review scores may be stored in association with an identification of the user who provided the quality review scores.

Figure 29:
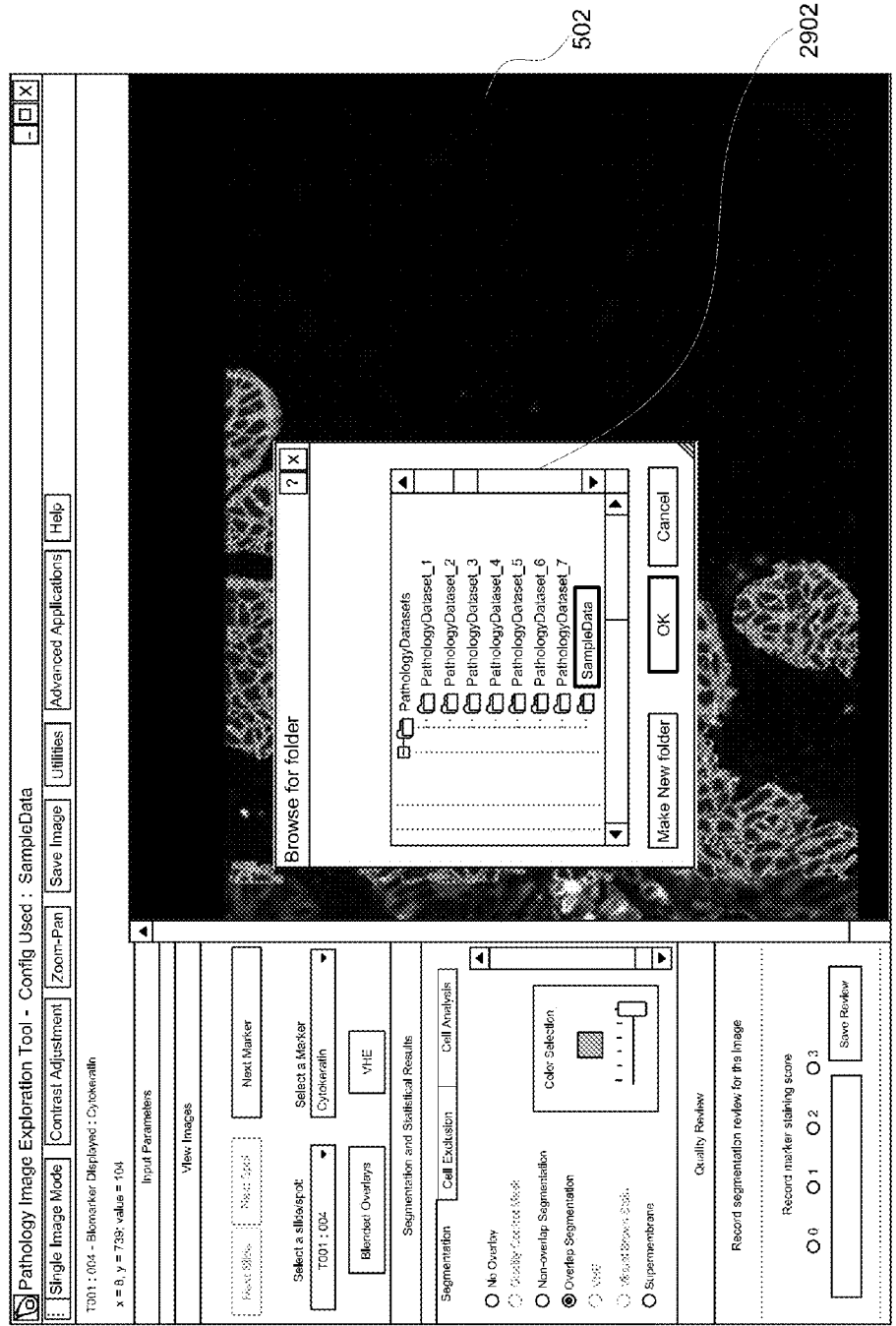
FIG. 29 illustrates an exemplary user interface allowing a user to select a location for saving quality score data.

As illustrated in FIG. 29, upon selecting the "Save Review" tool, a file location selection component 2902 may be displayed on the user interface to allow the user to select a location in a database or file structure for saving the quality review score. If the user fails to select a location in the file location selection component 2902, the quality review score may be saved in a default location.

The quality review selection component 2504 may include a "Next Spot" tool 2512 to allow a user to replace the image displayed in the display panel 502 with the image of a different field-of-view of biological tissue. In addition, if an analysis method is selected, results of the selected analysis performed on the image of the newly selected field-of-view may be automatically overlaid on the display panel 502. The "Next Spot" option 2512 thereby allows a user to assess and provide quality review scores for a plurality of fields-of view of biological tissue in a single session of using the user interface.

The quality review selection component 2504 may also allow a user to load a previously displayed image to adjust one or more quality review scores previously provided to the image. This allows the user the flexibility to re-assess the same image and adjust quality review scores based on the re-assessments.

The quality review selection component 2504 may include a "Next Marker" tool 2514 to allow a user to replace the first image displayed in the display panel 502 with a different image of the same field-of-view of biological tissue obtained by treating the biological tissue with a different biomarker than the biomarker used to obtain the first image. In response to the user input, the user interface may render a second, different image of the selected field-of-view of biological tissue, while continuing to render the representation of the result of the selected morphological analysis such that the second image is overlaid by the representation of the result of the morphological analysis. In an exemplary embodiment, the second image may replace the first image on the user interface. In another exemplary embodiment, the second image result may be overlaid on the first image on the user interface.

Figure 30:
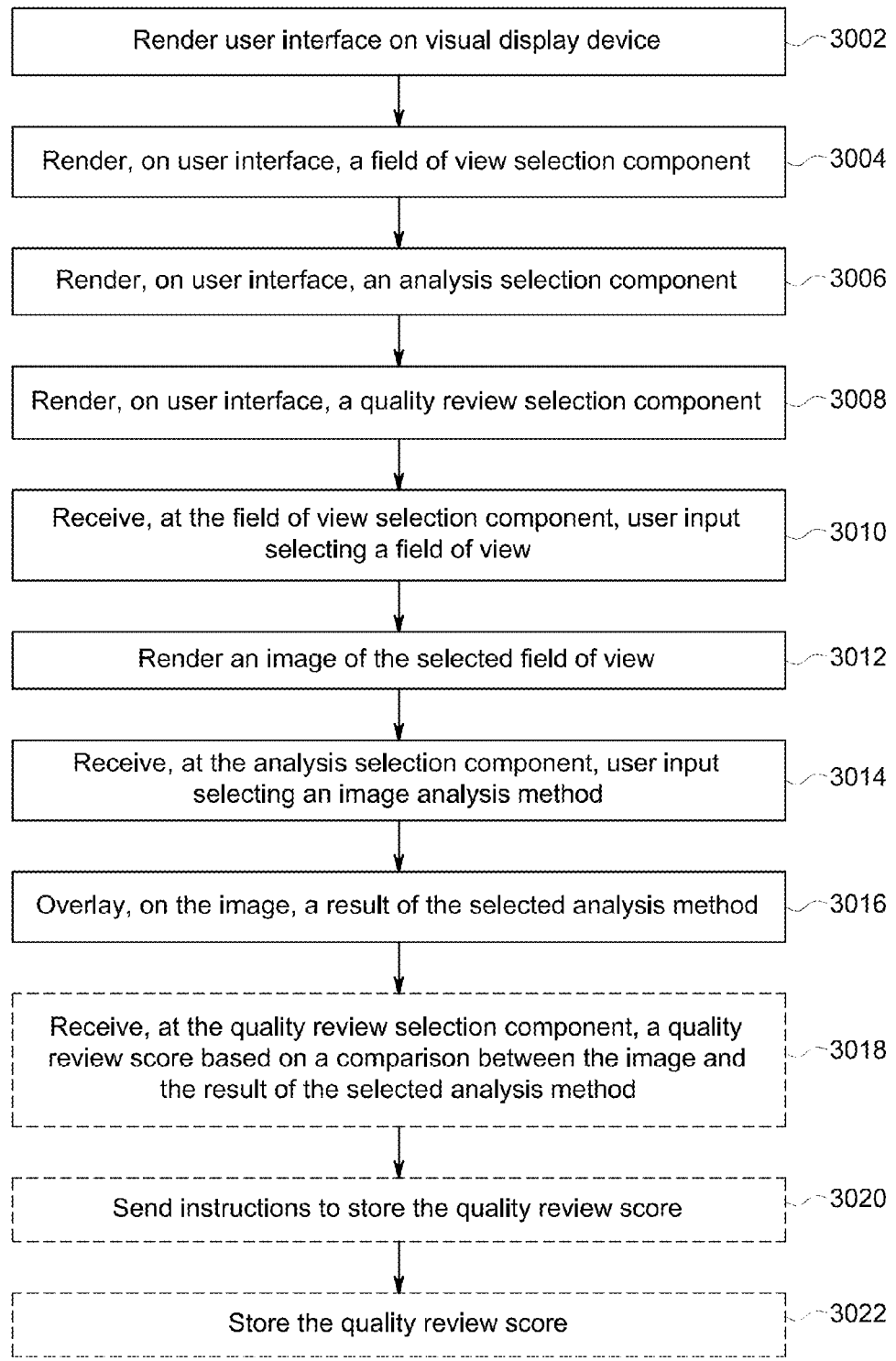
FIG. 30 is a flowchart of an exemplary method for receiving quality scores from a user.

FIG. 30 is a flowchart illustrating an exemplary computer-implemented method performed in exemplary embodiments to allow a user to perform quality review of results of an image analysis method.

In step 3002, a graphical user interface may be rendered on a visual display device.

In step 3004, a field-of-view selection component may be rendered on the graphical user interface. The field-of-view selection component allows a user to select a field-of-view of biological tissue from a data set including tissue profile data. The tissue profile data in the data set may include multiplexed biomarker images capturing expression of one or more biomarkers in a plurality of fields-of-view of biological tissue.

In step 3006, an analysis selection component may be rendered on the graphical user interface to allow a user to select an image analysis method.

In step 3008, a quality review selection component may be rendered on the graphical user interface to allow a user to indicate his/her assessment of the quality of a result of the selected analysis as displayed on the user interface.

In step 3010, the user interface may receive, at the field-of-view selection component, user input selecting a field-of-view of biological tissue. In step 3012, in response to the user input, the user interface may render an image of the selected field-of-view of biological tissue.

In step 3014, the user interface may receive, at the analysis selection component, user input selecting an analysis method, for example, image segmentation. In step 3016, in response to the user input, the user interface may overlay a result of the selected analysis method on the image of the field-of-view of the biological tissue.

In step 3018, in an exemplary embodiment, the user interface may receive, at the quality review selection component, one or more quality review scores provided by a user to indicate his/her assessment of the quality of a result of the selected analysis method.

In step 3020, in an exemplary embodiment, the user interface may send instructions to store the quality review scores on a storage device.

In step 3022, exemplary embodiments may store the quality review scores on a database or storage device.

Exemplary Services Architecture and
Object-Oriented Implementation

Figure 31:
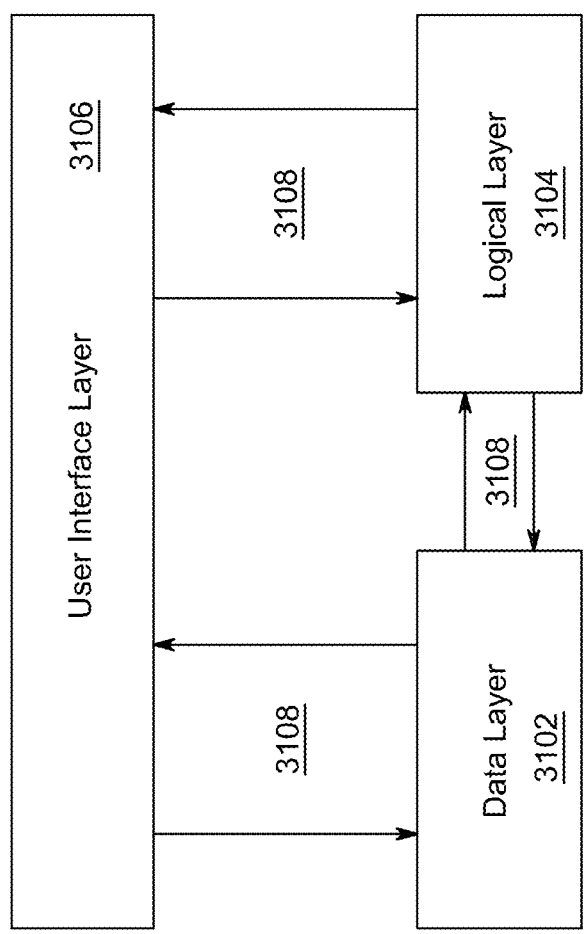
FIG. 31 is a block diagram showing an exemplary services-based architecture providing a data layer, a logical layer and a user interface layer.

Exemplary embodiments may be implemented using a services-based architecture, as illustrated in FIG. 31. An exemplary services-based architecture may include a data layer 3102 for storing image and/or text data associated with multiplexed images of biological tissue, a user interface (UI) layer 3106 for displaying the image and/or text data on a visual display device, and a logical layer 3104 for performing access and processing operations on the data stored in the data layer so that the raw and/or processed data may be displayed using the UI layer. One of ordinary skill in the art will recognize that the services architecture illustrated in FIG. 31 is an illustrative architecture and that exemplary embodiments may be implemented using other suitable services-based architectures.

The data layer may be structured and configured to store large volumes of complex data corresponding to multiple studies, multiple patients and multiple slides and spots. The data layer may be organized so that any user-selected data is accessible in a user-friendly, time-efficient, structured yet flexible manner. The data layer may receive one or more data access requests from the logical layer and/or the UI layer. In response, the data layer may access the requested data in an appropriate database and transmit the requested data to the layer that made the request. The data layer may also perform one or more data manipulation operations including, but not limited to, write, update, delete, aggregate, filtering, and the like. An exemplary data layer may include one or more data storage devices and structures, for example, databases such as object-oriented databases, relational databases, collection of text files, collection of image files, and the like.

The logical layer may include one or more services that are computer-executable instructions, programs or software for accessing data from the data layer and for processing data received from the data layer. Exemplary data processing operations that may be performed by the logical layer may include, but are not limited to, generating image overlays corresponding to a selected field-of-view of biological tissue, generating visualizations of biological units, generating visualizations of biomarker expression levels, generating visualizations of expression of DNA sequences, and the like. The logical layer may receive one or more data access and/or processing requests from the UI layer, and may query the data layer to access necessary data. Upon receiving the requested data from the data layer, the logical layer may perform one or more suitable data processing operations on the data. The logical layer may then transmit the processed data to the UI layer. In some exemplary embodiments, certain services in the logical layer may locate and bind to data sources in the data layer so that data access is maintained in a reliable manner for performing multiple data accesses from the data sources.

The UI layer may include one or more services that are computer-executable instructions, programs or software for providing and managing one or more user interfaces rendered on a visual display device and including human-viewable inputs and outputs. The UI layer may allow a user interface to receive input from a user that specifies parameters of the data to be displayed on the user interfaces. In one example, a user may specify that he/she wishes to view data corresponding to a particular study, a particular slide, a particular spot, and the like. In another example, a user may specify that he/she wishes to view expression levels of one or more biomarkers. In another example, a user may specify that he/she wishes to view expression and non-expression of one or more DNA sequences. In another example, a user may specify that he/she wishes to view biological units that satisfy certain characteristics. In another example, a user may specify that he/she wishes to view results of image segmentation.

The UI layer may receive the user input and may directly request the data layer for data for display in the UI layer. In an exemplary embodiment, the UI layer may request the logical layer for processed data. When the logical layer returns the requested processed data, the UI layer may selectively display the data on one or more user interfaces in a user-friendly manner. In some exemplary embodiments, certain services in the UI layer may locate and bind to services provided by the logical layer.

Communication among the data layer, the logical layer and the UI layer defined in the architecture may be accomplished through a network communication protocol 3108 integrated into each service. The network connection protocol may allow any layer to call the operations and functions provided by any other layer. Any suitable network connection protocol may be used including, but not limited to, TCP/IP, HOP, HTTP, and the like.

In some exemplary embodiments, structures, functions and operations of the data layer, the logical layer and the UI layer may be implemented in a suitable object-oriented programming language, for example, Java.

Figure 32:
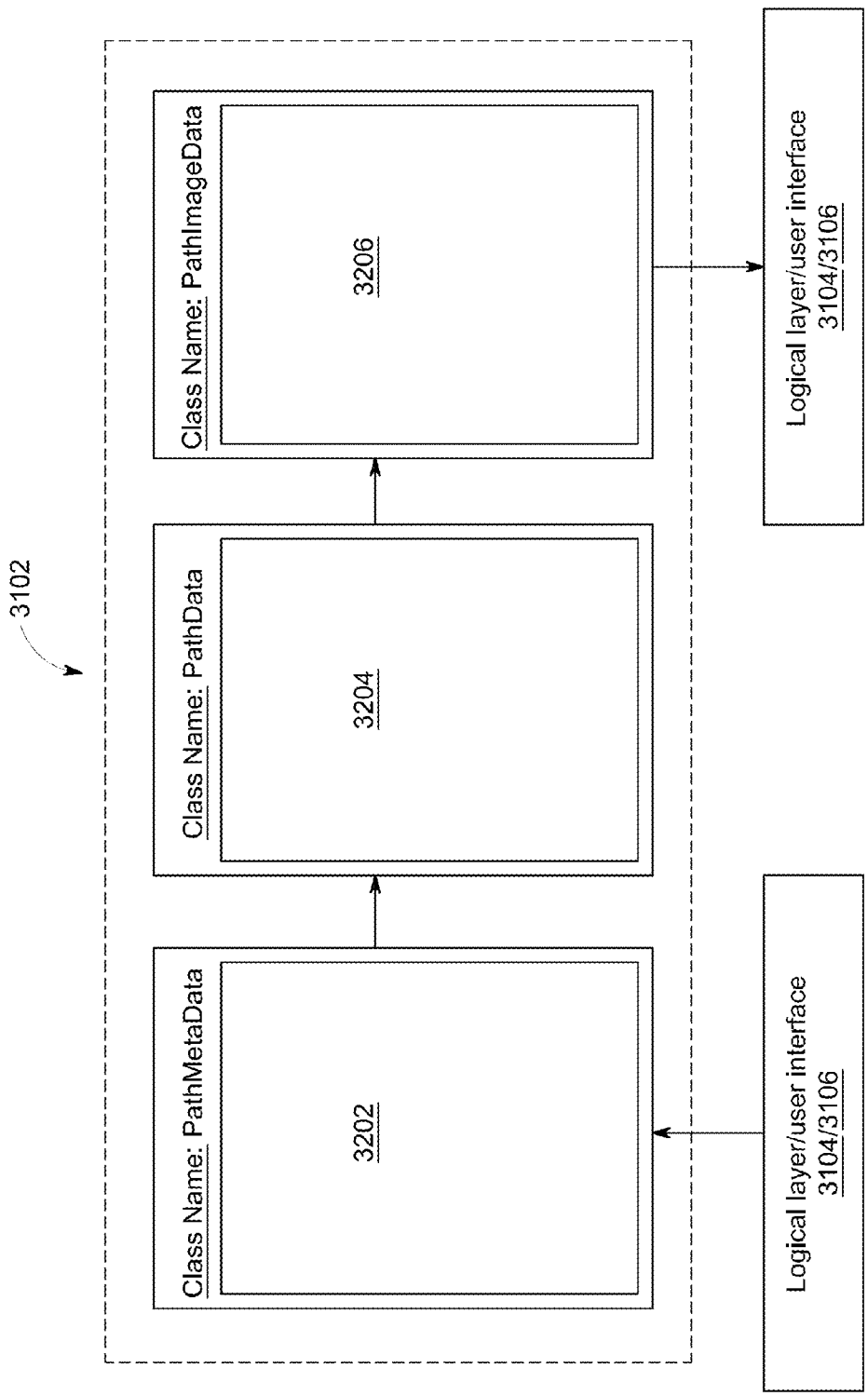
FIG. 32 is a block diagram showing an exemplary data layer.

FIG. 32 is a block diagram illustrating an exemplary object-oriented implementation of the data layer 3102. The exemplary data layer may include a class named "PathMetaData" 3202 that is an interface class prescribing the design of a class to read in and store metadata for the application. The class may manage all metadata for an application, such as, types of images to handle, file names of image and/or statistical data files, number of images, and the like. Exemplary inputs to the class may include, but are not limited to, the source of the metadata, such as, flat files, database connections, and the like.

The exemplary data layer may also include a class named "PathData" 3204 that is an interface class that prescribes the design of a class that sets up an application for data access. The class may manage file access paths for the different types of images and/or statistical data, book-keeping variables (such as, number of slides/spots, number of markers, statistical lists), and the like. Exemplary inputs to the class may include, but are not limited to, a class derived from the PathMetaData interface class. In response to receiving a file access path for a study, the "PathData" class may retrieve all image and/or text data corresponding to the selected study/slide/spot and create one or more suitable data structures to house the retrieved data. In an exemplary embodiment, data corresponding to a particular study/slide/spot retrieved by the "PathData" class may be stored in a structured array that is indexed by identifiers, for example, identifiers for different slides, identifiers for different spots, and identifiers for biomarkers or DNA sequences, and the like. The storage of data corresponding to a study/slide/spot in an array organization and indexing of the data allows easy and time-efficient retrieval of selected data corresponding to the particular study.

The exemplary data layer may include a class named "PathImageData" 3206 that is an interface class that prescribes the design of a class for reading images and populating lists of images in specified orders, if required. The class may manage one or more file streams used to read files and/or images in the database, memory allocated to store temporary data and/or variables during the data access operations, and the like. Exemplary inputs to the class may include, but are not limited to, a class derived from the PathData interface class, information on specific images to be read, and the like. In response to receiving inputs that specify types or locations of data, the "PathImageData" class may query the data structures generated by the "PathData" class to selectively retrieve the data specified in the input. In an exemplary embodiment, the "PathImageData" class may load only the requested data from the "PathData" class, which allows time-efficient retrieval and processing of data. After accessing the requested data in the "PathData" class, the "PathImageData" class may transmit the data to the logical layer and/or the UI layer. The "PathImageData" class may transmit the data in any suitable format, for example, as aggregated blocks of data, as streaming data, and the like.

One of ordinary skill in the art will recognize that one or more additional classes or fewer classes than those shown in FIG. 32 may be included in the data layer.

Figure 33:
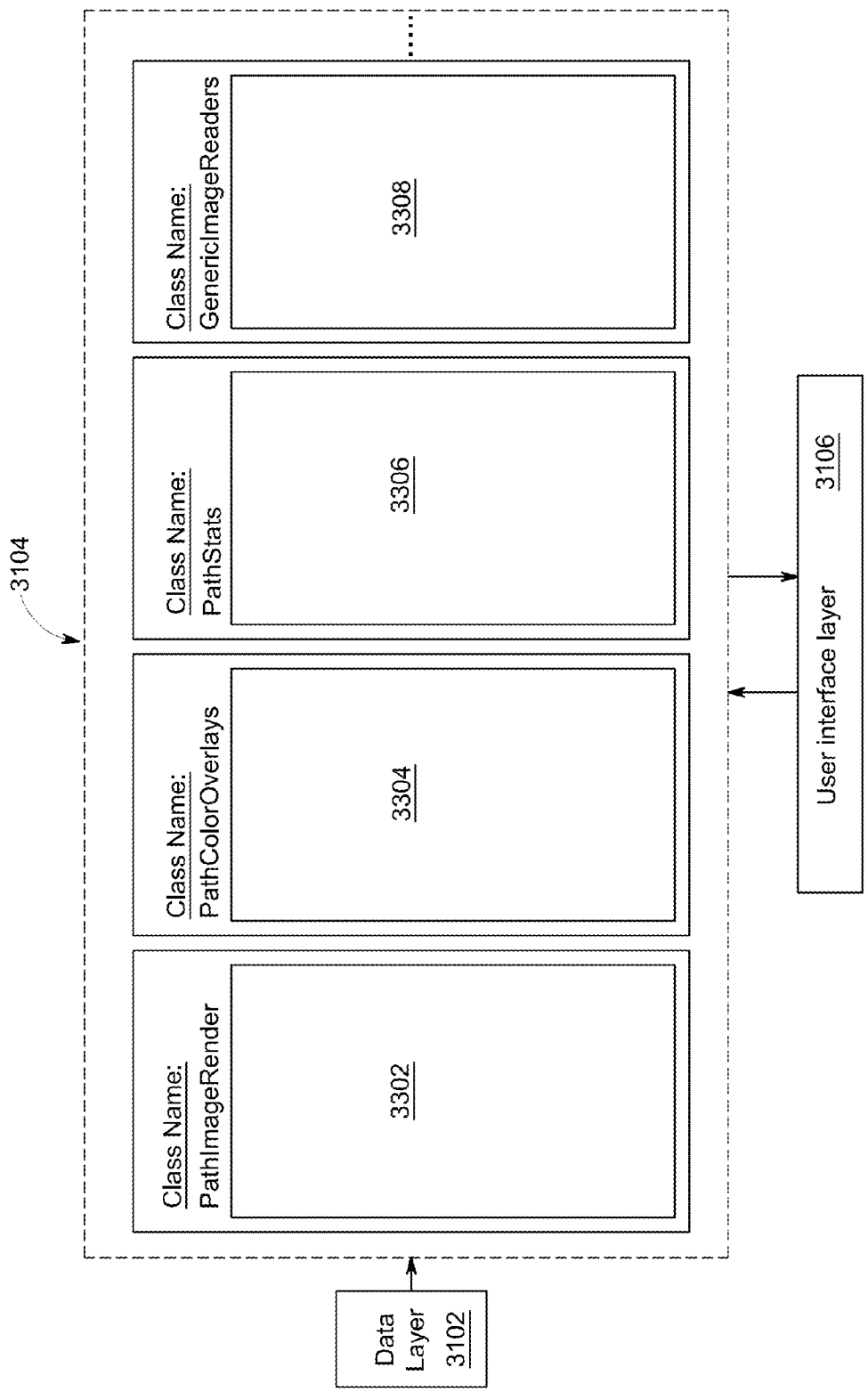
FIG. 33 is a block diagram showing an exemplary logical layer.

FIG. 33 is a block diagram illustrating an exemplary object-oriented implementation of the logical layer 3104. The exemplary logical layer may include a class named "PathImageRender" 3302 that is an interface class that prescribes the design for a class for implementing or using a specified image viewer. In an exemplary embodiment, the "PathImageRender" class may receive requests and inputs from the UI layer, and request the requested data from the "PathImageData" class of the data layer. In turn, the "PathImageRender" class may process the received data and transmit the raw and/or processed data for display using the UI layer. Exemplary operations of the "PathImageRender" class may include, but are not limited to, creating images and maps of biological tissue for rendering in the UI layer, creating overlays of expression of biomarkers and/or DNA sequences, setting and/or changing the color, contrast/brightness and/or transparency of the images and maps, and the like.

The "PathImageRender" class may manage all aspects required to implement or use an image viewer, including, but not limited to, managing the overlays, managing the window-level and window-width variables, managing the zoom and pan variables, managing the most recently generated color overlays, clearing the overlays, and the like.

The exemplary logical layer may include a class named "PathColorOverlays" 3304 that is an interface class that prescribes the design for any class that is used to generate color overlays. Exemplary inputs to the class may include, but are not limited to, one or more images, user-specified parameters for the color display, and the like. The class may manage all aspects of color overlays, such as, the colors used in the overlays, index maps for display, input images, and other user-specified parameters.

The exemplary logical layer may include a class named "PathStats" 3306 that is an interface class that prescribes the design for any class that is used to read in statistical data. In an exemplary embodiment, the "PathStats" class may interface with the UI layer to receive requests and may receive as input access to statistical analyses. In an exemplary embodiment, the "PathStats" class may perform one or more operations associated with visualizing the statistical data. The statistical analyses and/or visualizations generated or read in by the "PathStats" class may be transmitted to the UI layer for display on one or more user interfaces. The class may manage all aspects of specified statistical analyses including, but not limited to, cell IDs (for single-cell analysis), types of statistics used, individual statistical values, and the like.

The exemplary logical layer may include a class named "GenericImageReaders" 3308 that is an interface class that prescribes the design for any class used to read in specified image formats. Exemplary inputs to the class may include, but are not limited to, one or more file streams and/or one or more file names for images or image formats. The class may manage all aspects for the specified image formats.

In an exemplary embodiment, the logical layer may include a class named "PathCluster" (not illustrated) that, in an exemplary embodiment, performs one or more clustering methods or algorithms on a plurality of biological units to identify clusters of units having one or more similar or identical characteristics. Exemplary characteristics may include, but are not limited to, morphological characteristics, functional characteristics, biomarker expression levels, and the like. For example, a clustering method may identify a first cluster of cells having high expression levels of a first biomarker, a second cluster of cells having high expression levels of a second biomarker, and a third cluster of cells that are larger than a threshold size, and the like. Based on the clusters of biological units identified by the "PathCluster" class, the "PathImageRender" may generate visualizations of the identified clusters in different corresponding colors for display on a user interface.

In an exemplary embodiment, the logical layer may include a class named "PathQueries" (not illustrated) that, in an exemplary embodiment, performs queries on biological units to select units that satisfy one or more selection criteria. Exemplary selection criteria may include, but are not limited to, one or more morphological characteristics, one or more biomarker expression levels, one or more functional characteristics, and the like. Based on the identification of one or more biological units that satisfy the selection criteria by the "PathQueries" class, the "PathImageRender" may generate visualizations of the identified biological units in different corresponding colors for display on a user interface.

One of ordinary skill in the art will recognize that one or more additional classes or fewer classes than those shown in FIG. 33 may be included in the logical layer.

The UI layer may define and implement one or more classes and/or one or more methods for rendering one or more user interfaces on a visual display device. An exemplary user interface may receive user selections and data from the data layer. In response, the user interface may render or display image and/or text data requested by the user.

In an exemplary embodiment, the user interface may perform bookkeeping to record the selections made by the user. The user interface may load in one or more overlay masks that are selected by a user, and may allow the user to set and change colors and contrast/brightness levels for displaying the overlay masks. In one example, an overlay mask may display expression levels of a user-selected marker. In another example, an overlay mask may display expression or non-expression of a user-selected DNA sequence. Image data corresponding to the expression and non-expression of DNA sequences may be obtained using fluorescence in situ hybridization (FISH). In an exemplary embodiment, the user interface may perform bookkeeping to record and store the user-selected overlay masks, and the user-selected colors and contrast/brightness levels for displaying the user-selected overlay masks.

The data layer, logical layer and UI layer may define classes for different types of biological units rendered on a user interface in accordance with exemplary embodiments. For example, a "BiologicalUnit" class may be provided to generally define biological units, for example, nuclei, cells, tissues, membranes, and the like. One or more classes may be defined for each type of biological unit, for example, a "Nucleus" class for defining nuclei, a "Cell" class for defining cells, and the like. In an exemplary embodiment, the "BiologicalUnit" class may be an interface that is implemented by the specific "Cell," "Nuclei," etc., classes. One or more sub-classes may be defined based on the "Cell" class to define specific types of cells, for example, a "Myocyte" class for defining muscle cells.

A class may include indications of zero, one or more attributes associated with properties or characteristics of the class objects. The attribute values may be specified for a particular class object when the class is instantiated. A class may also include zero, one or more methods associated with the behavior exhibited by class objects at program run time. The methods may have access to data stored in a class object and may be able to control or set the attributes of the class object. One or more instances may be created from each class, for example, cell objects may be instantiated from the "Cell" class, nuclei objects may be instantiated from the "Nuclei" class, and the like. The object instantiations may be made persistent so that the states of the objects may be saved during a current session and reloaded from memory for future sessions.

FIG. 34 is a block diagram of an exemplary "Cell" class 3400 for defining cells in biological tissue. One of ordinary skill in the art will recognize that any suitable class structure and class components may be used to define cells, and that such class structures and components are not limited to the illustrative embodiment of FIG. 34.

The class 3400 may include one or more attributes 3402 associated with cells that may be displayed in one or more user interfaces in the UI layer. The attributes may include, but are not limited to, a unique identifier for the cell, a sample identifier identifying a sample, test, slide, and/or spot in which the cell was identified, a tissue identifier identifying a tissue that the cell is part of, and the like. The attributes may also include, but are not limited to, one or more types corresponding to the cell (e.g., a structural type like red blood cell, a morphological type like oversized, a diagnostic type like diseased, and the like), a size of the cell, the boundaries of the cell (e.g., the boundaries of the cell on an image of biological tissue), a location of the cell (e.g., a location of the cell on an image of biological tissue), and the like. The attributes may also include, but are not limited to, one or more expression levels associated with the cell (e.g., expression levels of one or more biomarkers, expression of one or more DNA sequences), and the like.

The class 3400 may include one or more methods 3404, and exemplary embodiments may provide a code generation module for generating code associated with the methods. The code may be executed at run time to perform the functionality encapsulated in the methods.

In exemplary embodiments, the class may include one or more "get" methods for obtaining the values of one or more attributes of a class object and one or more "set" methods for setting the values of one or more attributes of a class object. In an exemplary embodiment, a "getIdentifier" method and a "setIdentifier" method may allow obtaining and setting, respectively, the value of the "Identifier" attribute that designates the unique identifier of a cell. A "getSampleIdentifer" method and a "setSampleIdentifer" method may allow obtaining and setting, respectively, the value of the "SampleIdentifier" attribute that designates a sample, test, slide, spot in which a cell was identified. A "getTissueIdentifier" method and a "setTissueIdentifier" method may allow obtaining and setting, respectively, the value of the "TissueIdentifier" attribute that designates a tissue of which a cell is part. A "getType" method and a "setType" method may allow obtaining and setting, respectively, one or more type categorizations of a cell. A "getSize" method and a "setSize" method may allow obtaining and setting, respectively, the size of a cell. A "getBoundaries" method and a "setBoundaries" method may allow obtaining and setting, respectively, the boundaries of a cell.

A "getExpressionLevel" method and a "setExpressionLevel" method may allow obtaining and setting, respectively, expression in a cell of one or more biomarkers and/or one or more DNA sequences. A plurality of "getExpressionLevel" and "setExpressionLevel" methods may be provided, with each get and set method pair corresponding to a biomarker or a DNA sequence whose expression may be rendered for a cell.

A "renderCell" method may be provided to visually render a representation of a cell on a user interface. In exemplary embodiments, the "renderCell" method may use the "get" methods to obtain attribute values corresponding to a cell, and may use the attribute values in rendering the representation of the cell.

In an exemplary embodiment, the value of the "Size" attribute may be rendered on the user interface, for example, as a relative size of the representation of a cell. In an exemplary embodiment, the value of the "Boundaries" attribute may be rendered on the user interface, for example, as the pixels on the user interface representing the boundary of a representation of a cell. In an exemplary embodiment, the value of the "Location" attribute may be rendered on the user interface, for example, the location on the user interface of a representation of a cell relative to the locations of the representations of surrounding biological units. In an exemplary embodiment, the value of an "ExpressionLevel" attribute may be rendered on the user interface, for example, as an intensity of a color representing a cell.

In describing exemplary embodiments, specific terminology is used for the sake of clarity. For purposes of description, each specific term is intended to, at least, include all technical and functional equivalents that operate in a similar manner to accomplish a similar purpose. Additionally, in some instances where a particular exemplary embodiment includes a plurality of system elements or method steps, those elements or steps may be replaced with a single element or step. Likewise, a single element or step may be replaced with a plurality of elements or steps that serve the same purpose. Further, where parameters for various properties are specified herein for exemplary embodiments, those parameters may be adjusted up or down by 1/20th, 1/10th, 1/5th, 1/3rd, 1/2nd, and the like, or by rounded-off approximations thereof, unless otherwise specified. Moreover, while exemplary embodiments have been shown and described with references to particular embodiments thereof, those of ordinary skill in the art will understand that various substitutions and alterations in form and details may be made therein without departing from the scope of the invention. Further still, other aspects, functions and advantages are also within the scope of the invention.

Exemplary flowcharts are provided herein for illustrative purposes and are non-limiting examples of methods. One of ordinary skill in the art will recognize that exemplary methods may include more or fewer steps than those illustrated in the exemplary flowcharts, and that the steps in the exemplary flowcharts may be performed in a different order than shown.

The invention claimed is:

1. A computer-implemented method for performing quality review of analysis of biological tissue, the method comprising:
rendering a graphical user interface on a visual display device;
rendering, on the graphical user interface, a field of view selection component allowing a user to select a field of view from a data set comprising tissue profile data including multiplexed biomarker images capturing expression of a plurality of biomarkers in a plurality of fields of view of biological tissue, the field of view selection component allowing the user to configure a color and/or a transparency of a representation on the graphical user interface of biological tissue corresponding to a selected field of view;
in response to user input selecting a field of view corresponding to a biological tissue at the field of view selection component, rendering, on the graphical user interface, a first image of the selected field of view corresponding to the biological tissue;
rendering, on the graphical user interface, a morphological analysis selection component allowing a user to select a morphological analysis of multiplexed biomarker image data corresponding to the selected field of view, the morphological analysis selection component allowing the user to configure a color and/or a transparency of a representation of a result of a selected morphological analysis;
in response to user input selecting a first morphological analysis at the morphological analysis selection component, overlaying, on the first image of the biological tissue, a representation of a first result of the selected first morphological analysis, the first result of the first morphological analysis indicating one or more morphological features of interest in the first image, wherein the first image of the biological tissue and the representation of the first result are displayed in a visually distinguishable manner; and
rendering, on the graphical user interface, a quality review selection component allowing the user to select a quality review score based on a comparison between the first image and the representation of the first result of the first morphological analysis rendered on the graphical user interface.

2. The method of claim 1, further comprising:
receiving a quality review score from the user, at the quality review selection component on the user interface, indicating one or more quality aspects of the first result of the first morphological analysis.

3. The method of claim 2, further comprising:
sending instructions to store, on a storage device, the quality review score in association with the multiplexed biomarker image data corresponding to the selected field of view of the biological tissue and the selected first morphological analysis.

4. The method of claim 2, wherein the instructions further indicate that the quality review score is to be stored in association with an identification of the user providing the quality review score.

5. The method of claim 1, further comprising:
receiving user input to change the first image to a second image of the selected field of view; and
in response to the user input, removing the first image from the user interface and rendering the second image of the selected field of view on the graphical user interface, while continuing to render the representation of the first result of the first morphological analysis such that the second image is overlaid by the representation of the first result of the first morphological analysis.

6. The method of claim 1, further comprising:
receiving user input to change the first result of the first morphological analysis to a second result of a second morphological analysis performed on the multiplexed biomarker image data, the second result of the second morphological analysis indicating one or more morphological features of interest in the first image; and
in response to the user input, removing the representation of first result of the first morphological analysis from the user interface and overlaying, on the first image, a representation of the second result of the second morphological analysis.

7. The method of claim 1, further comprising:
overlaying, on the first image and the representation of the first result, a representation of a second result of a second morphological analysis performed on the multiplexed biomarker image data, the second result of the second morphological analysis indicating one or more morphological features of interest in the first image.

8. The method of claim 1, wherein the first morphological analysis includes running an image segmentation algorithm implemented on a computing device on the multiplexed biomarker image data, and wherein the first result of the first morphological analysis includes a set of one or more segments delineating one or more biological units of interest in the first image.

9. The method of claim 8, wherein a biological unit of interest is a cell, and wherein the one or more segments trace cell membranes displayed on the first image.

10. The method of claim 8, wherein a biological unit of interest is a collection of cells.

11. The method of claim 8, wherein a biological unit of interest is a sub-cellular component of a cell.

12. The method of claim 8, wherein the quality review score includes a segmentation quality score that indicates an evaluation of a performance of the image segmentation algorithm.

13. The method of claim 12, further comprising:
automatically determining that one or more segmentation quality scores, corresponding to results generated by a single image segmentation algorithm run on one or more images of a type of biological tissue, are below a predefined quality threshold; and
automatically determining that the image segmentation algorithm is unsuitable for processing the type of the biological tissue.

14. The method of claim 8, wherein the quality review score includes a marker quality score that indicates an evaluation of a quality of a marker used to treat the biological tissue prior to capturing the first image of the biological tissue.

15. The method of claim 14, further comprising:
automatically determining that one or more marker quality scores, corresponding to one or more images of a type of biological tissue treated with a single marker, are below a predefined quality threshold; and
automatically determining that the marker is unsuitable for staining the type of the biological tissue.

16. The method of claim 8, further comprising:
receiving user input, at the graphical user interface, selecting one or more morphological units of the biological tissue on the first image to indicate that the selected units are incorrectly identified by one or more segments generated by the image segmentation algorithm; and
adjusting the rendering of the selected units on the graphical user interface to indicate that the selected units are incorrectly segmented.

17. The method of claim 16, further comprising:
removing representations of the selected units of the biological tissue from the first image.

18. The method of claim 1, wherein the first morphological analysis includes running a segment ranking algorithm on the multiplexed biomarker image data, and wherein the first result of the first morphological analysis includes one or more probability indicators corresponding to one or more segments delineating one or more biological units of interest in the biological tissue, each probability indicator indicating whether a corresponding segment correctly identifies the biological unit of interest.

19. The method of claim 1, wherein the biological unit of interest is a cell.

20. The method of claim 18, wherein the first result is represented as numerical rankings represented on the one or more segments on the first image, and wherein higher rankings indicate higher probabilities that the corresponding segments correctly identify the biological units of interest.

21. The method of claim 18, further comprising:
receiving user input, at the user interface, selecting one or more segments represented on the first image to indicate that the selected segments incorrectly identify the biological units of interest; and
adjusting one or more probability indicators corresponding to the selected segments to indicate that the selected segments incorrectly identify the biological units of interest.

22. The method of claim 18, further comprising:
automatically determining that one or more probability indicators corresponding to the segments in the first image are below a predefined threshold; and
recommending an improvement to the user regarding the first morphological analysis.

23. The method of claim 1, further comprising:
receiving user input, at the user interface, to adjust a transparency of the representation of the first result of the first morphological analysis; and
in response to the user input, adjusting the transparency of the representation of the first result to facilitate quality review of the first result.

24. The method of claim 1, further comprising:
receiving user input, at the user interface, to adjust a contrast and/or a brightness of the first image; and
in response to the user input, adjusting the contrast and/or the brightness of the first image.

25. The method of claim 1, further comprising:
receiving user input, at the user interface, to change a color for representing the first result of the first morphological analysis; and
in response to the user input, changing the color in which the first result is represented on the graphical user interface to facilitate quality review of the first result.

26. The method of claim 1, further comprising:
overlaying, on the first image, a second image of the selected field of view corresponding to the biological tissue such that the first result of the first morphological analysis is overlaid on both the first and second images, the first image of the biological tissue obtained by staining the biological tissue with a first marker prior to capturing the first image, and the second image of the biological tissue obtained by staining the biological tissue with a second marker prior to capturing the second image.

27. The method of claim 26, wherein the rendering of the first and second images creates a composite image on the graphical user interface, and wherein a first contribution of the first image to the composite image is configurable and/or a second contribution of the second image to the composite image is configurable.

28. A computer system for performing quality review of analysis of biological tissue, the system comprising:
a visual display device;
a data storage device for storing a data set comprising tissue profile data including multiplexed biomarker images capturing expression of a plurality of biomarkers in a plurality of fields of view of biological tissue; and
a computer processor coupled to the visual display device and the data storage device, the computer processor programmed to:
render a graphical user interface on the visual display device,
render, on the graphical user interface, a field of view selection component allowing a user to select a field of view from the data set stored on the data storage device, the field of view selection component allowing the user to configure a color and/or a transparency of a representation on the graphical user interface of biological tissue corresponding to a selected field of view,
in response to user input selecting a field of view corresponding to a biological tissue at the field of view selection component, render, on the graphical user interface, a first image of the selected field of view corresponding to the biological tissue,
render, on the graphical user interface, a morphological analysis selection component allowing a user to select a morphological analysis of multiplexed biomarker image data corresponding to the selected field of view, the morphological analysis selection component allowing the user to configure a color and/or a transparency of a representation of a result of a selected morphological analysis,
in response to user input selecting a first morphological analysis at the morphological analysis selection component, overlay, on the first image of the biological tissue, a representation of a first result of the selected first morphological analysis, the first result of the first morphological analysis indicating one or more morphological features of interest in the first image, wherein the first image of the biological tissue and the representation of the first result are displayed in a visually distinguishable manner, and
render, on the graphical user interface, a quality review selection component allowing the user to select a quality review score based on a comparison between the first image and the representation of the first result of the first morphological analysis rendered on the graphical user interface.

\* \* \* \* \*